US008067359B2

(12) United States Patent
Hayes et al.

(10) Patent No.: US 8,067,359 B2
(45) Date of Patent: Nov. 29, 2011

(54) COMPOSITION FOR NUTRITIONALLY IMPROVING GLUCOSE CONTROL AND INSULIN ACTION

(75) Inventors: Kenneth C. Hayes, Wellesley, MA (US); Norman Alan Greenberg, New Hope, MN (US); John P. Troup, Plymouth, MN (US); Anne L. Falk, Minneapolis, MN (US); Gianni Biolo, Trieste (IT)

(73) Assignee: Nestec S.A., Vevey (CH)

( * ) Notice: Subject to any disclaimer, the term of this patent is extended or adjusted under 35 U.S.C. 154(b) by 529 days.

(21) Appl. No.: 11/910,817

(22) PCT Filed: Apr. 4, 2006

(86) PCT No.: PCT/US2006/012576
§ 371 (c)(1),
(2), (4) Date: Oct. 5, 2007

(87) PCT Pub. No.: WO2006/108008
PCT Pub. Date: Oct. 12, 2006

(65) Prior Publication Data
US 2008/0193603 A1 Aug. 14, 2008

(30) Foreign Application Priority Data
Apr. 4, 2006 (WO) ............... PCT/US2006/012576

(51) Int. Cl.
*A61K 38/00* (2006.01)
*A61K 31/70* (2006.01)
*A61K 31/22* (2006.01)

(52) U.S. Cl. ............... 514/1.1; 514/23; 514/549

(58) Field of Classification Search ............... 514/2, 23, 514/549, 1.1
See application file for complete search history.

(56) References Cited

U.S. PATENT DOCUMENTS
4,614,663 A * 9/1986 Rule ............... 426/601
6,140,304 A 10/2000 Sears et al.
2005/0002988 A1 1/2005 Mizumoto et al.

FOREIGN PATENT DOCUMENTS
AU 9873118 A * 12/1998
EP 0 843 972 A 5/1998
EP 0 898 900 A 3/1999

OTHER PUBLICATIONS

International Search Report and the Written Opinion dated Nov. 23, 2006, received in counterpart PCT Application No. PCT/US2006/012576 (22 pg).
Cheuvront, "The Zone Diet Phenomenon: A Closer Look at the Science behind the Claims," Journal of the American College of Nutrition, vol. 22, No. 1, pp. 9-17 (2003).
Dansinger et al, "Comparison of the Atkins, Ornish, Weight Watchers, & Zone Diets for Weight Loss & Heart Disease Risk Reduction," JAMA, vol. 293, No. 1, pp. 43-53 (Jan. 5, 2005).
Hein et al., "Linoleic-acid-enriched diet. . .," American Society of Clinical Nutrition, vol. 49, No. 3, pp. 448-456 (Mar. 1, 1989).
Simopoulos, "Is Insulin Resistance Influenced By Dietary Linoleic Acide & Trans Fatty Acids!," Free Radical Biology & Medicine, vo. 17, No. 4, pp. 367-370 (Oct. 1, 1994).
"Glucose Transport Expression Promoter for Preventing & Improving Diabetes, Insulinemia & Insulin Resistance, Comprises Catechin As Active Ingredient," Abstract Only (2003).
Cefalu et al., "Oral Chromium Picolinate Improves Carbohydrate & Lipid Metabolism. . .," American Society of Clinical Nutrition, vol. 132, pp. 1107-1114 (2002).
Greene et al., "Alpha-Lipoic Acid Prevents the Development of Glucose-Induced Insulin Resistance in 3T3-L1 Adipocytes. . .," Metabolism, vol. 50, No. 9, pp. 1063-1069, (Sep. 2001).
Qin et al., "Cinnamon Extract Prevents the Insulin Resistance Induced by a High-Fructose Diet," Hromon & Metabolic Research, vol. 36, No. 2, pp. 119-125 (Feb. 2004).
Clarke, "Polyunsatured Fatty Acid Regulation of Gene Transcription. . .," American Society of Nutritional Sciences, vol. 131, pp. 1129-1132 (2001).
Timar et al., "Metabolic syndrom X: a review," Canadian Journal of Cardiology, vol. 16, no. 6, pp. 779-789 (Jun. 2000).
Howard et al., "Insulin Sensitivity and Atherosclerosis," American Health Association, vol. 93, pp. 1809-1817 (1996).
Bommartini et al., "Guar-Carob Bean Association in the Control of Post-Prandial Hyperglycemia," Società Italiana di Gerontologia e Geriatria, vol. 33, no. 6, pp. 497-504 (1985).

* cited by examiner

*Primary Examiner* — Kevin E Weddington
(74) *Attorney, Agent, or Firm* — K&L Gates LLP

(57) ABSTRACT

Disclosed is a method and composition for nutritionally improving glucose and insulin balance in an individual. The invention further provides a method for treating a comorbidity of diabetes. In one embodiment, the invention provides a nutritional formulation comprising: a protein source; a fat source; and a carbohydrate source, wherein the protein source, the fat source, and the carbohydrate source are in a ratio of about 1:1:1, each comprising about one third of the total calories of the composition.

32 Claims, 18 Drawing Sheets

COMPOSITION FOR NUTRITIONALLY IMPROVING GLUCOSE CONTROL AND INSULIN ACTION

BACKGROUND OF THE INVENTION

1. Technical Field

The present invention relates generally to nutrition and more particularly to a method and nutritional composition for improving glucose and insulin balance in an individual. In one embodiment, the invention provides a nutritional composition having a carbohydrate:fat:protein ratio of about 1:1:1, useful in the treatment of a disease or condition associated with diabetes, such as cardiovascular disease or metabolic syndrome.

2. Related Art

Obesity and Type 2 diabetes mellitus incidence in the US has increased dramatically in the past 3 decades, and especially the past decade. Incidence of Type 2 diabetes, and co-morbidities, such as cardiovascular disease, has increased in direct relation to obesity. The epidemic of these chronic diseases has led to an emphasis on dietary management of obesity and insulin resistance. Intentional weight loss markedly reduces the risk of Type 2 diabetes mellitus and cardiovascular risks. Alternative diets such as "Atkins" or "Ornish" have become increasingly popular over the last couple of decades. These diets focus on extremes of fat or carbohydrate (high fat or high carbohydrate diets).

A very low carbohydrate diet, such as Atkins, is currently popular as a weight loss diet. However, there is no consensus on the levels of carbohydrates, protein and fat in the diet that is optimal for weight management and insulin sensitivity. Few recent studies suggest that high fat/high protein ketogenic diets favor significant weight loss. But, it is not clear whether high protein or high fat or low carbohydrate, or a combination of these factors, in these diets are responsible for the observed metabolic effects. Thus, the effect of macronutrient composition of diet on adiposity and insulin resistance is still unclear.

Macronutrient balance may be a critical factor. High fat diets generally, according to current literature, induced obesity and adiposity in males and females. High-fat diets and high-carbohydrate ad lib diets in females have been shown to impair insulin sensitivity. Also, high carbohydrate diets markedly elevate liver weights, liver triglycerides and liver esterified cholesterol (EC).

Human studies have reported more weight loss with low carbohydrate diets compared to low fat diets. The low carbohydrate diets included foods high in fat and protein resulting in high fat/high protein content. This suggests that the ratio of dietary fat to protein may be a critical factor in regulating energy balance, adipose mass and weight gain. High carbohydrate diets result in the lowest weight gain when caloric intake was restricted to that of high fat/high protein diet. Glucose metabolism and oxidation has been found to be more efficiently up-regulated according to dietary carbohydrate intake. However, high carbohydrate diets have been reported to increase hepatic lipogenesis and reduce fatty acid oxidation and lipolysis, leading to weight gain, likely due to excess caloric intake as carbohydrate.

National Health and Nutrition Examination Survey (NHANES; 1988-94) and Carbohydrate Intake On Obesity (Yang et al. 2003, AJCN 77: 1426) in FIGS. 1-2 shows that high-carbohydrate intake leads to lower insulin secretion. This is accomplished without significant change in the levels of HbA1c, fasting serum glucose, and insulin. This has been interpreted in the literature as insulin is more efficient as carbohydrate increases.

Further, Yang shows that high-fat+high-protein intake leads to higher energy intake, greater BMI, and greater insulin secretion with main shifts occurring at approximately >30% fat (negative impact) and >15% protein (positive impact).

Dansinger, M. et al (JAMA 2005; 293:45-53) compared Atkins Diet (low carbohydrate), Zone Diet (30:30:40 ratio of calories from proteins, fats and carbohydrates), Weight Watchers (low calories, low fat diet) and Ornish (high carbohydrate, low fat). The results showed that at 12 weeks, Ornish, Zone and Weight Watchers all had greater weight loss than Atkins (FIG. 3).

A sample Atkins and Ornish ratio is illustrated in FIG. 4. FIGS. 5-6 illustrate the effect of these diets on weight gain in Diet Induced Obesity (DIO) mice and insulin tolerance on male ApoE-mice.

SUMMARY OF THE INVENTION

The present invention relates to a composition or dietary regimen for increasing insulin sensitivity, lowering insulin resistance, increasing postprandial fat clearance, delaying the appearance of glucose in the blood, and/or lowering plasma insulin levels postprandially, comprising: proteins; fats; and carbohydrates. The present invention further relates to a composition or dietary regimen for treating, preventing and/or delaying the on-set of Type 2 diabetes and its co-morbidities, useful in its continuum from euglycemic and normal insulin production and function to insulin dependency and pancreatic exhaustion. The invention may further be employed in the treatment and/or prevention of obesity.

During the experimentations described in detail below, it was surprisingly found that when the proteins and the fats are in a 1:1 ratio, each comprising about 15% to about 45% of the total calories of the composition, the insulin resistance of the subject animal was appreciably diminished. The composition or dietary regimen can be administered to a mammal, and preferably a human.

In the composition or dietary regimen, the proteins and fats each are about: 20% to about 45% of the total calories of the composition; 20% to about 40% of the total calories of the composition; 25% to about 40% of the total calories of the composition; 25% to about 35% of the total calories of the composition; or 30% to about 35% of the total calories of the composition.

In the composition or dietary regimen, the proteins and fats are preferably about: 15% of the total calories of the composition; 20% of the total calories of the composition; 25% of the total calories of the composition; 30% of the total calories of the composition; 35% of the total calories of the composition; 40% of the total calories of the composition; or 45% of the total calories of the composition.

The composition or dietary regimen, is comprised of greater than about 2% of the total calories of the composition of linoleic acid (18:2). Preferably, the composition or dietary regimen has a linoleic acid (18:2) level of about: 2% to about 10% of the total calories; 3% to about 9% of the total calories; 4% to about 8% of the total calories; 4% to about 7% of the total calories; or 5% to about 6% of the total calories.

Preferably, the composition or dietary regimen has a linoleic acid (18:2) level of about: 2% of the total calories; 3% of the total calories; 4% of the total calories; 5% of the total calories; 6% of the total calories; 7% of the total calories; 8% of the total calories; 9% of the total calories; or 10% of the total calories.

In a particularly preferred embodiment, the composition or dietary regimen further comprises a proportion of carbohydrates substantially equal to the proportion of each of fats and proteins. That is, fats, carbohydrates, and proteins are provided substantially in a 1:1:1 ratio.

A composition or dietary regimen according to the invention may include one or more nutritional products capable of improving glycemic control and/or comorbidities associated with diabetes, such as cardiovascular disease, dyslipidemia, retinopathies, changes in collagen tissue, inflammation, and insulin resistance. Suitable products include, for example, Touchi Extract, partially hydrolyzed guar gum, inulin, fructooligosaccharides, galactooligosaccharides, isomaltulose, Sucromalt, Trehalose, lipoic acid, 4-hydroxyisoleucine, catechins, cinnamon, banaba extract, Madeglucyl, arginine, branched chain amino acids (BCAAs) (i.e., leucine, isoleucine, and valine), glutamine, glutamate, fish oil, chlorogenic acid, mangosteen, palm oil mill waste, chromium, vanadium, witch hazel, allspice, bay leaves, nutmeg, cloves, mushrooms, soluble viscous fiber (including, but not limited to beta-glucan) and saccharomyces cerevisiae.

The illustrative aspects of the present invention are designed to solve the problems herein described and other problems not discussed, which are discoverable by a skilled artisan.

DETAILED DESCRIPTION

Figure 1:
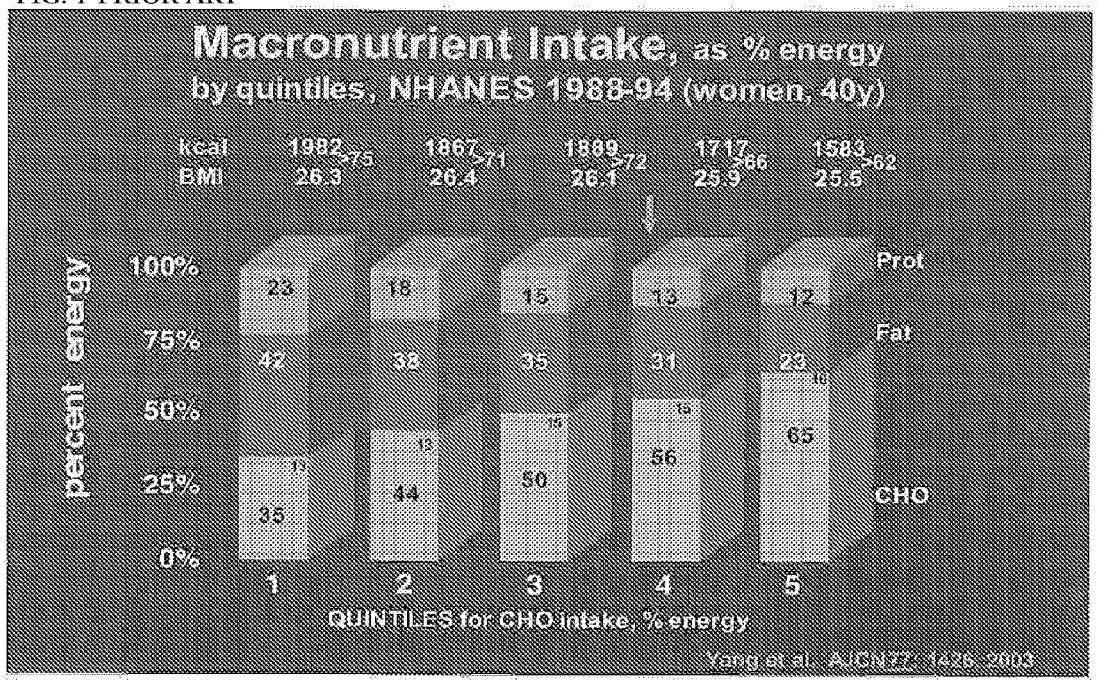
FIG. 1 illustrates macronutrient intake as percent of energy.
Figure 2:
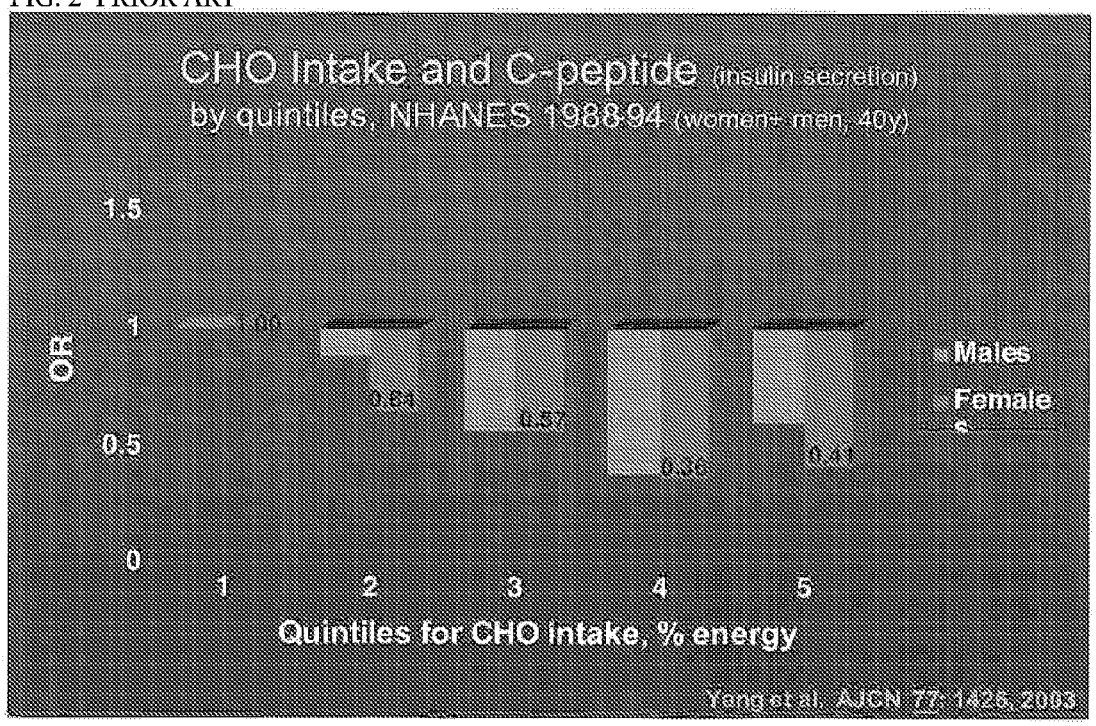
FIG. 2 illustrates CHO intake and C-peptide.
Figure 3:
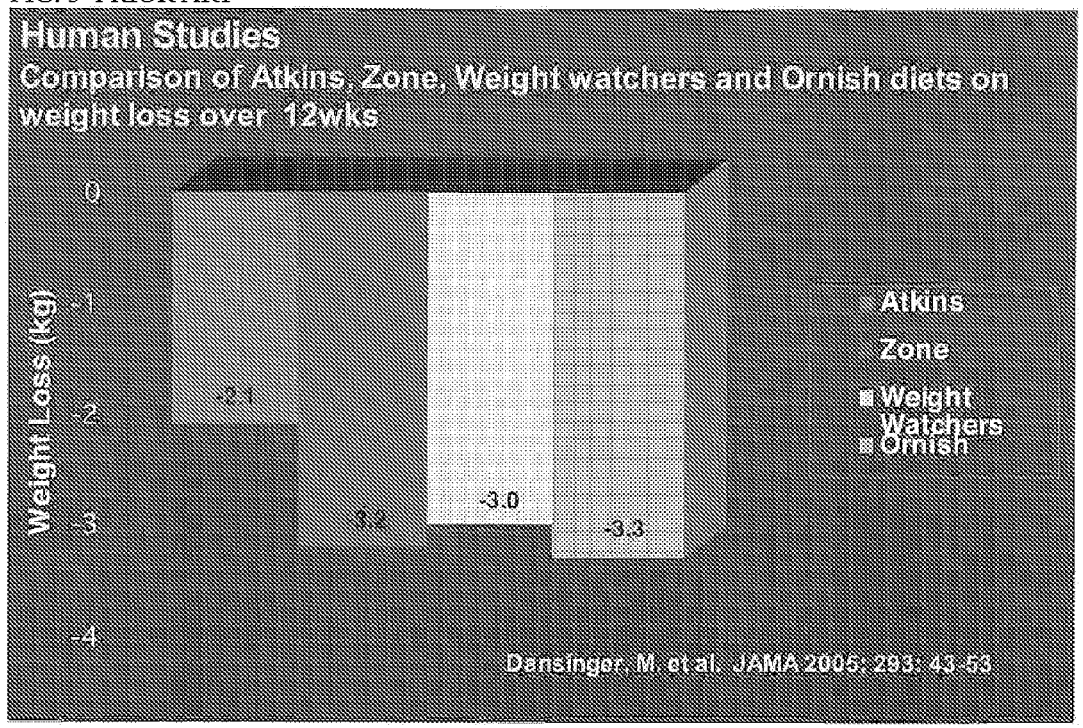
FIG. 3 illustrates comparison of Atkins, Zone, Weight Watchers, and Ornish diets on weight loss over 12 weeks.
Figure 4:
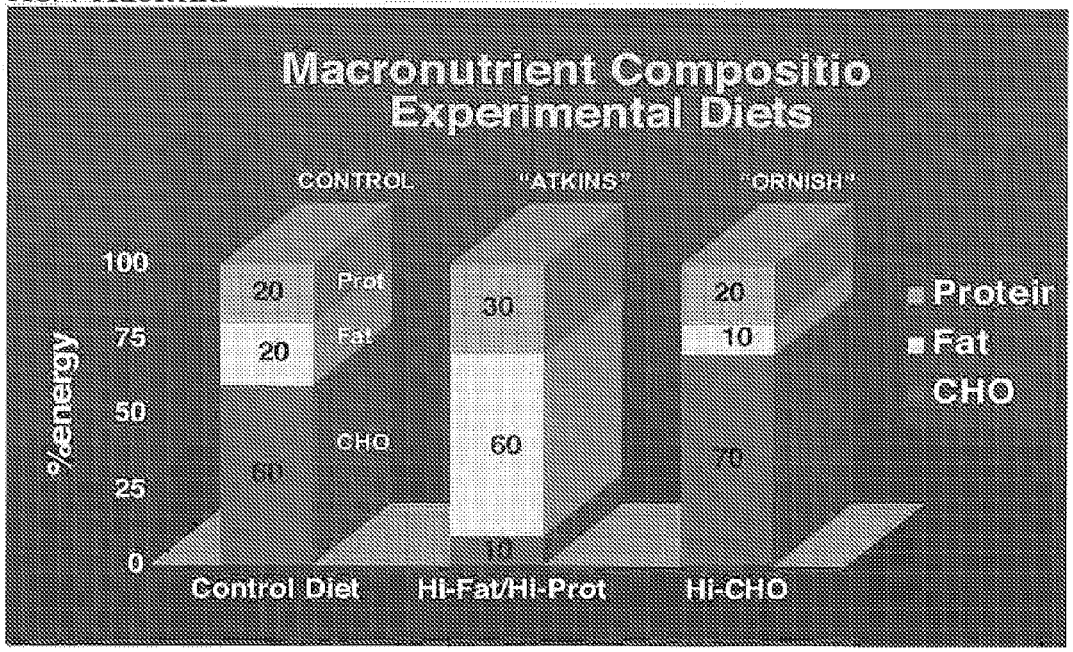
FIG. 4 graphically illustrates macronutrient composition experimental diets.
Figure 5:
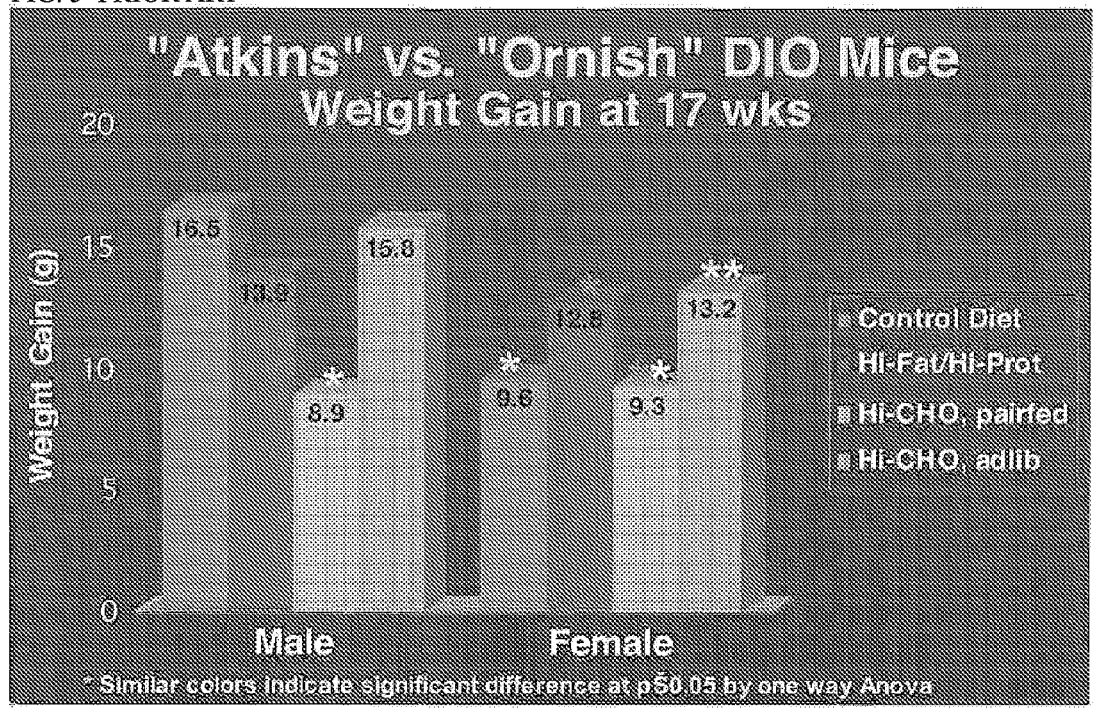
FIG. 5 graphically illustrates Atkins versus Ornish DIO mice weight gain at 17 weeks.
Figure 6:
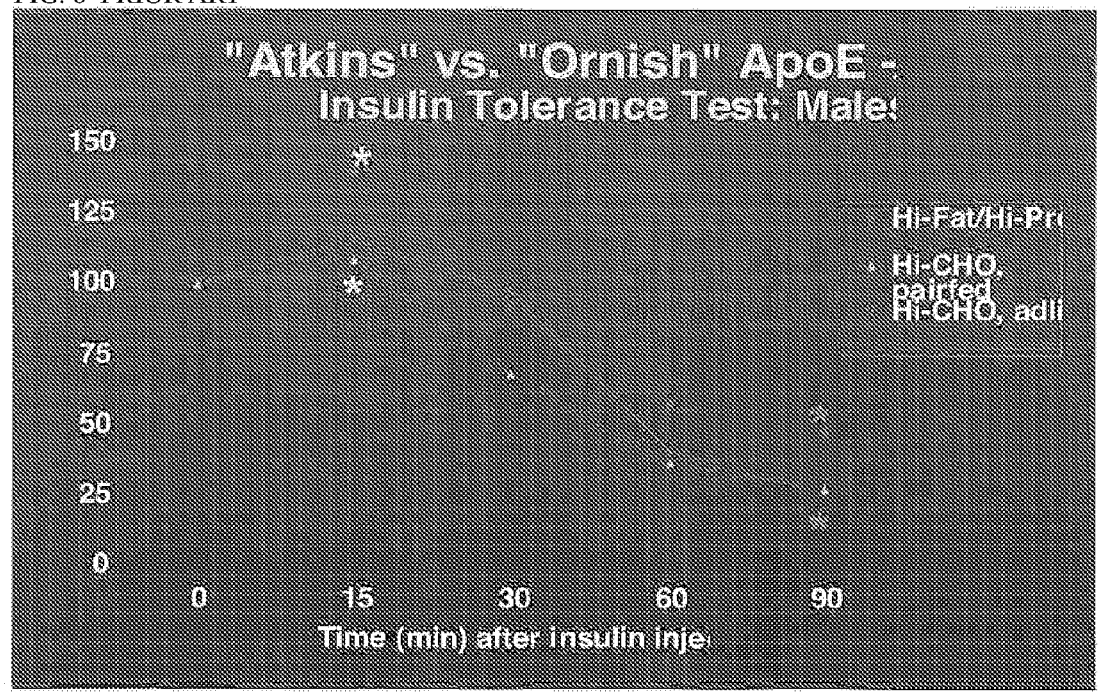
FIG. 6 graphically illustrates Atkins versus Ornish ApoE - insulin tolerance test.

As used throughout, ranges are used as a shorthand for describing each and every value that is within the range. Any value within the range can be selected as the terminus of the range. When used, the phrase "at least one of" refers to the selection of any one member individually or any combination of the members. The conjunction "and" or "or" can be used in the list of members, but the "at least one of" phrase is the controlling language. For example, at least one of A, B, and C is shorthand for A alone, B alone, C alone, A and B, B and C, A and C, or A and B and C.

All values contained throughout this application, including the claims are deemed to be approximate, whether or not the term "about" is used, unless specifically stated as exact.

A dietary regimen includes, but is not limited to, a combination of food and/or drink items that fall into certain parameters (i.e. food and/or drink items that when taken together, contain a ratio of fat to protein of 1:1).

The term "mammal" includes, but is not limited to rodents, aquatic mammals, domestic animals such as dogs and cats, farm animals such as sheep, pigs, cows, and horses, and humans. Wherein the term mammal is used, it is contemplated that it also applies to other animals that are capable of the effect exhibited or intended to be exhibited, by the mammal.

Diabetes as used herein refers to states of physiologic function that fall along a continuum from euglycemic and normal insulin production and function to insulin dependency and pancreatic exhaustion, including, but not limited to: impaired glucose tolerance, insulin resistance, decreased insulin sensitivity, insulin dependence, including Type 1 and Type 2 Diabetes Mellitus.

Co-morbities of diabetes include: cardiovascular disease, dyslipidemia, retinopathies, changes in collagen tissue, inflammation, and insulin resistance.

The present invention relates to a composition or dietary regimen for increasing insulin sensitivity, lowering insulin resistance, increasing postprandial fat clearance, delaying the appearance of glucose in the blood, and/or lowering plasma insulin levels postprandially, comprising: proteins; fats; and carbohydrates. The present invention further relates to a composition or dietary regimen for treating, preventing and/or delaying the on-set of Type 2 diabetes and its co-morbities, useful in its continuum from euglycemic and normal insulin production and function to insulin dependency and pancreatic exhaustion.

During the experimentations described in detail below, it was surprisingly found that when the proteins and the fats are in a 1:1 ratio, each comprising about 15% to about 45% of the total calories of the composition, the insulin resistance of the subject animal was appreciably diminished. The composition or dietary regimen can be administered to an animal, preferably a mammal, and most preferably a human.

In the composition or dietary regimen, the proteins and fats each are preferably about: 20% to about 45% of the total calories of the composition; 20% to about 40% of the total calories of the composition; 25% to about 40% of the total calories of the composition; 25% to about 35% of the total calories of the composition; or 30% to about 35% of the total calories of the composition.

In the composition or dietary regimen, the proteins and fats are preferably about: 15% of the total calories of the composition; 20% of the total calories of the composition; 25% of the total calories of the composition; 30% of the total calories of the composition; 35% of the total calories of the composition; 40% of the total calories of the composition; or 45% of the total calories of the composition.

The composition or dietary regimen, is comprised of greater than about 2% of the total calories of the composition of linoleic acid (18:2). Preferably, the composition or dietary regimen has a linoleic acid (18:2) level of about: 2% to about 10% of the total calories; 3% to about 9% of the total calories; 4% to about 8% of the total calories; 4% to about 7% of the total calories; or 5% to about 6% of the total calories.

Preferably, the composition or dietary regimen has a linoleic acid (18:2) level of about: 2% of the total calories; 3% of the total calories; 4% of the total calories; 5% of the total calories; 6% of the total calories; 7% of the total calories; 8% of the total calories, 9% of the total calories; or 10% of the total calories.

Based on human studies, we investigated metabolic effects of altering macronutrient balance in two mouse models namely diet induced obesity (DIO) C57BL/6 and ApoE (−/−) mice.

The ApoE (−/−) mice gained lower weight and had lower adipose mass compared to DIO mice. Differences between high carbohydrate calorie restricted and ad lib fed animals were not seen in ApoE (−/−) mice. This is probably due to impaired triglycerides transport/uptake in ApoE (−/−) mice.

Increasing the protein content of diet, at moderate fat intake reduced the risk of obesity. A fat-to-protein ratio of 1.0 with 40% of total calories (% en) from carbohydrates resulted in low weight gain and low adipose deposits. Substituting protein for carbohydrate in a high carbohydrate diet significantly improved obesity and cardiovascular risk factors. However, protein intake at >30% en tended to impair insulin sensitivity and increase kidney weights in DIO mice. Fat substitution of carbohydrate lead to increased weight gain and insulin resistance.

These studies suggest that macronutrient balance in the diet may be a critical factor for reducing the risk of obesity, insulin resistance and cardiovascular disease. The fat-to-protein ratio, in addition to the overall amount of fat and protein, appear to be important considerations in weight-loss diets.

Studies

The invention is further described in the following examples. The examples are merely illustrative and do not in any way limit the scope of the invention as described and claimed.

A total of 17 studies have been conducted. The first five studies measured the effects of dietary fat type and quantity on blood lipid profile and insulin tolerance. The objective of the remaining 12 studies was to measure the effects of manipulation of dietary macronutrient distribution on insulin sensitivity and blood lipid profile.

Two strains of mice were used: the ApoE (−/−), which develop hypercholesterolemia, atherosclerosis, and insulin resistance with a challenge diet, and the Diet Induced Obese C57BL/6J, which is a Wild Type mouse that becomes insulin resistant and obese, with supporting changes in plasma and hepatic lipids in response to diet. A key finding is the observation that relationships between total fat intake and the diet fat/protein ratio (as % energy), which by definition also affects the fat/carbohydrate ratio, seem to be important to understanding the development of obesity.

It was surprisingly found that the incorporation of linoleic acid (18:2) in amounts greater than 2% of total energy improved insulin sensitivity and postprandial fat clearance. These findings indicate that: 1) addition of fish oils decreases insulin resistance but seemed to increase linoleic acid requirements; 2) trans fatty acids increase insulin resistance but they may also increase the need for linoleic acid; 3) the increased insulin resistance observed with trans fatty acid consumption may be, in part, secondary to the induced deficiency of linoleic acid.

Insulin sensitivity was measured using a technique of measuring blood glucose concentrations after insulin injection rather than the conventional approach of glucose tolerance tests which monitor appearance of glucose over time after a glucose load. The insulin tolerance test is believed to be the best indicator of insulin function/insulin resistance under the current dietary circumstances.

The data in Study 7 were the first to show that the ratio of dietary fat to protein modulates insulin sensitivity. Raising the protein level to 45% of energy with a constant fat intake (30%) reduced insulin sensitivity. Findings from a follow-up study (#17) indicated that a fat:protein ratio of 1:1 resulted in no change in insulin resistance, as would be expected by raising the fat. Insulin resistance was the same when the animals were fed a 1:1 ratio of energy from protein and fat regardless of whether the amounts of protein and fat were 40% or 33%. Insulin resistance was decreased when the animals were fed a 1:1 ratio of protein and fat (40% each) than when the animals received a similar amount of protein (45%), but lower amounts of fat (30%). These observations indicate the ratio of protein:fat is more important in modulation of insulin resistance than the amount of dietary protein alone.

Evidence from Study 12 indicates that adipose deposits, insulin resistance, and blood glucose levels were lower when the animals were fed a 1:1 ratio of protein to fat, as compared to when the ratios were 1:2, 1:3.5, and 1:4. Again, these findings provide evidence that insulin sensitivity is optimized when a 1:1 ratio of protein to fat is consumed and that deviating in either direction from the 1:1 ratio increases insulin resistance.

The overall conclusions from this series of experiments are that, in animal models of diabetes: 1) a higher intake of linoleic acid (18:2) is needed to decrease insulin resistance; 2) very long chain n-3 fatty acids reduce insulin resistance but increase the need for linoleic acid; 3) the protein needs are increased and inadequate protein nutriture will increase insulin resistance; and 4) a 1:1 ratio of energy from protein and fat, and preferably a 1:1:1 ratio of energy from protein, fat, and carbohydrates, is optimal for improvement of insulin sensitivity.

Study 1—Fat Type and Effect on Lipid Levels and Insulin Tolerance

Experiments to examine dietary fatty acids using Leptr (−/−) mice, first with what we refer to as TYPE A backcrossed on C57BLK/SJ and subsequently on TYPE B backcrossed on C57BL/6J. The TYPE A were extremely obese with very high blood glucose levels. They were too fragile and broke down metabolically under the pressure of dietary challenge. By carefully blending fats to control all dietary fatty acids, we did manage to gather basic information about n-3 fatty acids on the insulin resistance issue. The diet contained 40% en primarily as saturated fat with only 2% en from 18:2, designed to enhance any effects of n-3 fatty acids. Fish Oil improved their circumstance in terms of insulin sensitivity and plasma triglycerides, suggesting that the n-3 long chain fatty acid were enhancing glucose clearance. However, all of these n-3-supplemented TYPE A mice tended to gain more weight (fat) and their response to an oral fat load (OFTT), was impaired when supposedly a neutral oil (olive) was served as the challenge gavage fat. This raised the question as to whether another fat/oil would present a more representative challenge (see Study 4 in WT mice).

n-3 Eicosapentaenoic acid (EPA)+Docosahexaenoic acid (DHA) aid diabetic glucose metabolism and insulin tolerance test (ITT), with some questions being raised about postprandial fat clearance and added weight gain. Also, it appeared that 18:3 n-3 may have exacerbated the marginal 18:2 intake more than n-3 long chain fatty acid. In summary, evidence suggested that essential fatty acid status is key for diabetics; i.e. maybe they have a higher 18:2 requirement, which should be factored into any dietary intervention on their behalf. Therefore, the addition of fish oil to a diet improves insulin sensitivity and plasma triglycerides, suggesting that n-3-polyunsaturated fatty acids (PUFA) enhance glucose clearance. However, all of the mice receiving n-3-supplementation tended to gain more adipose weight and their response to an oral fat load using olive oil was impaired. Thus, glucose control is improved but body weight was increased. Evidence suggested that essential fatty acid status is key for diabetics and they may have a higher polyunsaturated fatty acids (18:2) requirement, which should be factored into any dietary intervention.

Study 2

Studies 2 and 5 were combined (n=18) where we compared TYPE B Leptr (−/−) (Study2) with the Wild Type mouse (Study 5) used in the backcross for Leptr (−/−), i.e., C57BL/6J. Here, we also examined the effects of food restriction on TYPE B (which over eat like TYPE A because neither have leptin receptors) and added the design of increasing 18:2 PUFA (increments at 2%, 4%, 6% en) while assessing the insulin sensitivity response. The TYPE B mouse was more stable and better experimental mouse than TYPE A, but very hard to sustain. They had lower glucose than TYPE A, better insulin testing, yet became obese and insulin resistant, glucose intolerant, etc. In addition, when TYPE B was restricted to normal food intake, they had ITT approaching WT normal mice, indicating that their insulin/obesity problem was directly tied to overeating (like Type 2 humans). Adding 18:2 to WT mice appeared to increase sensitivity to insulin, as some mice died with insulin coma upon i.p. insulin before we could dose them with glucose. This was the second clue (after n-3 FA in Study 1) that the type and mass of fatty acid intake can have a big influence on mouse insulin dynamics. Also, added 18:2 in Brandeis casual WT improved their OFTT, and these WT had a better OFTT than either TYPE B or DIO WT mice, i.e., two obese models.

Providing diets with increasing amounts (2, 4 and 6% of energy) of polyunsaturated fatty acids (18:2) to mice that had restricting food intake, because they have no leptin receptors and normally overeat, resulted in lower glucose levels and improved insulin sensitivity compared to mice that were not restricted. This indicated that the insulin/obesity problem in this animal model was directly related to overeating very much like humans with Type 2 diabetes.

Study 3—Trans Fat Test of Diabetes Severity

Because trans fatty acids (FA) have a strong correlation between intake and diabetes risk for humans, we fed 3 levels of trans FA (0, 8, 16% en) to a collection of mice available in-house. Nine were genetically altered IR/IRS-1+/−diabetic mice and nine were general wild types from our colony, for a total of 18 mice, six per diet. Trans FA intake did impair ITT relative to control diet (without trans), and impairment was directly associated with trans intake, but not to the degree seen in the LEPTr (−/−) mice. There was a tendency for trans to lower blood lipids, but trans also led to lower food intake.

Trans-fatty acids may increase 18:2 requirement and diabetes susceptibility while depressing appetite (insulin sensitivity was depressed despite lower food intake). Trans fat intake impaired insulin tolerance in mice fed 8 and 16% of energy as trans fat compared to mice on a control diet (0% trans fat). The decreased insulin sensitivity was directly associated with the trans fat intake. However, there was a trend for trans fat to lower blood lipids, but the diets containing trans fat also led to a decreased food intake.

Trans fat may increase the polyunsaturated fatty acids (18:2) requirement and diabetes susceptibility while depressing appetite, as insulin sensitivity was depressed despite lower food intake, which appears counter intuitive.

Study 4—Fat Tolerance Test

Here we asked whether the long term intake of a fat type, i.e., a saturated fat-rich control (2% en 18:2) or that fat supplemented with +2% en EPA+DPA as fish oil, in Brandeis casual WT mice, would generate different postprandial responses if the challenge fats (oral gavage) were varied. We challenged with heavy cream, olive oil, and corn oil to represent saturated, poly-unsaturated, and mono-unsaturated-rich fats.

The responses were, surprising, both in terms of the long-term fat underlying influence and the challenge fat character. Control mice did not respond as well to OFTT as the FO-supplemented mice (more evidence that n-3 PUFA improve fat-insulin metabolism), and OO was the worst challenge for controls while all fats were about the same in FO mice. Note that in these WT mice, long term FO seemed to enhance OFTT, in contrast to TYPE A mice in Study 1. Corn oil gave a peculiar "late double-bounce" in both long term diet groups. The point is that one must choose carefully when selecting and interpreting results of fat challenges (OFTT) in mouse studies (probably applicable to humans and other species, as well). This is partly why we have come to focus on the ITT as the single best indicator of insulin function/insulin resistance under our dietary circumstances. Thus, the interpretation of results from fat challenges must also consider the mouse model that was used. In wild type mice, long-term fish oil supplementation seemed to enhance fat tolerance compared to leptin receptor deficient mice.

Study 5—See Study 2 (Wild Type)

Adding polyunsaturated fatty acids (18:2) to the diets of wild type mice increased their sensitivity to insulin. In addition, providing 18:2 in the diets of wild type mice improved their oral fat load tolerance compared to two other mouse models of obesity.

Study 6—High Fat/High Protein vs. High Carbohydrate/Low Fat Diet Effects on Arterial Atherosclerosis in apoE (−/−) Mice Mice that were apoE deficient were divided into 3 groups: 1) control diet (AHA; 60% CHO, 19% protein, 21% fat); 2) high fat/high protein diet (Atkins; 11% CHO, 30% protein, 59% fat); and 3) high carbohydrate/low fat diet (Ornish; 71% CHO, 18% protein, 11% fat). Fasting plasma lipids, cholesterol, oral glucose tolerance test and insulin tolerance test were conducted after 10 and 12 weeks of diet intervention.

This study represented our first major experiment with atherosclerosis-susceptible, apoE (−/−) mice, applying diet shifts in macronutrients (carbohydrate, fat, protein) that are currently in vogue for humans and which conceptually play directly into our fat/insulin hypotheses. The design had 5 groups with 8 mice/group and compared a control group with two variations (2.4 v. 6.5% en 18:2) of the Atkins diet (high fat, high protein) with two variations (0.5 v. 1.3% en 18:2) of the Ornish diet (high carbohydrate, low fat) diets. Thus, within Atkins/Ornish diet groups, the variations were HIGH and LOW levels of PUFA as 18:2 in order to further tease out an effect on insulin sensitivity by 18:2.

Atkins mice (high caloric density) had lower food and caloric intake than Ornish, but surprisingly no difference in body weight or adipose. Consequently, Ornish mice ate more food and had higher cholesterol intake than Atkins mice. Ornish (male and female) mice had significantly higher plasma TC, liver EC and atherosclerosis compared to Atkins mice. The high-PUFA intake in Ornish mice tended to reduce atherosclerosis in males, but not in females. Ornish males had higher plasma total cholesterol than females, but liver EC was greater in females, while aortic atherosclerosis was similar in males and females. Male atherosclerosis was sensitive to diet intervention (Ornish higher, Atkins lower), while females were more responsive to insulin sensitivity (ITT) with Atkins mice being the more resistant. Thus, carbohydrates generally exerted an adverse effect by driving up liver and plasma cholesterol, presumably because the liver was forced to metabolize the carbohydrate directly and then secreted it as fat along with cholesterol in lipoproteins. This resulted in increased hepatic and blood lipids, as well as atherosclerosis.

Liver cholesterol was a good predictor of atherosclerosis, surprisingly even better than plasma total cholesterol levels. Atkins males had slightly more adipose, tended towards larger kidneys, despite a tendency to eat less, while all Ornish had larger livers. In addition, all Atkins mice had poor ITT, i.e., became more insulin resistant.

This apoE (−/−) atherosclerosis sensitive model shows good responses (insulin sensitivity, blood, aorta and liver lipids, adipose pools) to macronutrient manipulations. High carbohydrate/low fat diets resulted in greater food intake and increased total plasma cholesterol as well as aortic and hepatic cholesterol accumulation compared to high fat/high protein diet. In contrast, the high fat/high protein diet induced insulin resistance and impaired glucose clearance compared to high carbohydrate/low fat diets. These results suggest that specific aspects of high fat/high protein diets and high carbohydrate/low fat diets need to be evaluated before being prescribed to the general population for weight loss and reduction in the risk of coronary heart disease and type 2 diabetes.

Study 7—Effect of Diet Protein (15, 30 and 45% en) on Plasma Lipids and Insulin Sensitivity (ITT) in apoE (−/−) Mice This study examined the level of protein within the context of the ATKINS diet, using ApoE mice sensitive to that diet. Three diet groups had 3 levels of protein (15, 30, 45% en) exchanged for carbohydrate while fat was initially held constant at 30% en (normal) for 12 wk test period. For the subsequent 16 wks, the fat was increased to 50% en (high fat, true Atkins). The low protein (normal) diet was best for insulin sensitivity in females, and high protein was the worst in both sexes. The very high protein greatly reduced adipose tissue, enlarged the kidneys, but was without effect on total cholesterol. The reduced adipose (only with high fat and highest protein) explains the insulin resistance somewhat and also provides a clue why the Atkins diet might work for weight reduction in humans.

Replacing carbohydrate with protein decreased adipose and body weight. However, kidney weight tended to increase, indicating a decrease in function. In addition, the highest protein diet (45% protein) increased plasma cholesterol levels. The lowest protein diet (15% protein) improved insulin sensitivity in female mice and the highest protein diet (45% protein) decreased insulin sensitivity in both male and female mice.

Mice that were ApoE deficient were divided into 3 groups: 1) normal protein diet (55% CHO, 15% protein, 30% fat); 2) high protein diet (40% CHO, 30% protein, 30% fat); and 3) highest protein diet (25% CHO, 45% protein, 30% fat). Fasting plasma lipids, cholesterol, oral glucose tolerance test and insulin tolerance test were conducted after 12 weeks of diet intervention.

Study 8

The objective of this experiment was to determine the relative importance of dietary cholesterol in our mouse models, in this case with cholesterol-sensitive male apoE (−/−) mice. That is, to what degree does their hypercholesterolemia and atherosclerosis development depend on diet cholesterol, as compared to the other dietary macro ingredients as a whole? The three diets were saturated fat-rich and contained either 0, 0.04%, or 0.08% cholesterol for 12 wks. These apoE (−/−) mice proved extremely sensitive to the level of cholesterol intake, essentially doubling their total cholesterol between the control and the highest intake.

Study 10—Dietary Macronutrient Composition and Plasma Lipids and Insulin Sensitivity in C57BL/6J Mice This was a follow-up to study 6 and study 7. Mice with diet-induced obesity were randomized to one of 4 diets: 1) control diet (AHA; 60% CHO, 19% protein, 21% fat); 2) high fat/high protein diet (11% CHO, 31% protein, 58% fat); 3) high fat/normal protein (11% CHO, 19% protein, 70% fat); and 4) high carbohydrate diet pair fed and ad lib fed (70% CHO, 19% protein, 11% fat). Fasting plasma lipids, cholesterol, oral glucose tolerance test and insulin tolerance test were conducted after 12 weeks of diet intervention.

As a follow up to Study 6 and Study 7 in apoE (−/−) mice, this complimentary experiment represented a major undertaking in 50 male and female WT mice (C57BL/6J) as the DIO model to determine whether the ATKINS diet would fair better than ORNISH, as it seemed to do in Study 6. In order to control differences in caloric and cholesterol intake between Atkins/Ornish groups (which was not the case in study 6), one Ornish group (high CHO, low fat) was pair fed (kcals) to Atkins (high fat/high protein) group. These C57BL/6J mice were initially fed a stabilization diet similar to a typical western diet for 2 weeks, followed by one of 5 diets (n=9-10/grp) that varied in carbohydrate, fat, and protein composition as indicated:

Grp 1. American Heart Association (AHA) control, modified fat diet: provided 60% en carbohydrate, 21% en fat, and 19% en protein.

Grp 2. High fat/high protein diet: provided 11% en carbohydrate, 58% en fat, and 31% en protein.

Grp 3. High fat/normal protein diet: provided 11% en carbohydrate, 70% en fat, and 19% en protein.

Grp 4. High carbohydrate diet-pair fed: provided 70% en carbohydrate, 11% en fat, and 19% en protein. Mice in this group were pair-fed calorically to match those in high fat/high protein group 2.

Grp 5. High carbohydrate diet-ad lib: Diet composition was identical to the high carbohydrate-pair fed group 4, but mice in this group were fed ad lib.

The objective of the current study was to investigate the effects of varying dietary carbohydrate, protein, and fat composition on weight gain, plasma lipids, and insulin sensitivity in C57BL/6J mice, a wild type mouse model prone to obesity. Also, whether male and female C57BL/6J mice responded differently to varying macronutrient composition of the diet was studied.

Animals and diet: Male and female C57BL/6J mice (n=44) were initially fed a stabilization diet similar to a typical western diet for 2 weeks. Mice were then fed one of 5 diets (n=4-5 males and 4-5 females/grp) varying in CHO, protein and fat composition as shown in Table 1.

TABLE 1

Composition of diets fed to C57BL/6J mice

| Ingredients | AHA Control | High-fat/high-protein | High-fat/reg protein | High-CHO |
|---|---|---|---|---|
| (CHO:Fat:Protein % en) | (60:21:19) | (11:58:31) | (11:70:19) | (70:11:19) |
| | | g/kg | | |
| Casein | 100 | 213 | 142 | 95 |
| Lactalbumin | 100 | 212 | 141 | 95 |
| Dextrose | 203 | 47 | 52 | 222 |
| Cornstarch | 438 | 101 | 110 | 482 |
| Fat | | | | |
| SFA:MUFA:PUFA (% en) | 7:7:7 | 28:22:8 | 35:26:9 | 5:4:1.3 |
| Butter | 12 | 92 | 124 | 13 |
| Tallow | 40 | 169 | 229 | 24 |
| Lard | — | 55 | 74 | 8 |
| Soybean | 48 | 52 | 70 | 7 |
| Fat/protein % en ratio | 1.1 | 1.9 | 3.7 | 0.6 |
| kcal/g diet | 4.2 | 5.4 | 6 | 4 |
| Mineral mix (Ausman - Hayes) | 46 | 58 | 61 | 42 |
| Vitamin mix (Hayes - Cathcart) | 12 | 15 | 17 | 11 |
| Choline chloride | 3 | 4 | 4 | 3 |
| Cholesterol | 0.73 | 0.57 | 0.5 | 0.7 |

In summary, the AHA control diet provided 60% en carbohydrate, 19% en protein and 21% en fat; the high fat/high protein diet provided 11% en carbohydrate, 31% en protein and 58% en fat; the high fat/regular protein diet provided 11% en carbohydrate, 19% en Protein and 70% en fat; and the high carbohydrate diet-pair fed provided 70% en carbohydrate, 19% en protein and 11% en fat (mice in this group were pair-fed calorically to match those in high fat/high protein group). The high carbohydrate diet-adlib was identical to the high carbohydrate—pair fed group but mice in this group were fed adlib.

Mice were fed the experimental diets for 17 weeks. Body weights were determined weekly during the intervention. Insulin tolerance test was conducted 12 weeks after dietary intervention. Mice were sacrificed after 17 weeks on diets. Blood was collected at the time of sacrifice and plasma lipids were analyzed. Liver, kidney and perirenal adipose tissues were harvested and weights were determined.

Daily estimated caloric and cholesterol intake in mice fed diets varying in macronutrient composition is presented in Table 2. Mice fed AHA, high fat/high protein, high fat/regular protein and high carbohydrate-pair fed mice had similar caloric intake of approximately 13 kcal/d/mouse, while high carbohydrate-adlib fed mice consumed approximately 18 kcal/d/mouse.

TABLE 2

Caloric and cholesterol intakes in C57BL/6J mice fed various CHO/fat/protein diets for 17 wks

| | AHA | High fat/high protein | High fat/reg protein | High CHO-pair fed | High CHO-adlib |
|---|---|---|---|---|---|
| | | Caloric intake (Kcal/mouse/day) | | | |
| Males | 13.5 ± 0.8 | 13.2 ± 0.8 | 12.8 ± 1.0 | 13.1 ± 0.7 | 18.2 ± 1.9 |
| Females | 13.2 ± 0.7 | 12.9 ± 1.0 | 12.9 ± 1.0 | 13.0 ± 0.7 | 18.1 ± 1.7 |
| | | Cholesterol intake (mg/mouse/day) | | | |
| Males | 2.6 | 2.4 | 2.3 | 2.4 | 3.4 |
| Females | 2.5 | 2.4 | 2.4 | 2.4 | 3.4 |

Body and organ weights of male and female C57BL/6J mice are presented in Table 3. In males, mice fed high carbohydrate diet pair-fed to high fat diets (i.e., with similar caloric intake as AHA and high fat fed mice) gained the least weight. Mice fed high fat diet but with regular protein gained more than twice as much weight as high carbohydrate-pair fed mice and significantly more weight than high carbohydrate adlib fed mice, which consumed approx 5Kcal/d more than the high fat/regular protein group. Exchanging fat for Protein (high fat/high Protein group) resulted in lower weight gain. Similar trend was seen with females as well, with high carbohydrate-pair fed mice gaining the least weight and the high fat/regular protein fed mice gaining the highest weight. In females, exchanging fat for protein (high fat/high Protein group) did not lower weight gain as much as in males.

TABLE 3

Body and organ weights in C57BL/6J mice fed diets varying in CHO/fat/protein for 17 wk

|  | AHA | High-fat/ high-protein | High-fat/ reg protein | High-CHO, pair fed | High-CHO, ad lib |
|---|---|---|---|---|---|
| Body weight (g) | | | | | |
| Males | | | | | |
| Initial | 25.3 ± 1.2 | 24.9 ± 1.3 | 25.3 ± 1.1 | 24.7 ± 1.1 | 25.3 ± 1.0 |
| Final | 41.9 ± 2.4$^a$ | 38.8 ± 4.5$^{a,c}$ | 49.1 ± 4.3$^b$ | 35.1 ± 4.9$^c$ | 41.1 ± 3.9$^a$ |
| Wt gain | 16.5 ± 2.7$^a$ | 13.9 ± 3.6$^{a,c}$ | 23.8 ± 3.9$^b$ | 10.4 ± 4.8$^c$ | 15.8 ± 3$^a$ |
| Females | | | | | |
| Initial | 20.5 ± 1.6 | 21.2 ± 1.1 | 20.6 ± 1.5 | 21.1 ± 1.7 | 21.3 ± 1.8 |
| Final | 30.1 ± 1.9$^a$ | 34.0 ± 2.8$^{a,b}$ | 34.3 ± 2.9$^b$ | 30.4 ± 3.6$^a$ | 34.5 ± 2.3$^b$ |
| Organ weights (% body weight) | | | | | |
| Males | | | | | |
| Liver | 3.8 ± 0.6$^{a,b}$ | 2.7 ± 0.2$^a$ | 3.2 ± 0.8$^{a,b}$ | 4.1 ± 1.4$^b$ | 4.5 ± 1.3$^b$ |
| Kidney | 1.1 ± 0.03$^{a,b}$ | 1.3 ± 0.2$^a$ | 1.0 ± 0.1$^b$ | 1.3 ± 0.4$^a$ | 1.1 ± 0.2$^{a,b}$ |
| Perirenal adipose | 2.8 ± 0.2$^{a,b}$ | 2.3 ± 0.5$^{a,d}$ | 3.4 ± 0.2$^b$ | 1.7 ± 0.7$^c$ | 2.1 ± 0.2$^{c,d}$ |
| Females | | | | | |
| Liver | 3.9 ± 0.5$^a$ | 2.9 ± 0.2$^b$ | 2.9 ± 0.3$^b$ | 4.4 ± 0.3$^c$ | 4.5 ± 0.2$^c$ |
| Kidney | 1.2 ± 0.2 | 1.0 ± 0.01 | 1.0 ± 0.14 | 1.1 ± 0.03 | 0.9 ± 0.06 |
| Perirenal adipose | 2.7 ± 0.6$^a$ | 3.3 ± 0.8$^{a,b}$ | 4.0 ± 1.2$^b$ | 2.8 ± 0.5$^{a,b}$ | 3.2 ± 0.7$^{a,b}$ |

$^{a,b,c,d}$Means in a row with different superscripts differ (p < 0.05) by one-way ANOVA and Fisher's PLSD test Liver weight (as % body weight) was highest in high carbohydrate pair fed and adlib fed male and female mice. In males, kidney weights were higher in high fat/high protein group and high CHO-pair fed group compared to high fat/regular protein group. Perirenal adiposity was highest in the male and female mice fed high fat/regular protein diet.

Fasting plasma total cholesterol and triglycerides are shown in Table 4. In males, plasma total cholesterol was not significantly different among groups. However, mice fed high fat/high protein diet had the least increase in plasma total cholesterol from baseline compared to mice fed AHA, high fat, and high carbohydrate diets. In females, high fat/high protein diet resulted in the most decrease in plasma total cholesterol from baseline. Mice fed high carbohydrate diets (both pair-fed and adlib fed) had significantly greater plasma total cholesterol after 17 weeks of intervention compared to high fat/high protein and high fat/regular protein diets. The plasma triglycerides change from baseline was similar in all groups. In females, surprisingly, the high-carbohydrate-pair fed mice had significantly higher plasma triglycerides than high carbohydrate ad lib fed mice.

TABLE 4

Fasting plasma TOTAL CHOLESTEROL and TRIGLYCERIDES at baseline and after 17 wks on diets varying in CHO/fat/protein composition

|  | AHA | High-fat/high-protein | High-fat/reg protein | High-CHO, pair fed | High-CHO, adlib |
|---|---|---|---|---|---|
| Plasma TOTAL CHOLESTEROL (mg/dL) | | | | | |
| Males | | | | | |
| Baseline | 138 ± 11 | 123 ± 34 | 141 ± 6 | 116 ± 36 | 138 ± 41 |
| 17 wks | 207 ± 27 | 141 ± 39 | 185 ± 40 | 161 ± 85 | 177 ± 71 |
| % Change | 69 | 18 | 44 | 45 | 39 |
| Females | | | | | |
| Baseline | 112 ± 29 | 125 ± 6 | 110 ± 25 | 132 ± 9 | 111 ± 28 |
| 17 wks | 106 ± 25$^{a,c}$ | 102 ± 7$^a$ | 100 ± 12$^a$ | 132 ± 6$^b$ | 124 ± 12$^{b,c}$ |
| % Change | −6 | −23 | −10 | −0.2 | 13 |
| Plasma TRIGLYCERIDES (mg/dL) | | | | | |
| Males | | | | | |
| Baseline | 137 ± 11$^a$ | 112 ± 29$^b$ | 87 ± 10$^c$ | 55 ± 14$^c$ | 64 ± 9$^d$ |
| 17 wks | 138 ± 22$^a$ | 119 ± 45$^{a,c}$ | 97 ± 11$^{b,d}$ | 62 ± 16$^c$ | 72 ± 10$^{c,d}$ |
| % Change | 1 | 7 | 10 | 7 | 8 |
| Females | | | | | |
| Baseline | 73 ± 34 | 85 ± 13 | 71 ± 18 | 89 ± 13 | 75 ± 17 |
| 17 wks | 67 ± 27$^a$ | 86 ± 4$^{a,b}$ | 78 ± 18$^{a,b}$ | 114 ± 46$^b$ | 59 ± 10$^a$ |
| % Change | −6 | 1 | 7 | 25 | −16 |

$^{a,b,c,d}$Means in a row with different superscripts differ (p < 0.05) by one-way ANOVA and Fisher's PLSD test Liver lipid data in male mice are shown in Table 5.

TABLE 5

Liver lipids in C57BL/6J mice fed diets varying in CHO/fat/protein composition for 17 wks

| | AHA | High fat/ high prot | High fat/ reg prot | High CHO, pair fed | High CHO, ad lib |
|---|---|---|---|---|---|
| | | | Liver lipids, mg/g Males | | |
| FC | $2.8 \pm 0.3^a$ | $3.8 \pm 1.1^{a,b}$ | $3.3 \pm 0.4^a$ | $4.1 \pm 0.4^b$ | $3.5 \pm 0.3^{a,b}$ |
| EC | $4.8 \pm 1.4^a$ | $1.1 \pm 0.5^b$ | $1.2 \pm 0.3^b$ | $11.2 \pm 3.7^c$ | $11.3 \pm 4.6^c$ |
| TC | $7.6 \pm 1.7^a$ | $4.9 \pm 1.6^a$ | $4.5 \pm 0.5^a$ | $15.2 \pm 3.6^b$ | $14.8 \pm 4.8^b$ |

Figure 7:
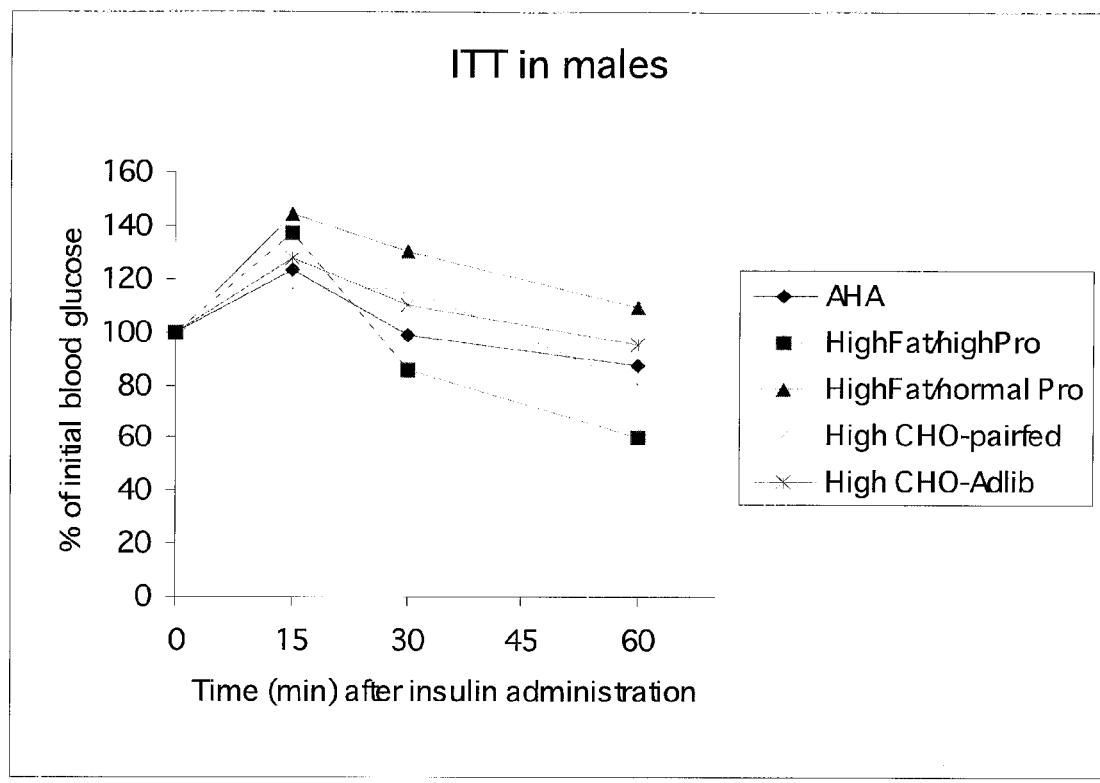
FIG. 7 graphically illustrates ITT in males.
Figure 8:
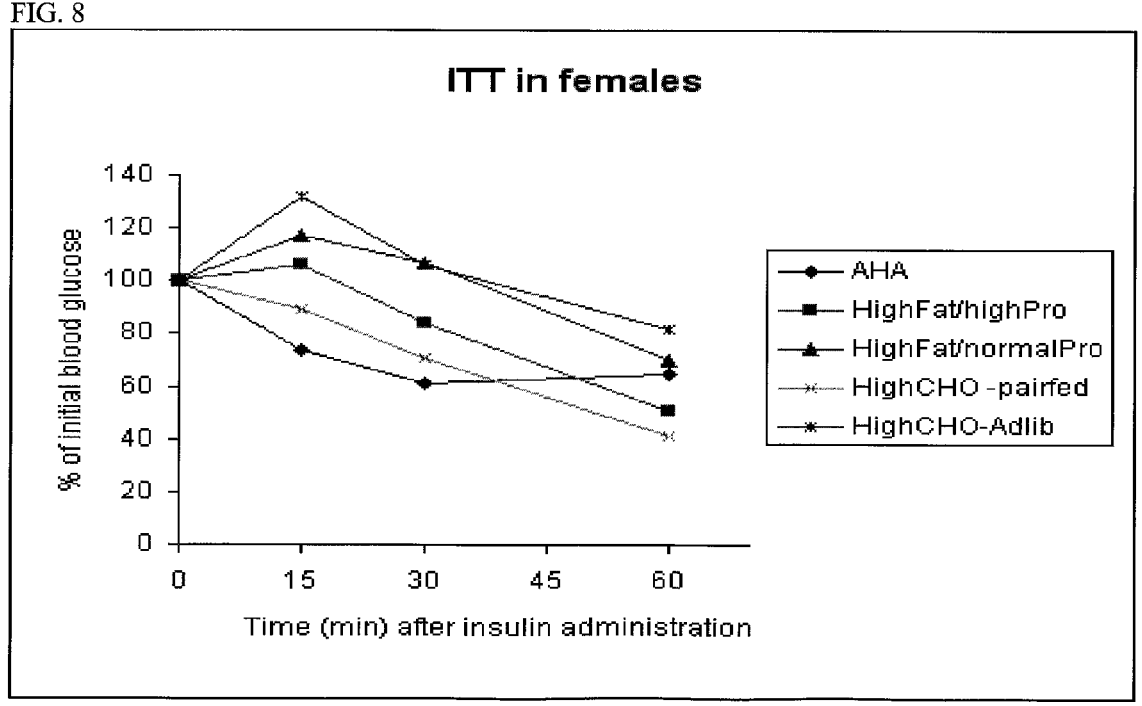
FIG. 8 graphically illustrates ITT in females.

$^{a,b,c}$Means in a row with different superscripts differ ($p < 0.05$) by one-way ANOVA and Fisher's PLSD test ITT data for males and females are presented in FIGS. 7-8, respectively. In males, the high fat/regular protein fed mice tended to have elevated blood glucose at 30 and 60 min following insulin administration compared to other diets, especially the high fat-high protein diet. In females, high carbohydrate—ad lib fed mice and high fat/regular protein mice had elevated blood glucose 30 and 60 min following insulin administration. Thus, the data suggests that high fat intake or higher caloric intake may induce insulin resistance.

Figure 9:
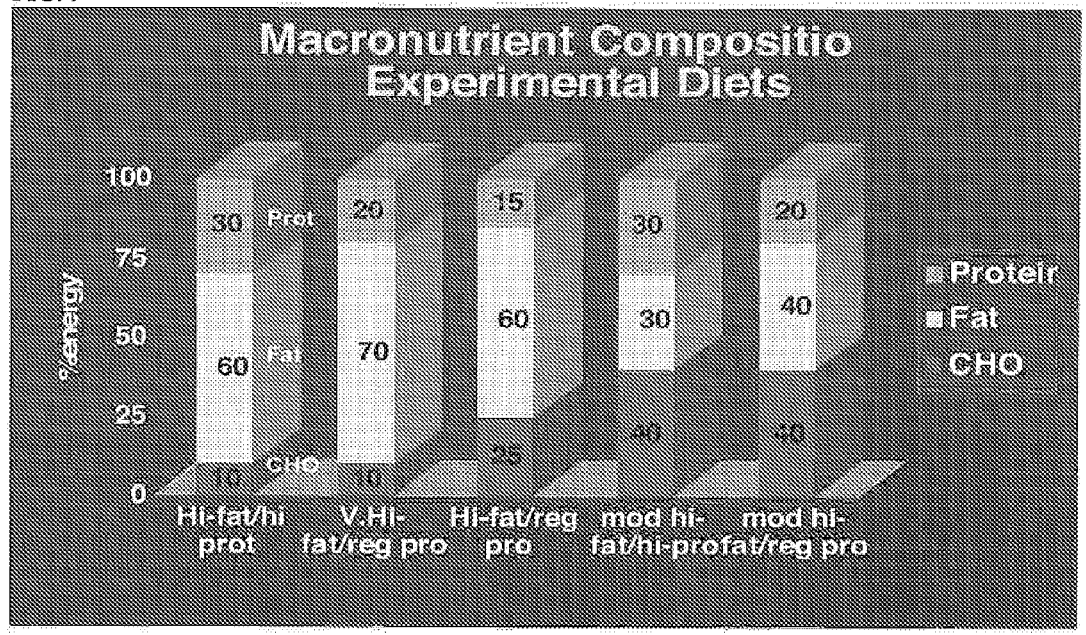
FIG. 9 graphically illustrates macronutrient composition experimental diets.
Figure 10:
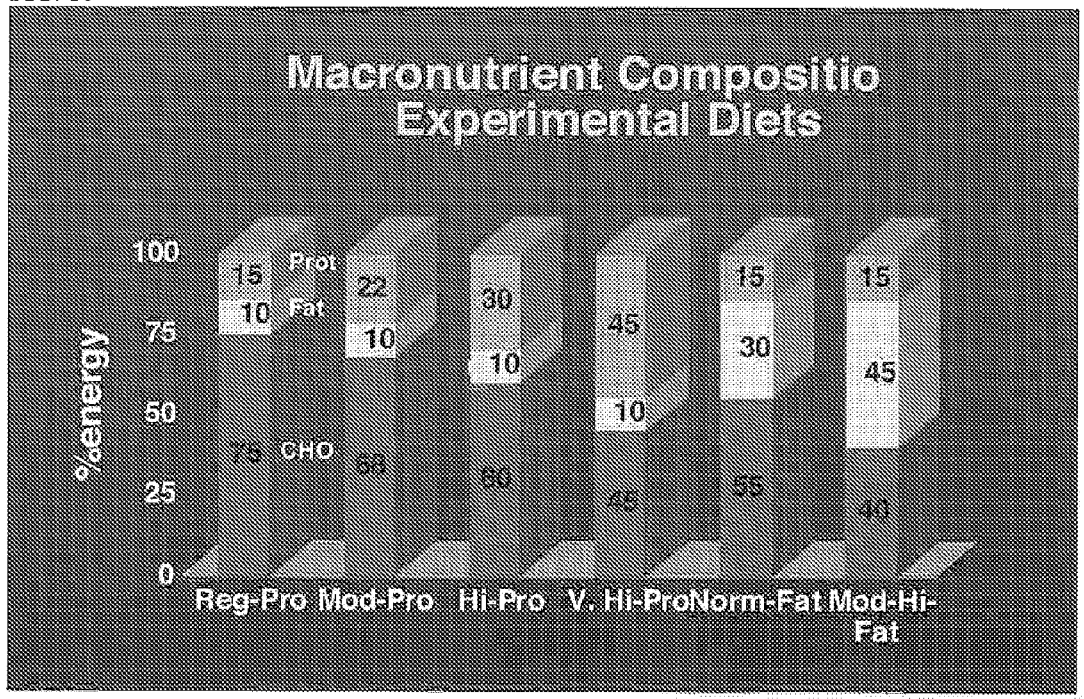
FIG. 10 graphically illustrates macronutrient composition experimental diets.

For purposes of easy comparison, the ratios of carbohydrate, fat, and protein in various diets used throughout these studies are shown in FIGS. 9-10.

Figure 11:
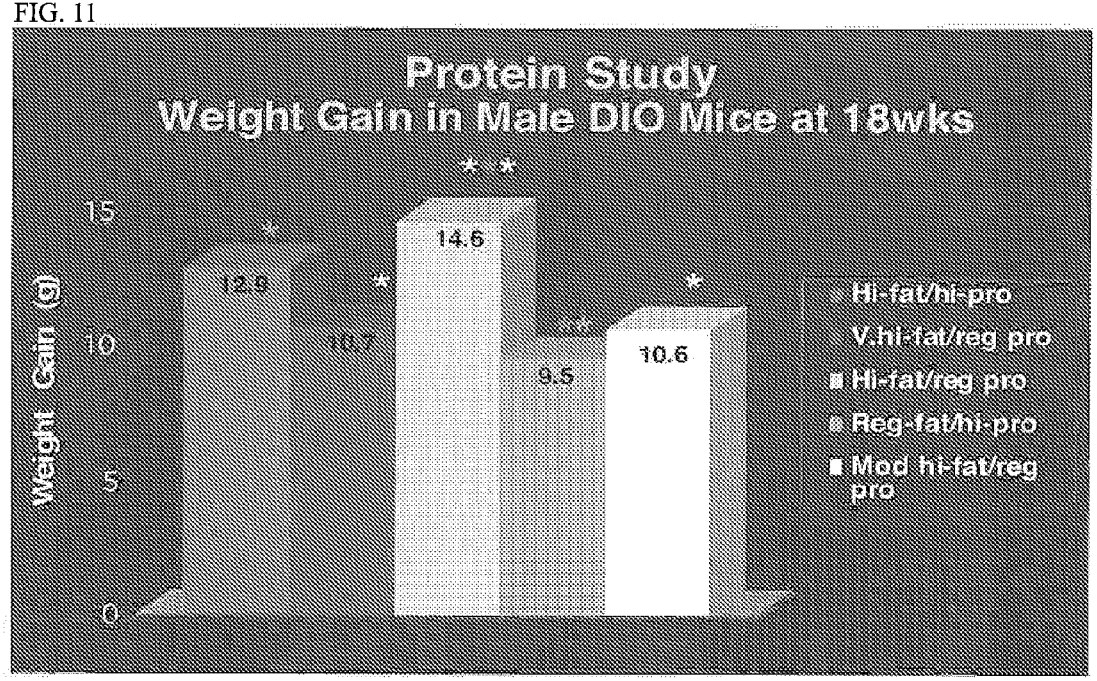
FIG. 11 graphically illustrates protein study weight gain in male DIO mice at 18 weeks.
Figure 12:
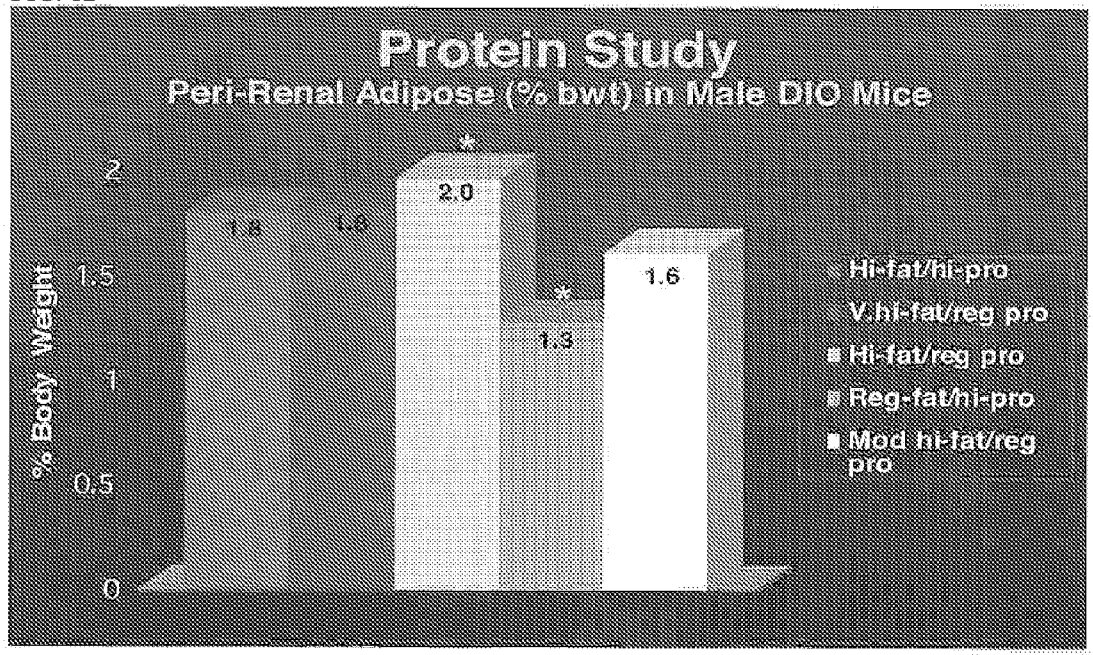
FIG. 12 graphically illustrates protein study peri-renal adipose in male DIO mice.

Body weight gain and adiposity: The effects of carbohydrate, fat and protein composition of diet on body weight gain and insulin sensitivity was studied in C57BL/6J male and female mice. Results are shown in FIGS. 11-12.

Mice on high carbohydrate diets consumed significantly more calories per day compared to those on high fat diets. In order to control differences in body weight gain that may result from varying caloric intake, one group of mice on high carbohydrate diet were pair-fed to those on high fat diet/high protein in this study. Changes in macronutrient composition had a significant impact on body weight gain and adiposity in this wild type mice model, especially in males. The high fat diet providing 70% en fat and 19% en protein induced higher body weight gain and adiposity compared to AHA control, high fat/high protein and high carbohydrate diets, even when caloric intake was lower compared to high carbohydrate ad lib fed mice. Enhanced lipogenesis by high fat intake may have resulted in increased adiposity and body weight gain.

Figure 13:
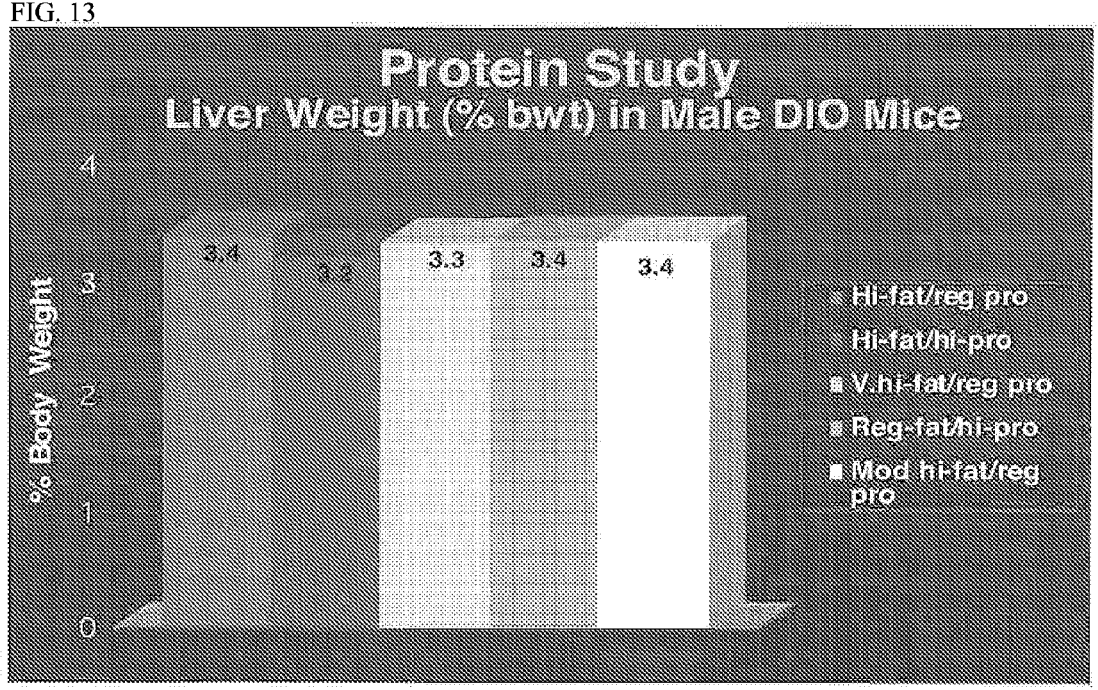
FIG. 13 graphically illustrates protein study liver weight in male DIO mice.

High fat intake may alter hepatic lipogenic enzymes and/or adipose hormones such as leptin, ASP, and adiponectin, which are all implicated in lipid synthesis and storage in adipose. See FIG. 13. High fat intake at low carbohydrate intake has been reported to increase lipolysis and fatty acid oxidation. However, dietary fat up-regulation of fatty acid oxidation is reported to be limited. Thus, energy imbalance resulting from increased lipid synthesis/storage and limited lipolysis and fatty acid oxidation may have resulted in increased body weight. High fat/high protein diet fed mice (58% en fat and 31% en Pro) however had significantly lower weight gain than high fat (70% en fat) fed mice. Thus, increasing the protein content of the diet in exchange for fat prevented body weight gain and adiposity. But when caloric intake was restricted, high carbohydrate diet led to lowest weight gain in the wild type mouse model in this study.

Figure 14:
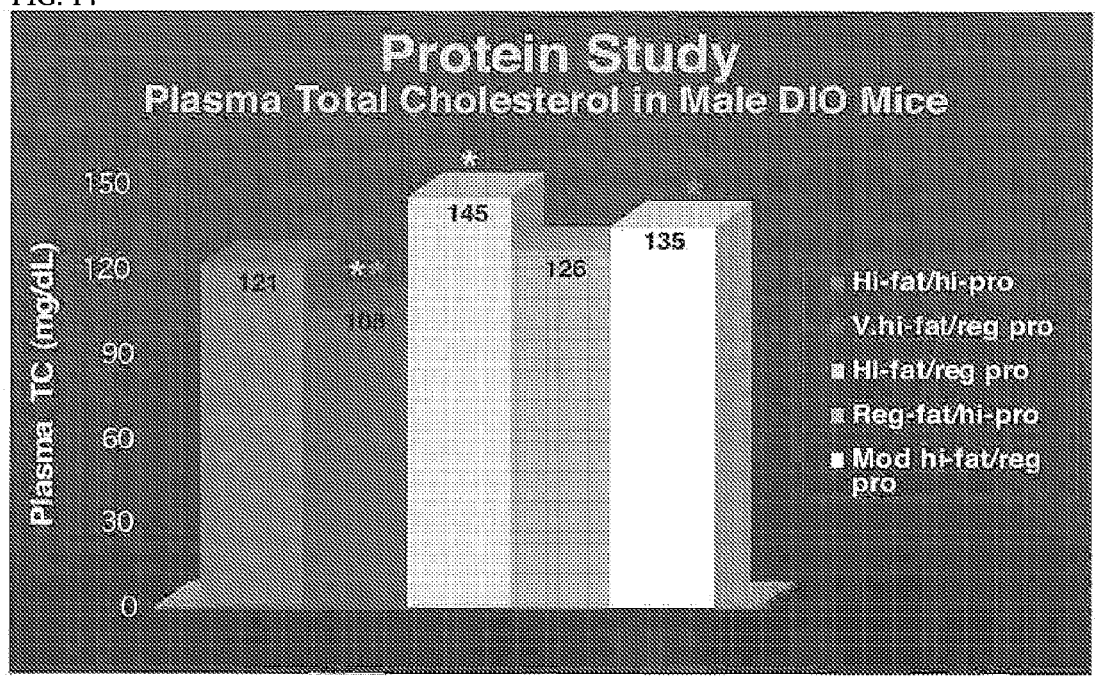
FIG. 14 graphically illustrates protein study plasma total cholesterol in male DIO mice.
Figure 15:
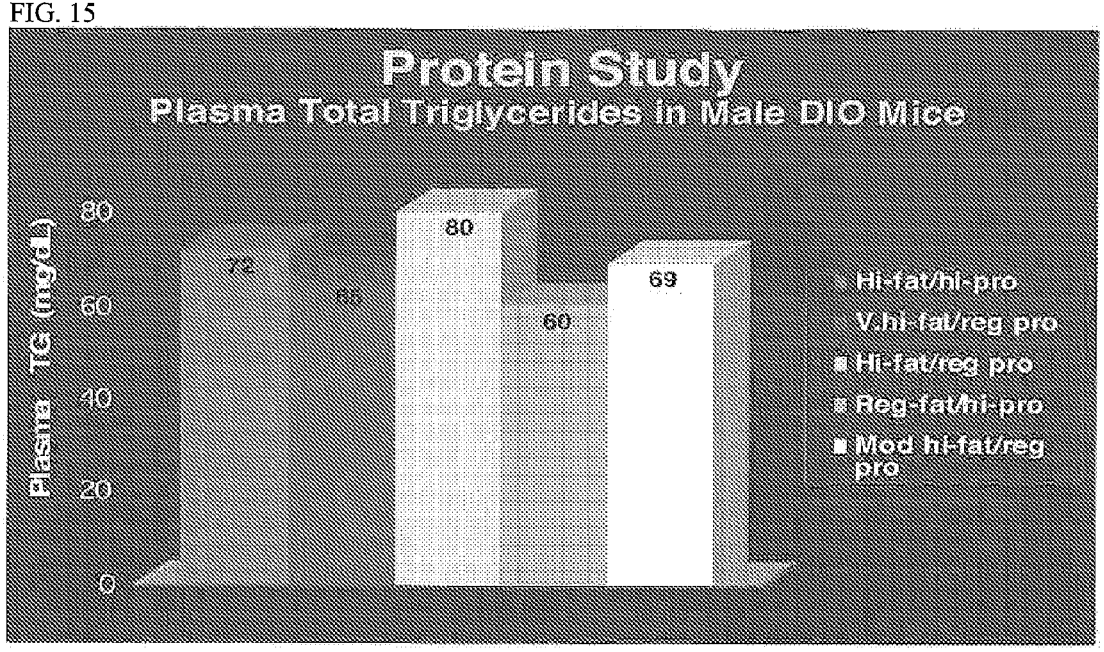
FIG. 15 graphically illustrates protein study plasma total triglycerides in male DIO mice.

Plasma Lipids: The high carbohydrate diets elevated plasma TC, especially in females. High carbohydrate intake may have increased hepatic VLDL secretion which may have led to increased plasma TC. Plasma cholesterol clearance could also have been impaired by high carbohydrate diets. The high fat/high protein diet tended to have the most favorable change in plasma total cholesterol from baseline. Recent human studies have also reported that very low carbohydrate diets high in fat and protein either decreased or failed to change plasma TC. Thus, from a cardiovascular disease (CVD) risk point, diet high in fat and protein did not appear to be detrimental. See FIGS. 14-15.

Insulin sensitivity: High fat (70% en fat) diet fed mice and high carbohydrate adlib fed mice tended to have impaired glucose clearance in response to exogenous insulin administration. Insulin resistance in the high fat fed mice is likely secondary to increased adiposity and body weight. High fat/ high protein mice were similar to AHA controls in their blood glucose response to insulin. Thus, addition of protein to a diet high in fat appeared to improve insulin sensitivity.

In conclusion, a high fat diet induced weight gain, adiposity, and insulin resistance in the wild type C57BL/6J mice. Thus a high fat diet may predispose individuals to metabolic syndrome. High carbohydrate diet did not increase weight gain, but mice fed high carbohydrate diets consumed more calories and had elevated plasma TC, especially in females. The high fat/high protein diet in which fat was exchanged for protein resulted in lower weight gain, lower adiposity, and improved insulin sensitivity compared to the high fat diet. Thus, present study suggests that the ratio of fat to protein may be an important factor regulating energy balance, adiposity, and obesity.

Data from these Wild Type C57BL/6J mice, the so-called Dietary Induced Obesity (DIO) model, make several points:
1. The high fat/normal protein diet in Group3 (70% en fat, 19% en prot) resulted in highest weight gain and adiposity compared to either AHA or high carbohydrate, pair fed diets. Adding protein to high fat diet in exchange for dietary fat (high fat/high protein, Group2) lowered weight gain and adiposity comparable to AHA and high Carbohydrate diets, especially in males. This suggests that either extra protein or reduced fat had a favorable impact on obesity in an environment where the fat was overabundant. Maybe all 3 macronutrients are important and delicately balanced. Presumably the quality of each also plays a role. This fat/protein ratio may represent a key observation for weight control diets.
2. Liver EC was 10 times higher for high carbohydrate (Ornish) diets compared to high fat/high protein and high fat/regular protein (Grp2+3) in males. Thus, even when caloric and dietary cholesterol intake was similar (unlike Study 6 where kcal and cholesterol intake were poorly controlled), high carbohydrate diets dramatically increased liver EC compared to high fat/high protein diet.
3. The high fat/high protein Atkins diet lowered plasma total cholesterol compared to other diets. In females, high carbohydrate diet elevated plasma total cholesterol compared to other diets.
4. The high fat/normal protein diet (Group 3 male and female) mice and high CHO-ad lib fed female mice (Group 5) had impaired insulin sensitivity compared to the other 3 diets (Control, high fat/high protein, pair fed carbohydrate). Thus, high fat intake and/or high caloric intake, in general, may impair insulin action and induce insulin resistance. This is would be expected from the literature in all species, including humans.

Thus, the high fat diet providing 70% en as fat (and normal protein) induced obesity, with increased adiposity and insulin resistance in both male and female C57BL/6J mice. This is typical of the American diet and suggests this model could be used in future studies to explore dietary aspects of the metabolic syndrome. In addition, combined data from Study 6 and Study 10 show that differences in macronutrient composition, rather than variation in dietary cholesterol intake, accounted for the major changes in hepatic and plasma lipids (much like current thinking on human experience). In the apoE (−/−) mice in Study 6, hepatic EC and aortic EC (atherosclerosis) was greater in high carbohydrate (Ornish) mice compared to high fat/high protein (Atkins) mice but the former had higher food and cholesterol intake, as well. But in Study 10 with WT C57BL/6J mice, where caloric and cholesterol intakes were similar, high carbohydrate diet (Ornish pair fed, Group 4) still accumulated more liver EC compared to high fat/high protein diet (true Atkins, Group2). Furthermore, the increase in hepatic EC induced by high carbohydrate diet in the Wild Type C57BL/6J mice was much more dramatic (Study 10) than that seen in apoE (−/−) mice (Study 6). Further, in Study 10, high CHO, pair fed and ad lib fed mice had very similar liver EC mass, even though cholesterol intake in ad lib fed mice was higher (2.4 vs 3.4 mg/d/mouse), indicating that the high carbohydrate content of the diet and not the cholesterol intake was the primary factor driving hepatic EC accumulation. Most likely, since carbohydrate drives fatty acid and cholesterol synthesis in the liver, extra carbohydrate provides substrate for ACAT-dependant 18:1 esterification of hepatic cholesterol and greater liver cholesterol secretion. High protein, high fat intake would exclude this carbohydrate effect, since fat is delivered directly to the blood and bypasses the liver.

High fat/normal protein diets increase weight gain and adiposity compared to high carbohydrate diets. However, increasing the level of protein in exchange for dietary fat lowers weight gain and adiposity compared to the diets high carbohydrates. Thus, the increased protein and reduced fat had a favorable impact on reducing obesity. The ratio of protein to fat may be a key for weight control diets. Insulin sensitivity was improved with high fat/high protein diets compared to high fat/normal protein and high carbohydrate diets. Thus, high fat intake may impair insulin sensitivity and induce insulin resistance. Both high fat and high carbohydrate diets have drawbacks and the important variable may be the concomitant protein intake. Liver cholesterol was higher in the high carbohydrate diets compared to the high fat/high protein and high fat/normal protein diets. Plasma total cholesterol was decreased with high fat/high protein diets compared to the high carbohydrate diets, which increased plasma total cholesterol.

Study 11

This study examined the influence of soluble fiber at two fat intakes on the lipid and insulin sensitivity responses in WT C57BL (DIO) mice. Three diets were fed. Diet 1 was the "semi-Ornish", low-fat control with no sucrose, and pectin added generously at 6%. Diet 2 represented the AM FAT load at 40% en, but balanced fat with its S:M:P ratio, again with pectin at 6% but the carbohydrate as cornstarch and no sucrose. Finally, Diet 3 removed the pectin and replaced half the carbohydrate with sucrose. The bottom line here was that Diet 3 induced modest "obesity", modest cholesterol elevation, and the least attractive OGTT and ITT. This suggests again that the (male) DIO mouse represents a nice model of diet-induced obesity, including sensitivity to several nuances of diet such as carbohydrate type, fat load and the fat:protein ratio, cholesterol load, and, in this study, the level of soluble pectin.

Study 12

C57BL (obese mouse model) mice were randomized to one of the 5 diets in FIG. 9: 1) high fat/regular protein diet (ratio 4:1; 25% CHO, 15% protein, 60% fat); 2) high fat/high protein diet (ratio 2:1; 10% CHO, 30% protein, 60% fat); 3) very high fat/regular protein (ratio 3.5:1; 10% CHO, 20% protein, 70% fat); 4) regular fat/high protein (ratio 1:1; 40% CHO, 30% protein, 30% fat); and 5) moderate high fat/regular protein (ratio 2:1; 40% CHO, 20% protein, 40% fat). Details of the composition of each diet are shown in Table 6, below.

TABLE 6

C57BL/6J mouse study diets with protein replacing fat at different fat levels (% en)

| | gram per 1.0 kilo | | | | |
|---|---|---|---|---|---|
| INGREDIENT | High-fat/ reg pro | High-fat/ high-pro | V.high-fat/ reg pro | Reg-fat/ high pro | mod high-fat/reg pro |
| (CHO:Fat:Protein % en ratio) | (25:60:15) | (10:60:30) | (10:70:20) | (40:30:30) | (40:40:20) |
| Casein | 106 | 213 | 142 | 175 | 115 |
| Lactalbumin | 106 | 212 | 141 | 175 | 115 |
| Dextrose | 115 | 47 | 52 | 140 | 154 |
| Cornstarch | 246 | 101 | 111 | 298 | 323 |
| Fat: | | | | | |
| Butter | 92 | 92 | 124 | 39 | 60 |
| Tallow | 169 | 169 | 229 | 72 | 109 |
| Lard | 55 | 55 | 74 | 24 | 36 |
| Soybean | 52 | 52 | 70 | 23 | 34 |
| Mineral mix (Ausman-Hayes) | 58 | 58 | 61 | 47 | 50 |
| Vitamin mix (Hayes-Cathcart) | 15 | 15 | 17 | 12 | 13 |
| Choline chloride | 4 | 4 | 4 | 3 | 3 |
| Cholesterol (added) | 0.57 | 0.57 | 0.5 | 0.68 | 0.64 |
| Total cholesterol in diet* | 1.01 | 1.01 | 1.1 | 0.85 | 0.9 |

Figure 16:
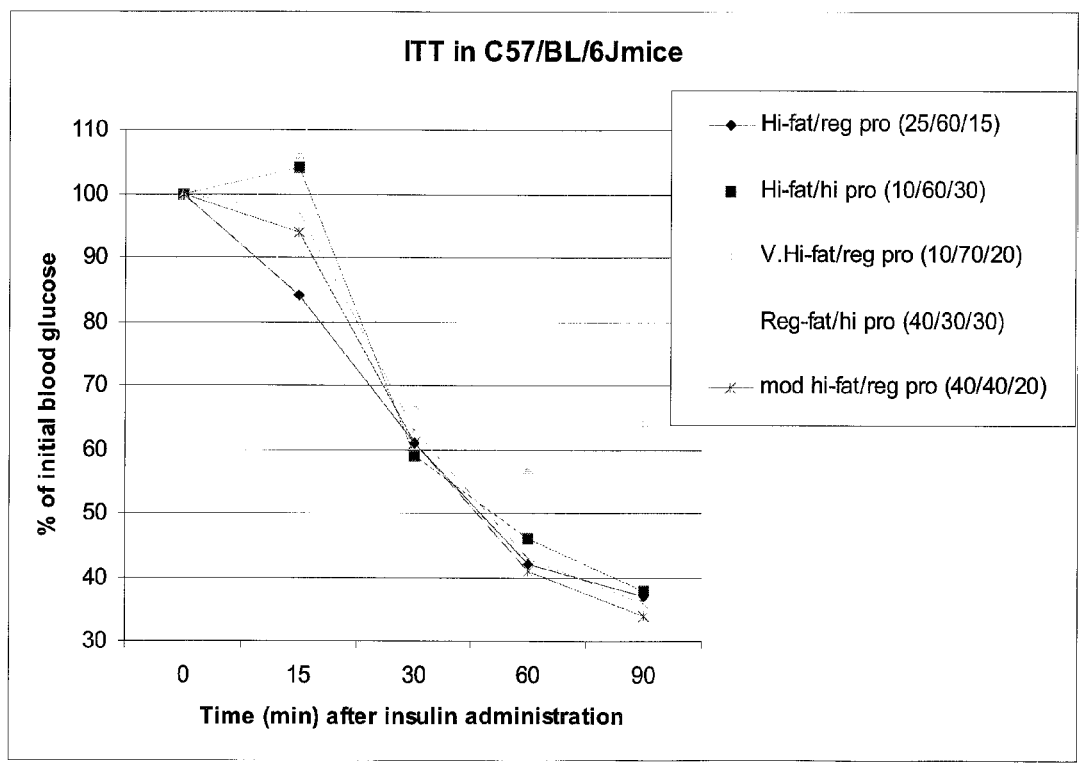
FIG. 16 graphically illustrates ITT in C57/BL/6J mice.
Figure 17:
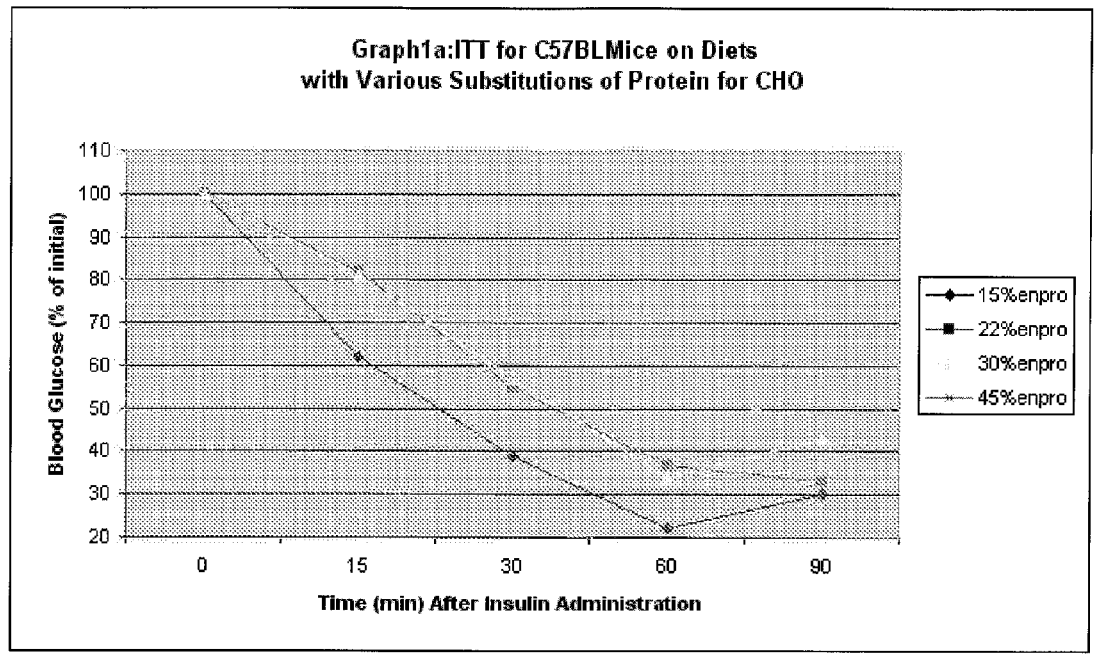
FIG. 17 graphically illustrates ITT for C57BL mice on diets with various substitutions of proteins for CHO.
Figure 18:
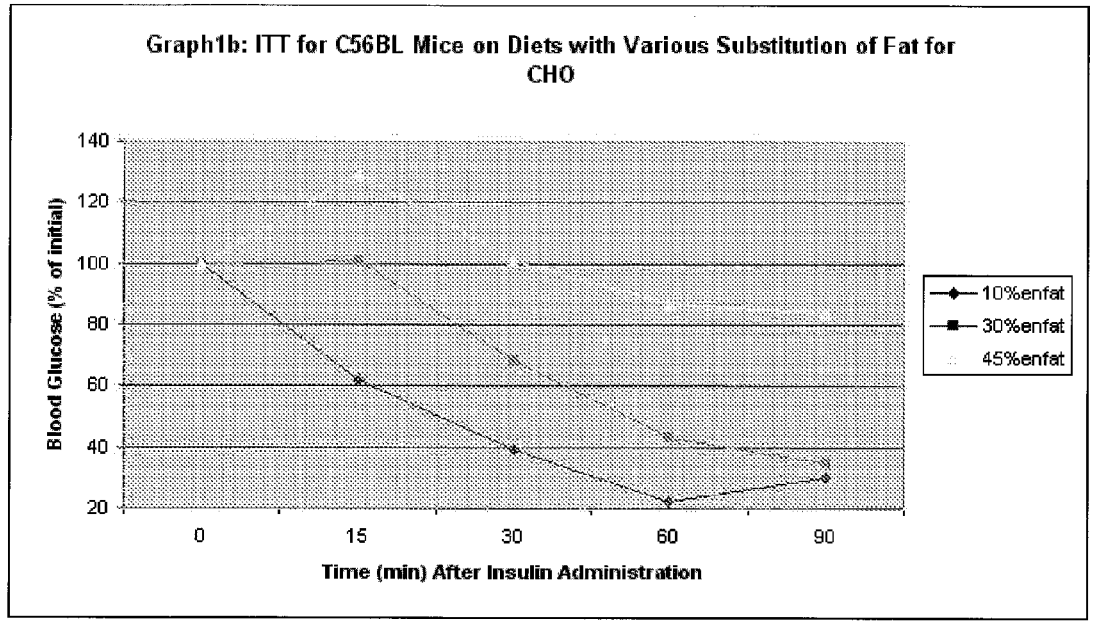
FIG. 18 graphically illustrates ITT for C56BL mice on diets with various substitution of fat for CHO.
Figure 19:
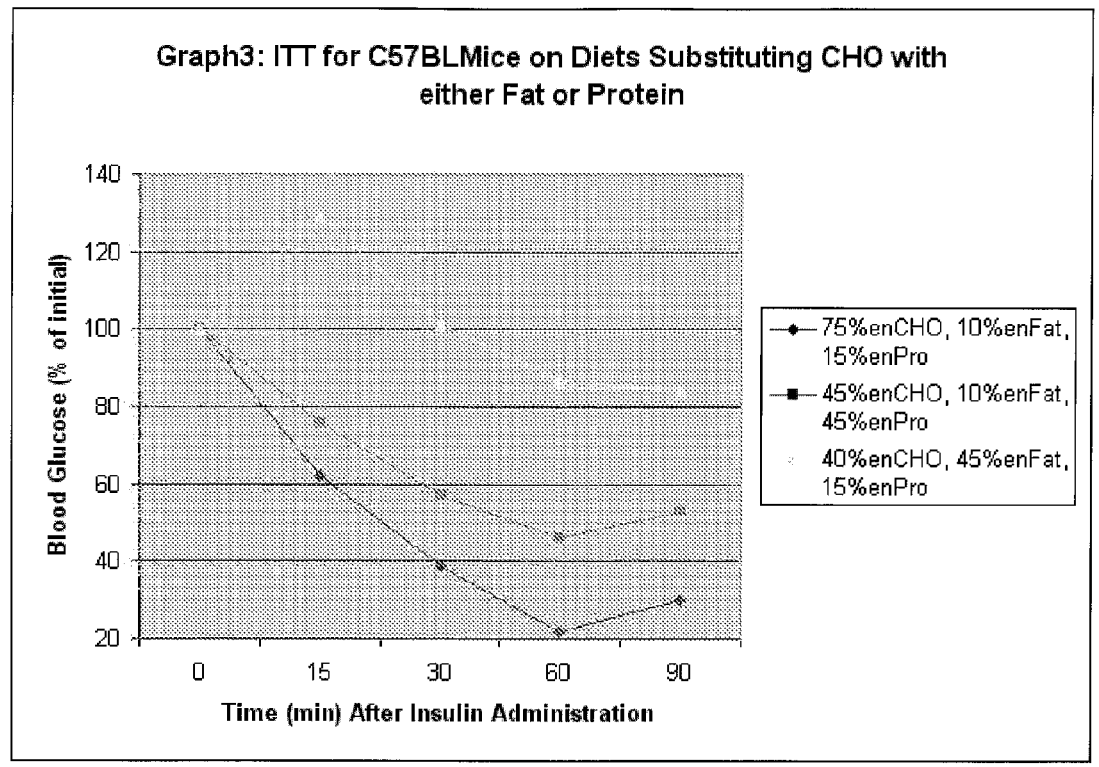
FIG. 19 graphically illustrates ITT for C57BL mice on diets substituting CHO with either fat or protein.
Figure 20:
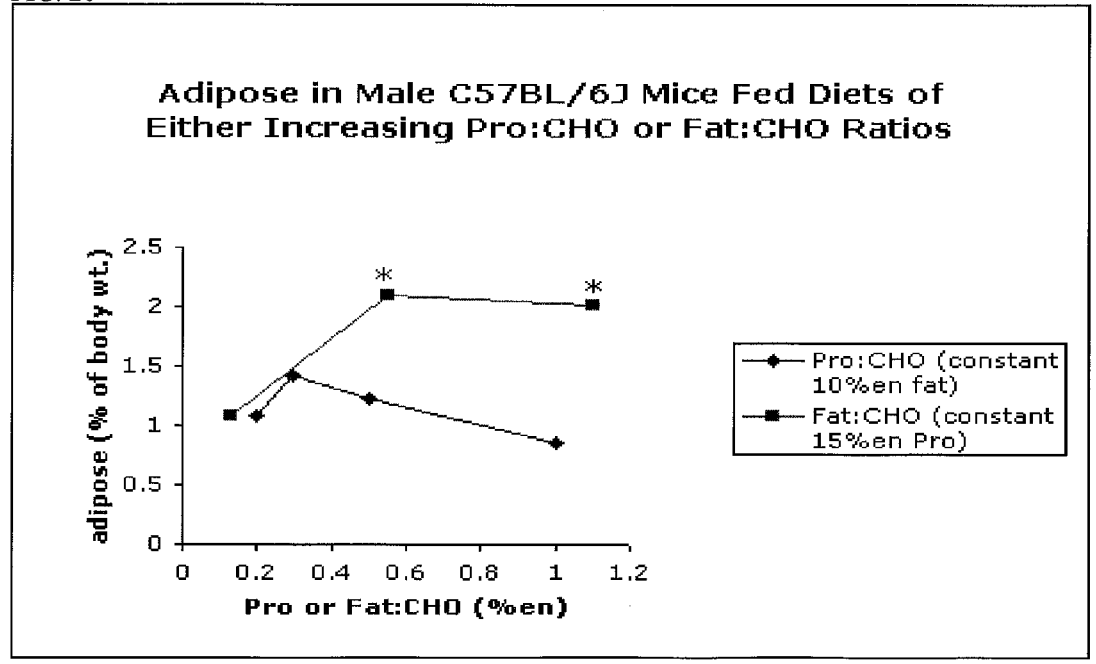
FIG. 20 graphically illustrates adipose in male C57BL/6J mice fed diets of either increasing Pro:CHO or fat:CHO ratios.
Figure 21:
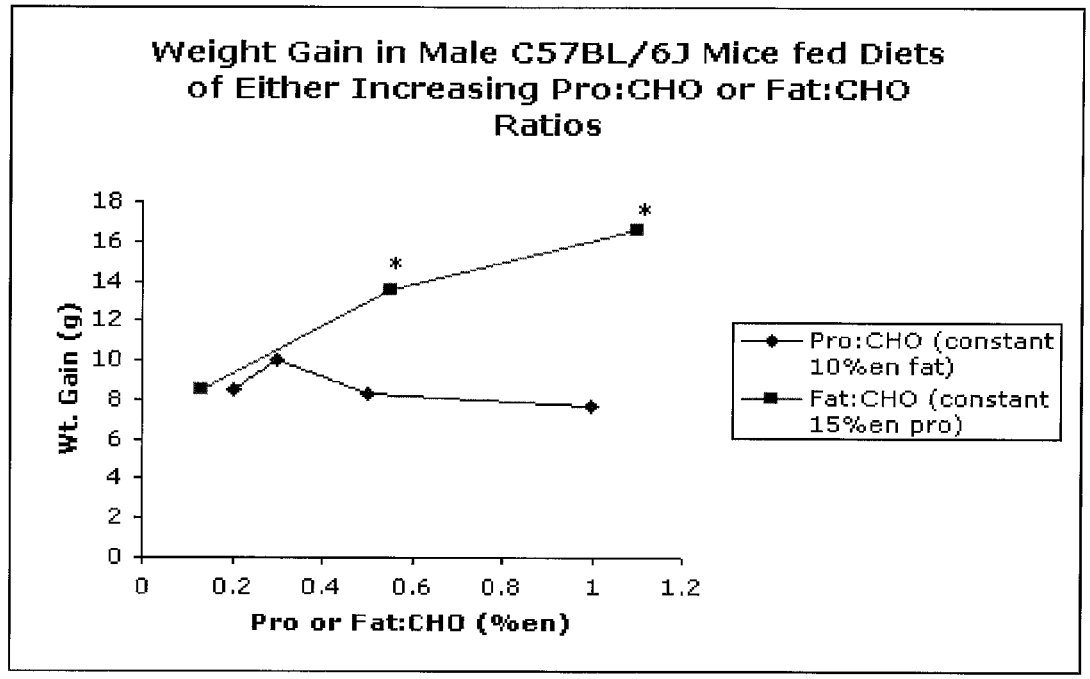
FIG. 21 graphically illustrates weight gain in male C57BL/6J mice fed diets of either increasing Pro:CHO or Fat:CHO ratios.
Figure 22:
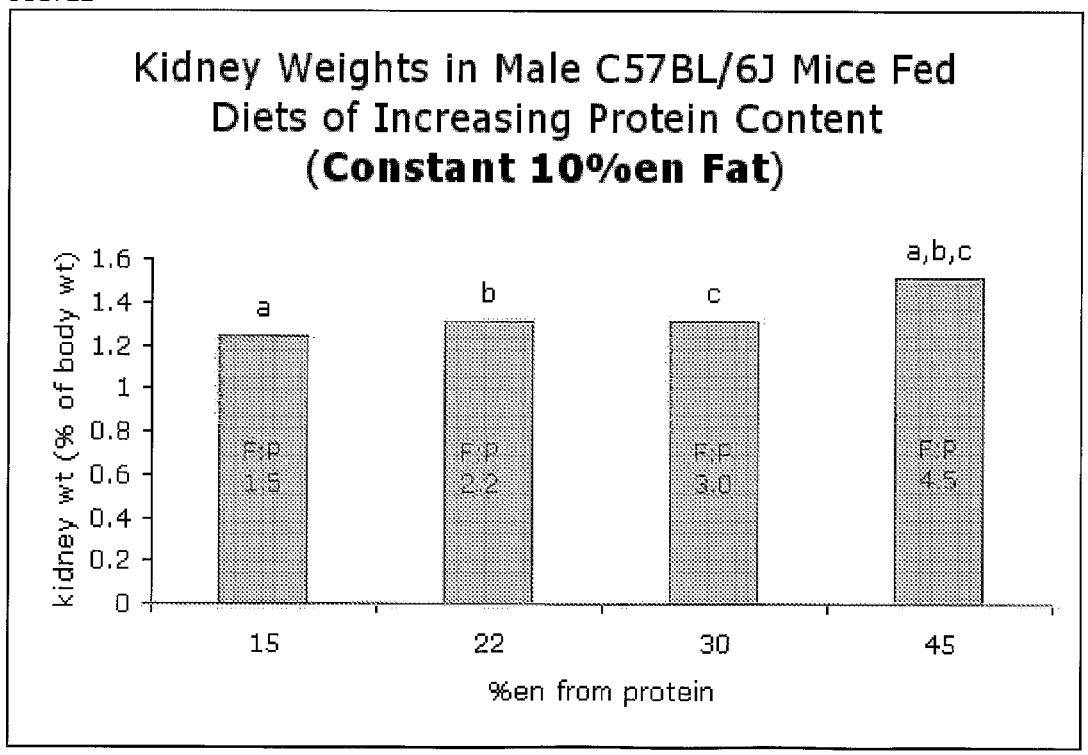
FIG. 22 graphically illustrates kidney weights in male C57BL/6J mice fed diets of increasing protein content.
Figure 23:
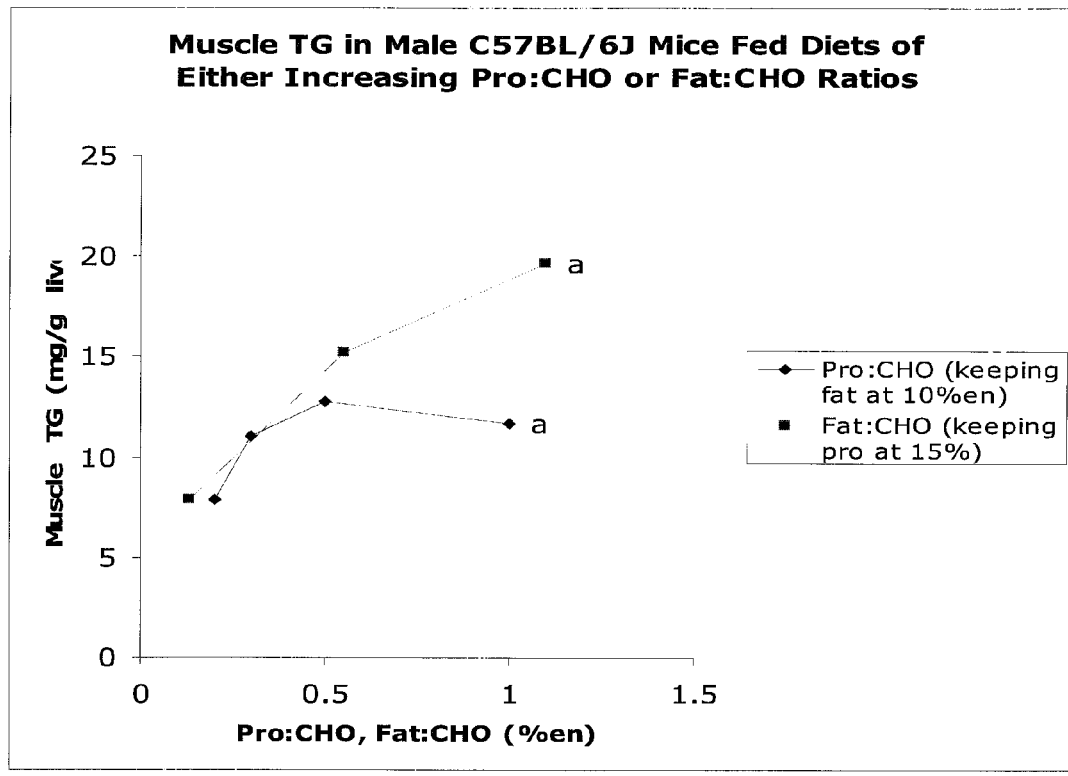
FIG. 23 graphically illustrates muscle TG in male C57BL/6J mice fed diets of either increasing Pro:CHO or Fat:CRO ratios.
Figure 24:
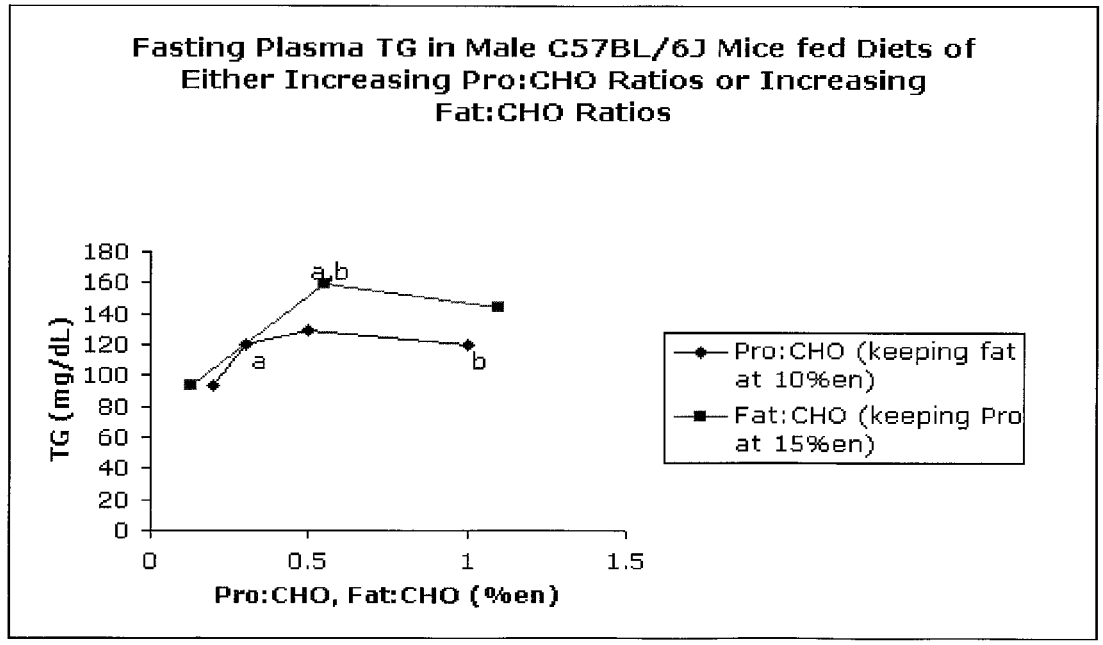
FIG. 24 graphically illustrates fasting plasma TG in male C57BL/6J mice fed diets of either increasing Pro:CHO ratios or increasing Fat:CHO ratios.
Figure 25:
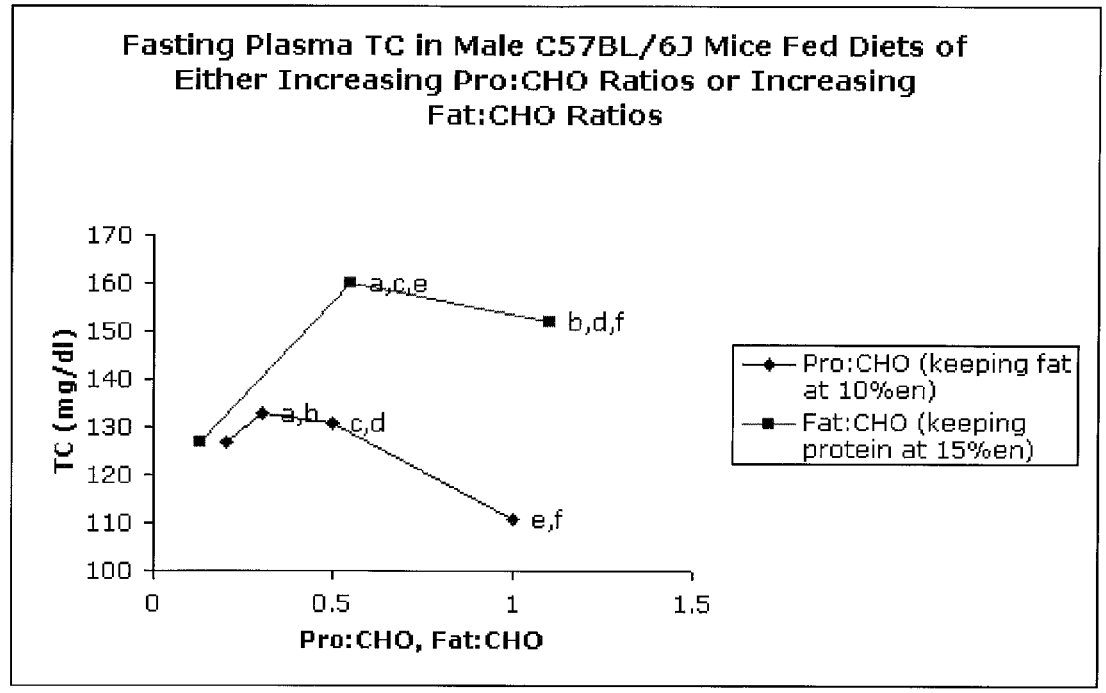
FIG. 25 graphically illustrates fasting plasma TC in male C57BL/6J mice fed diets of either increasing Pro:CHO ratios or increasing Fat:CRO ratios.
Figure 26:
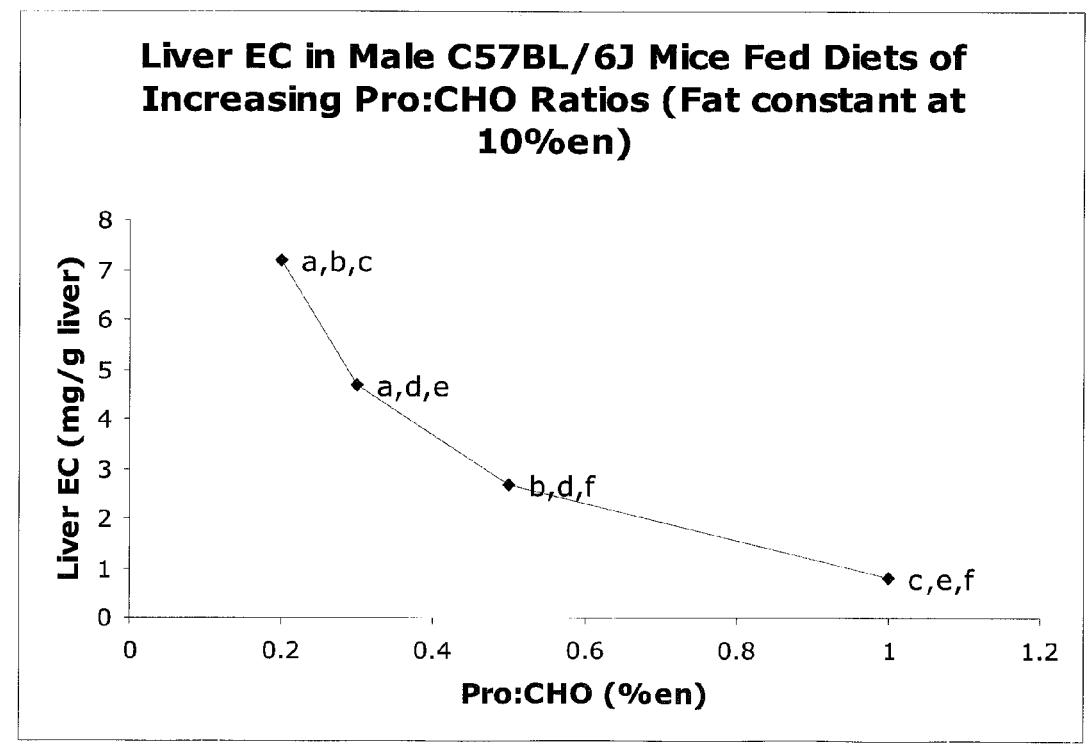
FIG. 26 graphically illustrates liver EC in male C57BL/6J mice fed diets of increasing Pro:CRO ratios.
Figure 27:
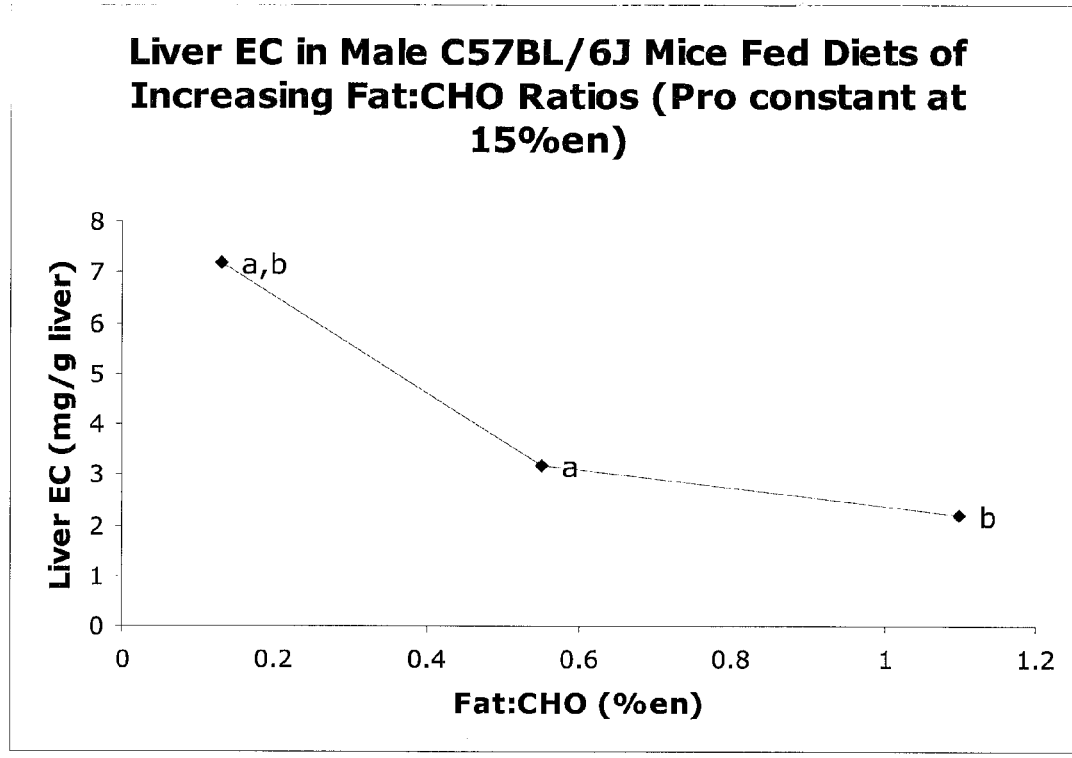
FIG. 27 graphically illustrates liver EC in male C57BL/6J mice fed diets of increasing Fat:CHO ratios.
Figure 28:
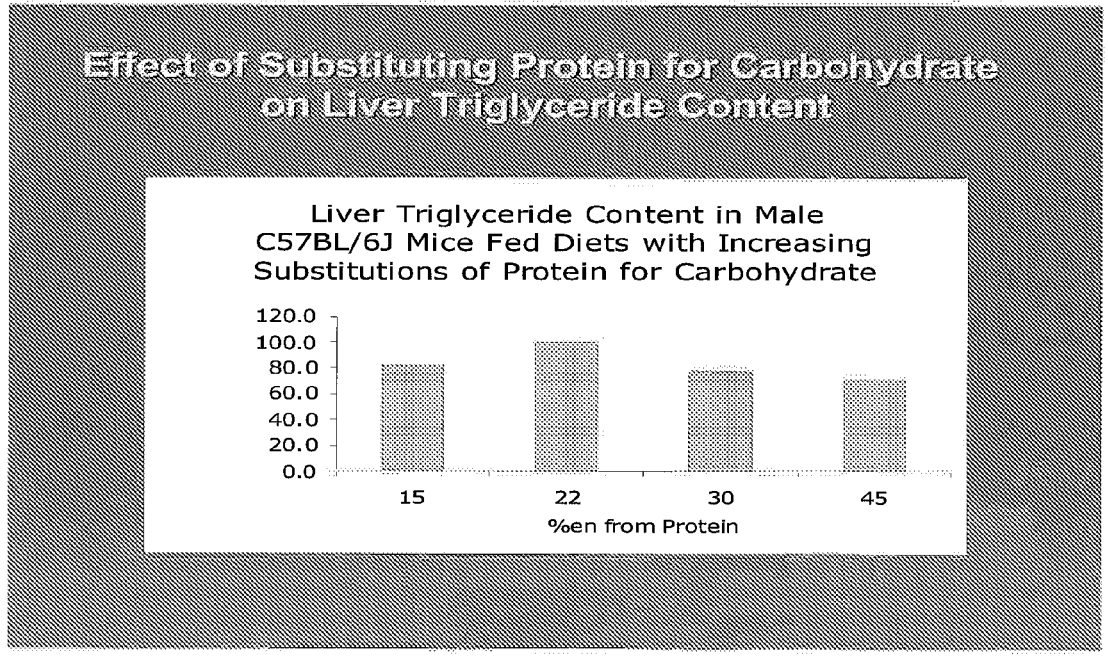
FIG. 28 graphically illustrates effect of substituting protein for carbohydrate on liver triglyceride content.
Figure 29:
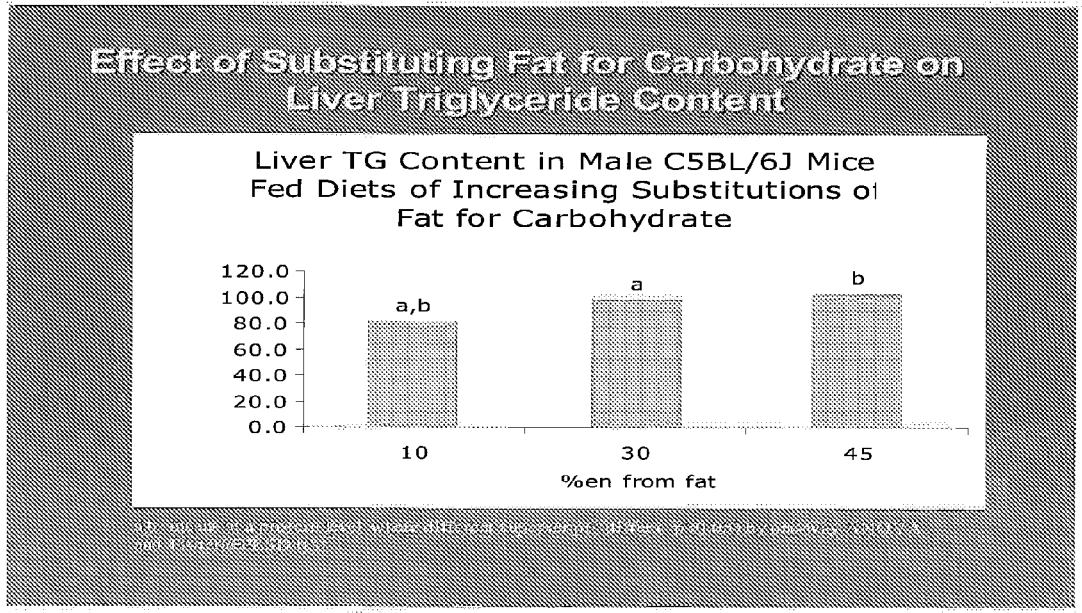
FIG. 29 graphically illustrates effect of substituting fat for carbohydrate on liver triglyceride content.
Figure 30:
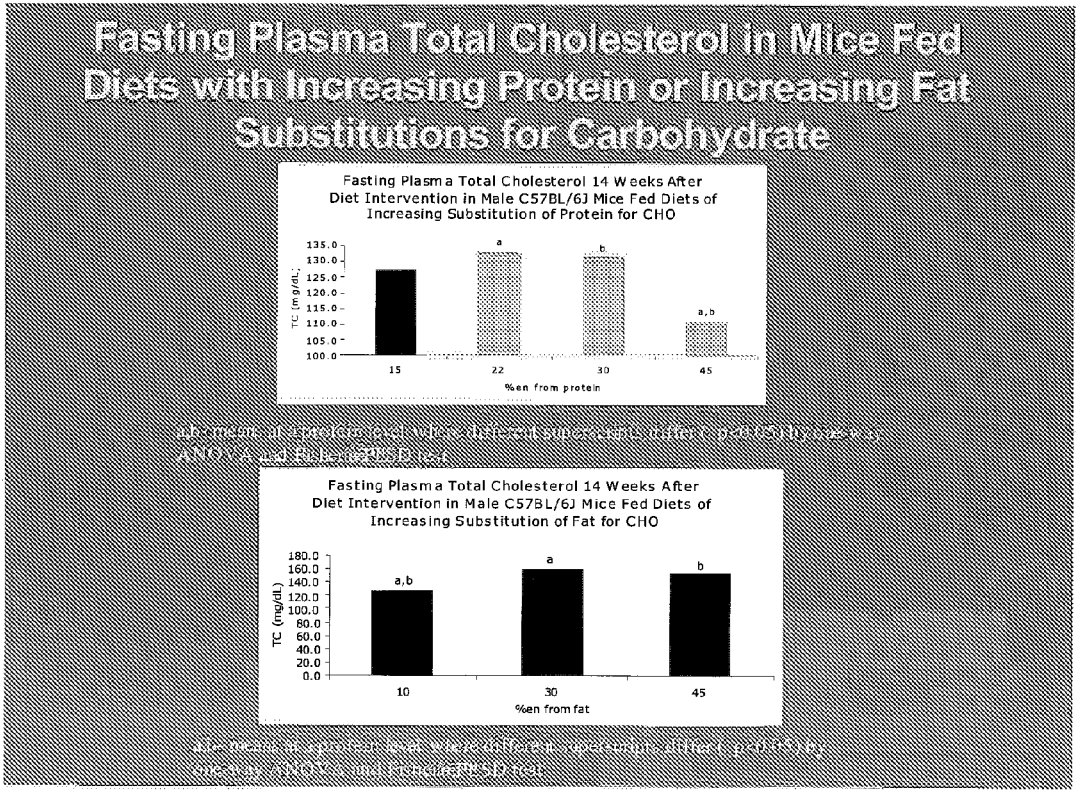
FIG. 30 graphically illustrates fasting plasma total cholesterol in mice fed diets with increasing protein or increasing fat substitutions for carbohydrate.
Figure 31:
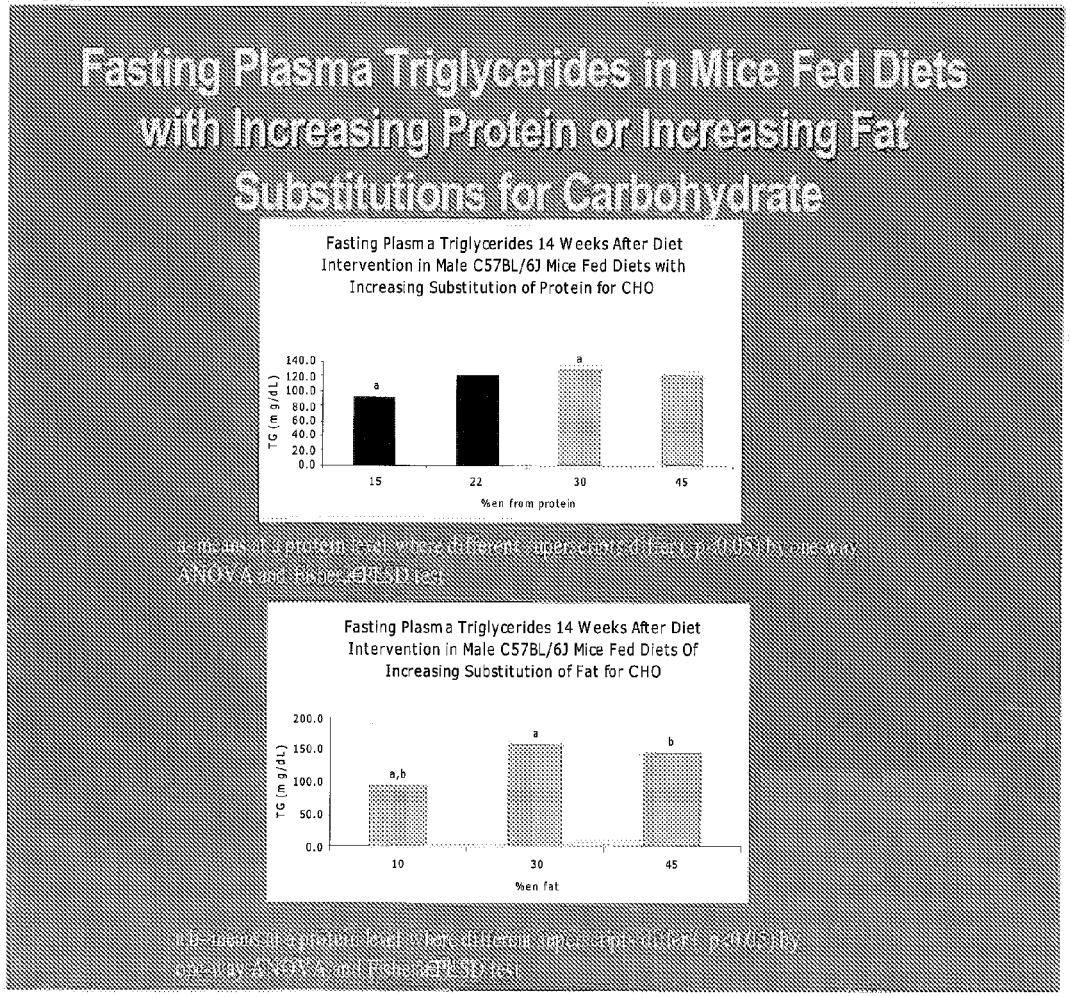
FIG. 31 graphically illustrates fasting plasma triglycerides in mice fed diets with increasing protein or increasing fat substitutions for carbohydrate.

*Cholesterol content (per kcal) is similar (185 mg/1000 kcal) for all diets
Diets were prepared without water/gel Fasting plasma lipids, cholesterol, oral glucose tolerance test, and insulin tolerance test were conducted after 16 weeks of diet intervention. Data are shown in Table 7 and FIG. 16.

TABLE 7

Body and organ weights and plasma lipids in C57BL/6J mice fed diets varying in CHO/Fat/Protein for 18 wk.

| | High-fat/ reg pro | High-fat/ high-pro | V.high-fat/ reg pro | Reg-fat/ high pro | mod high-fat/ reg pro |
|---|---|---|---|---|---|
| (CHO:Fat:Protein % en ratio) | (25:60:15) | (10:60:30) | (10:70:20) | (40:30:30) | (40:40:20) |
| Body weight (g) | | | | | |
| Initial | 21.8 ± 2.1 | 22.4 ± 1.9 | 21.9 ± 1.6 | 21.9 ± 1.5 | 22.0 ± 1.8 |
| Final | 36.5 ± 5.1a | 35.3 ± 4.2 | 32.6 ± 3.9 | 31.4 ± 2.3a | 32.5 ± 5.7 |
| Wt gain/day | 0.117 ± 0.031a,b,c | 0.103 ± 0.021d | 0.086 ± 0.020a | 0.076 ± 0.011b,d | 0.084 ± 0.035c |
| Organ weights (% BW) | | | | | |
| Liver | 3.40 ± 0.51 | 3.21 ± 0.40 | 3.34 ± 0.26 | 3.35 ± 0.26 | 3.35 ± 0.60 |
| Perirenal adipose | 1.97 ± 0.62a | 1.80 ± 0.58 | 1.82 ± 0.54 | 1.27 ± 0.68a | 1.61 ± 0.72 |

TABLE 7-continued

Body and organ weights and plasma lipids in C57BL/6J mice fed diets varying in CHO/Fat/Protein for 18 wk.

|  | High-fat/reg pro | High-fat/high-pro | V.high-fat/reg pro | Reg-fat/high pro | mod high-fat/reg pro |
|---|---|---|---|---|---|
| Epididymal adipose | 5.56 ± 1.02a | 5.35 ± 1.44b | 4.75 ± 1.31 | 3.93 ± 1.44a,b | 4.77 ± 1.72 |
| Combine adipose | 7.54 ± 1.54a | 7.16 ± 1.98 | 6.57 ± 1.74 | 5.21 ± 2.07a | 6.38 ± 2.39 |
| Kidney | 1.16 ± 0.14a,b | 1.35 ± 0.13a | 1.36 ± 0.14b | 1.29 ± 0.11 | 1.29 ± 0.26 |
| Cecum | 0.07 ± 0.18a,b | 0.85 ± 0.22 | 0.85 ± 0.15 | 0.90 ± 0.16a | 0.89 ± 0.19b |
| Pancreas | 0.48 ± 0.08 | 0.55 ± 0.10 | 0.53 ± 0.06 | 0.57 ± 0.09 | 0.52 ± 0.14 |
| Heart | 0.36 ± 0.05a,b,c | 0.41 ± 0.04 | 0.44 ± 0.08a | 0.43 ± 0.04b | 0.46 ± 0.10c |
| Plasma |  |  |  |  |  |
| TOTAL CHOLESTEROL (mg/dL) | 145 ± 35a | 121 ± 19 | 106 ± 18a,b | 126 ± 24 | 135 ± 26b |
| TRIGLYCERIDES (mg/dL) | 80 ± 26 | 72 ± 37 | 65 ± 27 | 60 ± 19 | 69 ± 22 |
| Glucose (mg/dL) | 172 ± 24 | 184 ± 39a | 161 ± 22 | 147 ± 24a | 159 ± 20 |

Values are means ± SD (n = 8-10)
a,b,c . . . Means in a row with a common superscript are significantly different (p < 0.05) using one-way ANOVA and Fisher's PLSD test A diet containing a fat to protein ratio of 1:1 decreased adipose deposits, improved insulin tolerance, and decreased blood glucose levels better than ratios of 2:1, 3.5:1 and 4:1. Increasing the protein level above 15% of energy seemed to improve insulin sensitivity and allow for better glucose control.

The 3.5:1 ratio had highest insulin resistance. However, it also had the lowest total cholesterol levels. The diets with high protein (30% protein) increased the kidney weight and may raises questions about safety and kidney damage.

It appears that a 1:1 ratio (Diet 4, with FAT and PROTEIN both at 30% en) generated the best results, i.e., the adipose deposits were less, the ITT glucose metabolism curve was best, the fasting blood glucose was lowest, and the cecum largest. Also, the 3.5:1 ratio was the worst for ITT, but did prove to yield the lowest TC, at least when the protein level was at 20% en. Increasing protein from 15% en seemed to improve that parameter, which could be explored to advantage someday in the future.

High protein seemed to raise kidney weights, which is a consistent finding in our studies. That observation raises many questions about safety and kidney damage in the long run, so protein levels much above 30% en are questionable. The lowest protein produced the smallest kidney size, to reaffirm the prot/kidney relationship.

As the fat:protein ratio rises above 1.0, the metabolic responses tend to deteriorate. This presumably is somewhat influenced by the absolute amount of the protein, with limits for best performance probably ranging between 20-35% en as protein, from lowest to highest sides, respectively.

Study 13—An Increased Ratio of Dietary Protein to Carbohydrate Improves Risk Factors Concerning Obesity, Cardiovascular Disease and Diabetes Compared to an Increased Ratio of Dietary Fat to Carbohydrate The rising epidemic of obesity and its related health issues (including diabetes and atherosclerosis) in America and other developing countries has spurred a significant interest in how the macronutrient composition of diet can be modified in order to promote weight loss and ameliorate its related risk factors. Specifically, there has been much controversy over what the optimal carbohydrate-to-fat-to-protein ratio should be. This controversy has been embodied in the Atkins (high-fat, high-protein) versus Ornish (low-fat, high-carbohydrate) diet debate.

C57BL/6J (obese mouse model) mice were randomized to one of 6 diets: 1) normal protein/high carbohydrate diet (75% CHO, 15% protein, 10% fat); 2) Moderate protein/high carbohydrate diet (68% CHO, 22% protein, 10% fat); 3) high protein/high carbohydrate (60% CHO, 30% protein, 10% fat); 4) very high protein/moderate carbohydrate (45% CHO, 45% protein, 10% fat); 5) AHA diet (55% CHO, 15% protein, 30% fat); and 6) moderate high fat/moderate carbohydrate (40% CHO, 15% protein, 45% fat). Details of each of these diets are shown in Table 8.

TABLE 8

Diet Compositions - High CARBOHYDRATE diets with varying fat or protein content fed to C57BL/6J mice

| | Diet # | | | | | |
|---|---|---|---|---|---|---|
| | 51 Normal-Pro High-CHO | 52 Moderate-Pro High-CHO | 53 High-Pro High-CHO | 54 Very High-Pro Moderate CHO | 55 AHA | 56 Moderate High-Fat Moderate-CHO |
| CHO:Fat:Protein % en | 75:10:15 | 68:10:22 | 60:10:30 | 45:10:45 | 55:30:15 | 40:45:15 |
| g/kg | | | | | | |
| Casein | 75 | 110 | 150 | 224 | 85 | 93 |
| Lactalbumin | 75 | 110 | 150 | 224 | 85 | 93 |

TABLE 8-continued

Diet Compositions - High CARBOHYDRATE diets with varying fat or protein content fed to C57BL/6J mice

| | Diet # | | | | | |
|---|---|---|---|---|---|---|
| | 51 Normal-Pro High-CHO | 52 Moderate-Pro High-CHO | 53 High-Pro High-CHO | 54 Very High-Pro Moderate CHO | 55 AHA | 56 Moderate High-Fat Moderate-CHO |
| Dextrose | 239 | 217 | 191 | 144 | 197 | 158 |
| Cornstarch | 509 | 461 | 407 | 306 | 418 | 335 |
| Fat | | | | | | |
| SFA:MUFA:PUFA (% en) | 3.3:3.3:3.3 | 3.3:3.3:3.3 | 3.3:3.3:3.3 | 3.3:3.3:3.3 | 10:10:10 | 15:15:15 |
| Butter fat | 6 | 6 | 6 | 6 | 19 | 34 |
| Tallow | 15 | 15 | 15 | 15 | 51 | 85 |
| Soybean | 23 | 23 | 23 | 23 | 80 | 131 |
| Fat/protein % en ratio | 0.67 | 0.45 | 0.33 | 0.22 | 2 | 3 |
| kcal/g diet (drywt.) | 3.988 | 3.988 | 3.988 | 3.988 | 4.49 | 4.966 |
| Mineral mix (Ausman-Hayes) | 44 | 44 | 44 | 44 | 50 | 55 |
| Vitamin mix (Hayes-Cathcart) | 11 | 11 | 11 | 11 | 12 | 13 |
| Choline chloride | 3 | 3 | 3 | 3 | 3 | 3 |
| Cholesterol | 0.7 | 0.7 | 0.7 | 0.7 | 0.73 | 0.75 |

Fasting plasma lipids, cholesterol, oral glucose tolerance test and insulin tolerance test were conducted after 16 weeks of diet intervention. Data reported in the literature and collected by the Hayes lab thus far have provided evidence favoring a diet high in fat and protein over the more conventionally accepted low-fat, high-carbohydrate diet in terms of decreased weight gain, adipose reserves, and risk for cardiovascular disease. While our primary focus has been the fat-to-carbohydrate ratio, insight has been gained on the importance of the fat-to-protein ratio in the context of a high fat diet. In a recent mouse study, a reduced fat:protein ratio (the highest protein intake) in the context of a high-fat high-protein diet resulted in less weight gain and lower plasma cholesterol than high-fat with normal protein intake. These findings have led to the hypothesis that the same pattern might hold true for lower carbohydrate:protein ratios in a high-carbohydrate diet.

Therefore, Study 13 focused on the carbohydrate:protein ratio in the context of a high-carbohydrate diet in order to elucidate the importance of this ratio in relation to obesity, atherosclerosis and diabetes. A substitution of fat-for-carbohydrate with protein constant was conducted in parallel to protein-for-carbohydrate with fat low and constant (Diets 1-4) in order to provide a direct comparison between the two concepts in the same study. Male C57BL/6J mice (a strain known to be susceptible to diet-induced obesity) were split into six different diet groups. Among the 6 different diet groups, 1-4 had substitutions of protein for carbohydrate to cover a 3-fold range in protein from 15% en to 45% en (keeping energy from fat constant at 10%) and 3 diets were designed to show the substitution of fat for carbohydrate over a 4.5-fold range from 10-45% en (keeping energy from protein constant at 15%). The latter comparison shared a group from the protein-carbohydrate matrix. See Table 8.

Results of the study are shown in Tables 9-26 and FIGS. 17-31. These results revealed that replacing carbohydrate with protein (increasing the protein:carbohydrate ratio) resulted in decreased plasma total cholesterol and liver esterified cholesterol (EC), somewhat increasing plasma and muscle triglyceride content while decreasing insulin sensitivity, i.e., replacing carbohydrate with protein did not seem to help glucose metabolism at this low fat intake. So protein may not be so good if fat intake is low. Replacing carbohydrate with fat (i.e., the transition from the highest carbohydrate to the highest fat diet) decreased liver esterified cholesterol and decreased insulin sensitivity, also suggesting that adding fat at the expense of carbohydrate did not favor glucose metabolism.

Furthermore, unlike the protein substitution for carbohydrate, increasing the fat:carbohydrate ratio significantly increased adiposity and weight gain as well as plasma, muscle, and liver triglycerides. Thus, high fat is not good. While the design of this study focused on the protein:carbohydrate and the fat:carbohydrate ratios, these results also contribute to our knowledge of the protein:fat ratio. As the latter ratio increased, insulin sensitivity increased, adiposity significantly decreased, while plasma and liver cholesterol as well as plasma, liver, and muscle triglycerides decreased. Thus, the decreased insulin sensitivity of Atkins diets would appear to be from fat. This means that too high fat is bad, but too low protein is little better, so substitute into the carbohydrate pool, all of which would suggest a convergence somewhere in the middle of the triangle.

In summary, replacing carbohydrate with protein had a beneficial effect on risk of obesity, diabetes, and cardiovascular disease up to 30% en as protein. Increasing the protein:carbohydrate ratio induced higher insulin sensitivity, significantly lower adipose reserves, and lower plasma, muscle, and liver triglyceride content than mice fed diets of comparable substitutions of fat for carbohydrate. Therefore, when reducing the carbohydrate content of a high-carbohydrate diet, substitution with protein results in a lower risk of obesity, diabetes, and atherosclerosis than substitution with fat in this mouse model.

The beneficial effects of higher protein on glucose control may not occur when fat intake is too low. Replacing carbohydrate with protein decreased plasma total cholesterol and liver esterified cholesterol levels. It also increased plasma and muscle triglyceride content levels while it decreased insulin sensitivity (See FIG. 17). Therefore, replacing carbohydrate with protein did not seem to help glucose metabolism at a fat intake of 10% of energy.

Replacing carbohydrate with fat decreased liver esterified cholesterol and decreased insulin sensitivity (See FIG. 18), also suggesting that adding fat at the expense of carbohydrate did not favor glucose metabolism. Furthermore, unlike the protein substitution for carbohydrate, increasing the fat:carbohydrate ratio significantly increased adiposity and weight gain as well as plasma, muscle, and liver triglycerides. Thus, high fat is not good.

Replacing carbohydrate with protein had a beneficial effect on risk of obesity, diabetes, and cardiovascular disease up to 30% of energy as protein. Increasing the protein to carbohydrate ratio induced higher insulin sensitivity, significantly lower adipose reserves, and lower plasma, muscle, and liver triglyceride content than mice fed diets of comparable substitutions of fat for carbohydrate. Therefore, when reducing the carbohydrate content of a high-carbohydrate diet, substitution with protein results in a lower risk of obesity, diabetes and atherosclerosis than substitution with fat in this mouse model.

TABLE 9

Caloric and cholesterol intakes in male C57BL/6J mice fed diets of various macronutrient composition

|  | Normal Pro High-CHO | Moderate Pro High-CHO | High-Pro High-CHO | Very High-Pro Moderate CHO | AHA | Moderate High-Fat Moderate CHO |
|---|---|---|---|---|---|---|
| CHO:Fat:Pro | 75:10:15 | 68:10:22 | 60:10:30 | 45:10:45 | 55:30:15 | 40:45:15 |
| Caloric intake (kcal/mouse/day) | 18.2 ± 0.6 | 18.2 ± 1.6 | 18.1 ± 1.6 | 16.3 ± 2.0 | 18.8 ± 1.0 | 17.5 ± 1.6 |
| Cholesterol intake (mg/mouse/day) | 3.5 | 3.3 | 3.3 | 3 | 3.5 | 3.2 |

TABLE 10

Liver Free Cholesterol, Cholesterol Ester and TRIGLYCERIDES Content in male C57BL/6J mice fed diets with increasing substitutions of protein for carbohydrate

|  | Normal Pro High-CHO | Moderate Pro High-CHO | High-Pro High-CHO | Very High-Pro Moderate CHO |
|---|---|---|---|---|
| CHO:Fat:Pro liver lipids (mg/g liver) | 75:10:15 | 68:10:22 | 60:10:30 | 45:10:45 |
| FC | 6.2 ± 0.7 | 5.8 ± 1.3 | 6 ± 1.3 | 6 ± 1.5 |
| EC | 7.2a,b,c ± 3.2 | 4.7a,d,e ± 1.5 | 2.7b,d,f ± 1.3 | 0.8c,e,f ± 0.3 |
| TC | 13.4a,b,c ± 2.9 | 10.6a,d ± 2.6 | 8.7b ± 2.2 | 6.8c,d ± 1.6 |
| liver TRIGLYCERIDES (mg/g liver) | 82.1 ± 35 | 100.7 ± 21 | 77.9 ± 16 | 71.1 ± 31 | a,b,c,d,e,fMeans in a row with different superscripts differ (p < 0.05) by one-way ANOVA and Fisher's PLSD test

TABLE 11

Liver Free Cholesterol, Cholesterol Ester and TRIGLYCERIDES Content in male C57BL/6J mice fed diets with increasing substitutions of fat for carbohydrate

|  | Normal Pro High-CHO | AHA | Moderate High-Fat Moderate CHO |
|---|---|---|---|
| CHO:Fat:Pro liver lipids (mg/g liver) | 75:10:15 | 55:30:15 | 40:45:15 |
| FC | 6.2a ±0.7 | 5.7b ±0.9 | 8.0a, b ±1.2 |
| EC | 7.2a, b ±3.2 | 3.2a ±1.3 | 2.2b ±0.8 |
| TC | 13.4a, b ±2.9 | 8.9a ±2.1 | 10.1b ±1.7 |
| liver TRIGLYCERIDES (mg/g liver) | 82.1a, b ± 35 | 98.8a ±36 | 103.6b ±42 | a, bMeans in a row with different superscripts differ (p < 0.05) by one-way ANOVA and Fisher's PLSD test

TABLE 12

Organ Weights (expressed as % of Body Weight) for males C57BL/6J mice fed diets with increasing protein substitution for carbohydrate

|  | Normal Pro High-CHO | Moderate Pro High-CHO | High-Pro High-CHO | Very High-Pro Moderate CHO |
|---|---|---|---|---|
| CHO:Fat:Pro | 75:10:15 | 68:10:22 | 60:10:30 | 45:10:45 |
| Organ Weights (% of body weight) | | | | |
| Liver | 4.35 ± 0.3 | 4.09 ± 0.33 | 3.96 ± 0.22 | 4.03 ± 0.28 |
| Peri-renal adipose | 1.08 ± 1.0 | 1.42 ± 0.5 | 1.22 ± 0.4 | 0.85 ± 0.5 |
| Epididymal Adipose | 2.53 ± 1.2 | 4.36 ± 1.1 | 3.72 ± 0.8 | 3.10 ± 1.5 |
| Kidney | 1.24 ± 0.11a | 1.31 ± 0.07b | 1.31 ± 0.08c | 1.51 ± 0.1a, b, c |
| Cecum | 0.88 ± 0.1 | 0.72 ± 0.1 | 0.98 ± 0.1 | 0.98 ± 0.2 |
| Heart | 0.5 ± 0.05 | 0.48 ± 0.05 | 0.48 ± 0.04 | 0.51 ± 0.03 |
| Body Weight | | | | |
| Initial | 21 ± 1.4 | 21 ± 1.3 | 21 ± 1.3 | 21 ± 2.1 |
| Final | 29.6 ± 3.3 | 30.9 ± 2.7 | 29.2 ± 1.2 | 28.4 ± 2.6 |
| Wt Gain | 8.5 ± 2.3 | 10.0 ± 1.9 | 8.3 ± 0.8 | 7.7 ± 1.0 | a, b, cMeans in a row with different superscripts differ ($p < 0.05$) by one-way ANOVA and Fisher's PLSD test

TABLE 13

Organ Weights (expressed as % of Body Weight) for male C57BL.6J mice fed diet with increasing fat substitution for carbohydrate

|  | Normal Pro High-CHO | AHA | Moderate High-Fat Moderate CHO |
|---|---|---|---|
| CHO:Fat:Pro | 75:10:15 | 55:30:15 | 40:45:15 |
| Organ Weights (% of body weight) | | | |
| Liver | 4.35 ± 0.3a, b | 3.65 ± 0.26a | 3.4 ± 0.57b |
| Peri-renal adipose | 1.08 ± 1.0a, b | 2.09 ± 0.5a | 2.02 ± 1.1b |
| Epididymal Adipose | 2.53 ± 1.2a, b | 5.8 ± 1.1a | 6.18 ± 2.3b |
| Kidney | 1.24 ± 0.11a, b | 1.1 ± 0.15a | 1.02 ± 0.2b |
| Cecum | 0.88 ± 0.1 | 0.79 ± 0.2 | 0.77 ± 0.3 |
| Heart | 0.5 ± 0.05a, b | 0.43 ± 0.04a | 0.39 ± 0.10b |
| Body Weight | | | |
| Initial | 21 ± 1.4 | 21 ± 0.7 | 21 ± 1 |
| Final | 29.6 ± 3.3a, b | 34.6 ± 2.2a | 37.3 ± 5.9b |
| Wt Gain | 8.5 ± 2.3a, b | 13.6 ± 1.9a | 16.6 ± 5.1b | a, bMeans in a row with different superscripts differ ($p < 0.05$) by one-way ANOVA and Fisher's PLSD test

TABLE 14

Fasting plasma total cholesterol and triglycerides 10 wks and 14 wks after diet intervention in male C57BL/6J mice fed diets of increasing protein substitution for carbohydrate

|  | Normal Pro High- CHO | Moderate Pro High- CHO | High- Pro High- CHO | Very High- Pro Moderate CHO |
|---|---|---|---|---|
| CHO:Fat:Pro | 75:10:15 | 68:10:22 | 60:10:30 | 45:10:45 |
| Plasma TOTAL CHOLESTEROL (mg/dL) | | | | |
| 10 wks | 137 ± 7 | 139 ± 11a | 147 ± 10b | 122 ± 14a, b |
| 14 wks | 127 ± 15 | 133 ± 20a | 131 ± 7b | 111 ± 7a, b |
| Plasma TRIGLYCERIDES (mg/dL) | | | | |
| 10 wks | 94 ± 16 | 100 ± 34 | 114 ± 41 | 90 ± 9 | a, bMeans in a row with different superscripts differ ($p < 0.05$) by one-way ANOVA and Fisher's PLSD test

TABLE 15

Fasting plasma TOTAL CHOLESTEROL and TRIGLYCERIDES- 10 wks and 14 wks after diet intervention in male C57BL/6J mice fed diets of increasing fat substitution for carbohydrate

|  | Normal Pro High- CHO | AHA | Moderate High- Fat Moderate CHO |
|---|---|---|---|
| CHO:Fat:Pro | 75:10:15 | 55:30:15 | 40:45:15 |
| Plasma TOTAL CHOLESTEROL (mg/dL) | | | |
| 10 wks | 137 ± 7a, b ± 7 | 174 ± 17a ± 17 | 173 ± 27b ± 27 |
| 14 wks | 127 ± 15a, b | 160 ± 23a | 152 ± 26b |
| Plasma TRIGLYCERIDES (mg/dL) | | | |
| 10 wks | 94 ± 16a, b | 140 ± 45a | 105 ± 25b | a, bMeans in a row with different superscripts differ ($p < 0.05$) by one-way ANOVA and Fisher's PLSD test

TABLE 16

A: Macronutrient Proportions - protein substitutions

|  | Normal Pro High-CHO | Moderate Pro High-CHO | High-Pro High-CHO | Very High-Pro Moderate CHO |
|---|---|---|---|---|
| CHO:Fat:Protein (% en) | 75:10:15 | 68:10:22 | 60:10:30 | 45:10:45 |
| Prot:Fat (% en) | 1.5 | 2.2 | 3 | 4.5 |

TABLE 16-continued

B: Macronutrient Proportions - protein

| Diet | CHO:Fat:Pro (% en) | Pro:CHO (% en) | Caloric Intake (g/mouse/day) |
|---|---|---|---|
| Normal Pro High-CHO | 75:10:15 | 0.2 | 18.2 |
| Moderate Pro High-CHO | 68:10:22 | 0.3 | 18.2 |
| High-Pro High-CHO | 60:10:30 | 0.5 | 18.1 |
| Very High-Pro Moderate CHO | 45:10:45 | 1 | 16.3 |

C: Macronutrient Proportions - fat substitutions

|  | Normal Pro High CHO | AHA | Moderate High-Fat Moderate CHO |
|---|---|---|---|
| CHO:Fat:Pro (% en) | 75:10:15 | 55:30:15 | 40:45:15 |
| Pro:Fat (% en) | 1.5 | 0.5 | 0.33 |

**SFA:MUFA:PUFA kept at 1:1:1 % en

D: Macronutrient Proportions - fat substitutions

| Diet | CHO:Fat:Protein (% en) | Fat:CHO (% en) | Caloric Intake (g/mouse/day) |
|---|---|---|---|
| Normal Pro High-CHO | 75:10:15 | 0.1 | 18.2 |
| Normal fat Moderate High-CHO | 55:30:15 | 0.5 | 18.8 |
| Moderate High- Fat Moderate CHO | 40:45:15 | 0.9 | 17.5 |

TABLE 17

Weight Gain and Adiposity - Protein Substitution

|  | Normal Pro High-CHO | Moderate Pro High-CHO | High-Pro High-CHO | Very High-Pro Moderate CHO |
|---|---|---|---|---|
| CHO:Fat:Pro | 75:10:15 | 68:10:22 | 60:10:30 | 45:10:45 |
| Body Weight |  |  |  |  |
| Initial | 21 ± 1.4 | 21 ± 1.3 | 21 ± 1.3 | 21 ± 2.1 |
| Final | 29.6 ± 3.3 | 30.9 ± 2.7 | 29.2 ± 1.2 | 28.4 ± 2.6 |
| Wt Gain | 8.5 ± 2.3 | 10.0 ± 1.9 | 8.3 ± 0.8 | 7.7 ± 1.0 |
| Organ Weights |  |  |  |  |
| Peri-renal adipose | 1.08 ± 1.0 | 1.42 ± 0.5 | 1.22 ± 0.4 | 0.85 ± 0.5 |

(% of Body Weight)

TABLE 18

Weight Gain and Adiposity - Fat Substitution

|  | Normal Pro High-CHO | AHA | Moderate High-Fat Moderate CHO |
|---|---|---|---|
| CHO:Fat:Pro | 75:10:15 | 55:30:15 | 40:45:15 |
| Body Weight |  |  |  |
| Initial | 21 ± 1.4 | 21 ± 0.7 | 21 ± 1 |
| Final | 29.6 ± 3.3a,b | 34.6 ± 2.2a | 37.3 ± 5.9b |
| Wt Gain | 8.5 ± 2.3a,b | 13.6 ± 1.9a | 16.6 ± 5.1b |
| Organ Weights (% of Body Weight) |  |  |  |
| Peri-renal adipose | 1.08 ± 1.0a,b | 2.09 ± 0.5a | 2.02 ± 1.1b |

TABLE 19

Plasma, Liver and Muscle Triglyceride Content- Protein Substitution

|  | Normal Pro High- CHO | Moderate Pro High- CHO | High- Pro High- CHO | Very High-Pro Moderate CHO |
|---|---|---|---|---|
| CHO:Fat:Pro | 75:10:15 | 68:10:22 | 60:10:30 | 45:10:45 |
| Plasma TRIGLYCERIDES (mg/dL) | 93a ±24 | 120 ±20 | 129a ±18 | 120 ±26.0 |
| Liver TRIGLYCERIDES (mg/g liver) | 82.1 ±35 | 100.7 ±21 | 77.9 ±16 | 71.1 ±31 |
| Muscle TRIGLYCERIDES (mg/g muscle) | 7.85a ±2.1 | 11.07 ±5.1 | 12.81a ±2.3 | 11.65 ±3.65 |

TABLE 20

Plasma, Liver and Muscle Triglyceride Content - Fat Substitution

|  | Normal Pro High-CHO | AHA | Moderate High-Fat Moderate CHO |
|---|---|---|---|
| CHO:Fat:Pro | 75:10:15 | 55:30:15 | 40:45:15 |
| Plasma TRIGLYCERIDES (mg/dL) | 93a, b ±24 | 159a ±45 | 144b ±43 |
| Liver TRIGLYCERIDES (mg/g liver) | 82.1a, b ±35 | 98.8a ±36 | 103.6b ±42 |
| Muscle TRIGLYCERIDES (mg/g muscle) | 7.85a, b ±2.1 0.2 | 15.21a ±3.6 0.32 | 19.69b ±7.6 0.5 |
| Pro:CARBOHYDRATE (Fat 10% en) | 93 0.13 | 120 0.54 | 129 1.13 |
| Fat:CARBOHYDRATE (Protein 15% en) | 93 | 159 | 144 |

TABLE 20-continued

Plasma, Liver and Muscle Triglyceride Content - Fat Substitution

|  | Normal Pro High-CHO | Moderate Pro High-CHO | High-Pro High-CHO |
|---|---|---|---|
| CHO:Fat:Pro | 75:10:15 | 68:10:22 | 60:10:30 |
| Plasma TC (mg/dL) | 127 ±15 | 133a ±20 | 131b ±7 |
| Liver EC (mg/g liver) | 7.2a, b, c ±3.2 | 4.7a, d, e ±1.5 | 2.7b, d, f ±1.3 |

|  | Normal Pro High-CHO | AHA | Moderate High-Fat Moderate CHO |
|---|---|---|---|
| CHO:Fat:Pro | 75:10:15 | 55:30:15 | 40:45:15 |
| Plasma TC (mg/dL) | 127a, b ±15 | 160a ±23 | 152b ±26 |
| Liver EC (mg/g liver) | 7.2a, b ±3.2 | 3.2a ±1.3 | 2.2b ±0.8 |

TABLE 21

Blood Glucose - Taken 12 weeks After Diet Intervention from Male C57BL/6J Mice Fed Diets of Varying Macronutrient Composition

| Normal Pro High-CHO | Moderate Pro High-CHO | High-Pro High-CHO | Very High-Pro Moderate CHO | AHA | Moderate High-Fat Moderate CHO |
|---|---|---|---|---|---|
| 75:10:15 | 68:10:22 | 60:10:30 | 45:10:45 | 55:30:15 | 40:45:15 |
| $134.8^a \pm 22.8$ | $138.9^b \pm 21$ | $142.4^c \pm 12.7$ | $125.5^d \pm 39.3$ | $138.3^e \pm 10$ | $181.7^{a,b,c,d,e} \pm 11.3$ |

TABLE 22

Organ Weights (absolute values) for males C57BL/6J mice fed diets with increasing protein substitution for carbohydrate

|  | Normal Pro High-CHO | Moderate Pro High-CHO | High-Pro High-CHO | Very High-Pro Moderate CHO |
|---|---|---|---|---|
| CHO:Fat:Pro | 75:10:15 | 68:10:22 | 60:10:30 | 45:10:45 |
| Body Weight |  |  |  |  |
| Initial | 21 ± 1.4 | 21 ± 1.3 | 21 ± 1.3 | 21 ± 2.1 |
| Final | 29.6 ± 3.3 | 30.9 ± 2.7 | 29.2 ± 1.2 | 28.4 ± 2.6 |
| Wt Gain | 8.5 ± 2.3 | 10.0 ± 1.9 | 8.3 ± 0.8 | 7.7 ± 1.0 |
| Organ Weights (g) |  |  |  |  |
| Liver | 1.3 ± 0.15 | 1.31 ± 0.15 | 1.2 ± 0.05 | 1.18 ± 0.17 |
| Peri-renal adipose | 0.31 ± 0.28 | 0.44 ± 0.21 | 0.36 ± 0.14 | 0.24 ± 0.15 |
| Epidemal Adipose | $0.75 \pm 0.43^a$ | $1.35 \pm 0.45^a$ | 1.08 ± 0.27 | 0.87 ± 0.45 |
| Total Adipose | 1.05 ± 0.57 | 1.80 ± 0.70 | 1.55 ± 0.27 | 1.08 ± 0.64 |
| Kidney | $0.35 \pm 0.04^{a,b}$ | $0.40 \pm 0.03^a$ | 0.38 ± 0.03 | $0.41 \pm 0.05^b$ |
| Cecum | 0.25 ± 0.04 | 0.21 ± 0.01 | 0.28 ± 0.04 | 0.27 ± 0.07 |
| Heart | 0.14 ± 0.01 | 0.15 ± 0.01 | 0.14 ± 0.02 | 0.14 ± 0.02 |

[a,b,c]Means in a row with different superscripts differ (p < 0.05) by one-way ANOVA and Fisher's PLSD test

TABLE 23

Organ Weights (absolute values) for male C57BL/6J mice fed diet with increasing fat substitution for carbohydrate

|  | Normal Pro High-CHO | AHA | Moderate High-Fat Moderate CHO |
|---|---|---|---|
| CHO:Fat:Pro | 75:10:15 | 55:30:15 | 40:45:15 |
| Body Weight |  |  |  |
| Initial | 21 ± 1.4 | 21 ± 0.7 | 21 ± 1 |
| Final | $29.6 \pm 3.3^{a,b}$ | $34.6 \pm 2.2^a$ | $37.3 \pm 5.9^b$ |
| Wt Gain | $8.5 \pm 2.3^{a,b}$ | $13.6 \pm 1.9^a$ | $16.6 \pm 5.1^b$ |
| Organ Weights (g) |  |  |  |
| Liver | 1.3 ± 0.15 | 1.37 ± 0.06 | 1.34 ± 0.33 |
| Peri-renal adipose | $0.31 \pm .28^{a,b}$ | $0.74 \pm 0.21^a$ | $0.81 \pm 0.56^b$ |
| Epidemal Adipose | $0.75 \pm 0.43^{a,b}$ | $2.06 \pm 0.46^a$ | $2.4 \pm 1.09^b$ |

TABLE 23-continued

Organ Weights (absolute values) for male C57BL/6J mice fed diet with increasing fat substitution for carbohydrate

|  | Normal Pro High-CHO | AHA | Moderate High-Fat Moderate CHO |
|---|---|---|---|
| Total Adipose | $1.05 \pm 0.57^{a,b}$ | $2.77 \pm 0.7^a$ | $3.1 \pm 1.29^b$ |
| Kidney | 0.35 ± 0.04 | 0.38 ± 0.03 | 0.37 ± 0.02 |
| Cecum | 0.25 ± 0.04 | 0.28 ± 0.06 | 0.27 ± 0.05 |
| Heart | 0.14 ± 0.01 | 0.15 ± 0.01 | 0.14 ± 0.02 |

[a,b]Means in a row with different superscripts differ (p < 0.05) by one-way ANOVA and Fisher's PLSD test

TABLE 24

Macronutrient Proportions - protein substitutions

|  | Normal Pro High-CHO | Moderate Pro High-CHO | High-Pro High-CHO | Very High-Pro Moderate CHO |
|---|---|---|---|---|
| CHO:Fat:Protein (% en) | 75:10:15 | 68:10:22 | 60:10:30 | 45:10:45 |
| Prot:Fat (% en) | 1.5 | 2.2 | 3 | 4.5 |

TABLE 25

Macronutrient Proportions - fat substitutions

|  | Normal Pro High-CHO | AHA | Moderate High-Fat Moderate CHO |
|---|---|---|---|
| CHO:Fat:Protein (% en) | 75:10:15 | 55:30:15 | 40:45:15 |
| Prot:Fat (% en) | 1.5 | 0.5 | 0.33 |

**SFA:MUFA:PUFA kept at 1:1:1 % en

TABLE 26

Macronutrient Proportions - protein substitutions

| Diet | CHO:Fat:Pro (% en) | Pro:CHO (% en) | Caloric Intake (g/mouse/day) |
|---|---|---|---|
| Normal Pro High-CHO | 75:10:15 | 0.2 | 18.2 |
| Moderate Pro High-CHO | 68:10:22 | 0.3 | 18.2 |
| High-Pro High-CHO | 60:10:30 | 0.5 | 18.1 |
| Very High-Pro Moderate CHO | 45:10:45 | 1 | 16.3 |

TABLE 27

Macronutrient Proportions - fat substitutions

| Diet | CHO:Fat:Protein (% en) | Fat:CHO (% en) | Caloric Intake (g/mouse/day) |
|---|---|---|---|
| Normal Pro High-CHO | 75:10:15 | 0.1 | 18.2 |
| Normal fat Moderate High-CHO | 55:30:15 | 0.5 | 18.8 |
| Moderate High-Fat Moderate CHO | 40:45:15 | 0.9 | 17.5 |

Study 14

The objective of this study was to investigate the effect of a statin (Mevacor) on cholesterol levels. Each of three groups of ApoE (−/−) mice was fed one of three diets, each diet containing a different cholesterol level (i.e., 0, 0.4, and 0.8 g/kg). A fourth group was fed the diet containing 0.8 g/kg of cholesterol with the further inclusion of 0.5 g/kg of a statin (i.e., Mevacor). Details of the diet compositions are provided in Table 28.

TABLE 28

APOE mouse study diets with varying cholesterol levels + statins

| | gram per 1.0 kilo | | | |
|---|---|---|---|---|
| INGREDIENT | AHA #66 0% chol Green | AHA #67 0.04% chol Blue | AHA # 68 0.08% chol Red | AHA #69 0.08% chol + statin White |
| Casein | 100 | 100 | 100 | 100 |
| Lactalbumin | 100 | 100 | 100 | 100 |
| Dextrose | 187 | 187 | 187 | 187 |
| Cornstarch | 338 (+60 g in gel) | 338 (+60 g in gel) | 338 (+60 g in gel) | 338 (+60 g in gel) |
| Fat | | | | |
| Butter-chol stripped | 18 | 18 | 18 | 18 |
| Tallow-chol stripped | 60 | 60 | 60 | 60 |
| Soybean | 72 | 72 | 72 | 72 |
| Mineral mix (Ausman - Hayes) | 50 | 50 | 50 | 50 |
| Vitamin mix (Hayes - Cathcart) | 12 | 12 | 12 | 12 |
| Choline chloride | 3 | 3 | 3 | 3 |
| Mevacor | 0 | 0 | 0 | 0.5 |
| Cholesterol | 0 | 0.4 | 0.8 | 0.8 |

60 g starch in 800 mL water for gel preparation

Liver, aortal, and plasma cholesterol levels following 14 weeks of diet administration are shown in Table 29. Mice receiving the diet having the highest cholesterol component but administered a statin exhibited a significant reduction in liver, aortal, and plasma cholesterol levels as compared to those mice receiving the same diet but no statin. Significant reductions in epididymal and combined perirenal and epididymal adipose weight and tocopherol level were also observed.

TABLE 29

ApoE (−/−) mice fed for 14 wk diet with 0; 0.04 or 0.08% chol or 0.08% chol + Mevacor

| | Diet | | | |
|---|---|---|---|---|
| | 0% chol | 0.04% chol | 0.08% chol | 0.08% chol + statins |
| Body weight (g) | | | | |
| initial | 29.6 ± 2.8 | 29.8 ± 1.6 | 29.5 ± 1.8 | 29.7 ± 1.3 |
| final (after 14 wks) | 34.3 ± 2.6 | 32.7 ± 2.3 | 34.5 ± 2.3 | 33.2 ± 2.0 |
| Liver weight (% BW) | 3.88 ± 0.13 | 3.82 ± 0.33 | 3.83 ± 0.27 | 3.79 ± 0.30 |
| Kidney weight (% BW) | 1.19 ± 0.10 | 1.16 ± 0.09 | 1.11 ± 0.07 | 1.23 ± 0.10 |
| Adipose weight (% BW) | | | | |
| Perirenal | 1.09 ± 0.72$^a$ | 0.39 ± 0.20$^{a,b}$ | 1.06 ± 0.50$^b$ | 0.55 ± 0.62 |
| Epididymal | 2.91 ± 1.20$^a$ | 1.61 ± 0.39$^{a,b}$ | 3.11 ± 1.22$^{b,c}$ | 1.82 ± 1.25$^c$ |
| Combine Peri + Epi | 4.00 ± 1.86$^a$ | 1.99 ± 0.57$^{a,b}$ | 4.17 ± 1.71$^{b,c}$ | 2.36 ± 1.87$^c$ |
| Cecum weight (% BW) | 0.60 ± 0.12$^{a,b}$ | 0.84 ± 0.07$^a$ | 0.73 ± 0.18$^c$ | 0.91 ± 0.15$^{b,c}$ |
| Liver cholesterol (mg/g) | | | | |
| FC | 4.0 ± 1.3 | 4.1 ± 1.0 | 4.2 ± 1.8 | 3.3 ± 1.5 |
| EC | 2.3 ± 1.0 | 2.1 ± 1.2 | 2.8 ± 1.6 | 1.7 ± 1.1 |
| TC | 6.2 ± 2.2 | 6.1 ± 2.1 | 7.0 ± 1.6 | 5.0 ± 2.6 |

TABLE 29-continued

ApoE (−/−) mice fed for 14 wk diet with 0: 0.04 or 0.08% chol or 0.08% chol + Mevacor

| | Diet | | | |
|---|---|---|---|---|
| | 0% chol | 0.04% chol | 0.08% chol | 0.08% chol + statins |
| Aorta cholesterol (μg/g protein) | | | | |
| FC | 7.11 ± 3.95 | 10.17 ± 2.86 | 12.21 ± 5.44 | 8.69 ± 7.59 |
| EC | 0.56 ± 0.93$^a$ | 1.01 ± 0.81$^b$ | 5.22 ± 4.93$^{a,b,c}$ | 0.26 ± 0.42$^c$ |
| TC | 7.67 ± 4.21$^a$ | 11.18 ± 2.60 | 17.44 ± 8.72$^{a,b}$ | 8.95 ± 7.59$^b$ |
| Plasma | | | | |
| TOTAL CHOLESTEROL (mg/dL) | 627 ± 37$^{a,b}$ | 769 ± 120$^{a,c}$ | 1251 ± 136$^{b,c,d}$ | 748 ± 111$^d$ |
| TRIGLYCERIDES (mg/dL) | 109 ± 5 | 69 ± 13 | 106 ± 17 | 70 ± 37 |
| Retinol (μg/dL) | 32 ± 5$^{a,b}$ | 21 ± 5$^{a,c,d}$ | 31 ± 1$^c$ | 27 ± 4$^{b,d}$ |
| Tocopherol (μg/dL) | 1589 ± 244$^a$ | 1663 ± 188$^b$ | 974 ± 174$^{a,b,c}$ | 1459 ± 334$^c$ |
| a-Toc/Chol molar ratio | 2.26 ± 0.29$^{a,b,c,d}$ | 1.96 ± 0.19$^{a,e,f}$ | 1.42 ± 0.12$^{b,e,g}$ | 1.74 ± 0.14$^{d,f,g}$ |

Values are Mean ± SD (n = 7)
$^{a,b,c}$Means in a row sharing a common superscript are significantly different (p < 0.05) using one-way ANOVA and Fisher's PLSD test.

Study 15

The objective of this study was to gather more definitive data on atherosclerosis in the ApoE mouse to go with the obesity/insulin data in the C57BLj mouse of earlier studies, particularly Study 12. To that end, we fed similar Atkins/Ornish comparisons in these apoE (−/−) mice over a sustained period of 18 wks, so sufficient atherosclerosis would develop. In effect, we tested the fat:protein ratio to see how it might impact atherogenesis. We also used both males and females to see if that made a big difference on outcome variables examined.

Mice that were ApoE deficient were divided into 4 groups: 1) high fat/regular protein diet (25% CHO, 15% protein, 60% fat); 2) high fat/high protein diet (10% CHO, 30% protein, 60% fat); 3) very high fat/regular protein (70% CHO, 20% protein, 10% fat); and 4) high carbohydrate/regular protein (70% CHO, 20% protein, 10% fat). Details of the compositions of each diet are shown in Table 31.

TABLE 30A

Body and organ weights and plasma lipids in MALE ApoE−/− mice fed diets varying in CHO/Fat/Protein for 18 wk.

| | High-fat/reg pro* | High-fat/high-pro* | V.high-fat/reg pro* | High-CHO/reg pro* | High-CHO/reg pro** |
|---|---|---|---|---|---|
| (CHO:Fat:Protein % en ratio) | (25:60:15) | (10:60:30) | (10:70:20) | (70:10:20) | (70:10:20) |
| Fat:Protein ratio (% en) | 3.7 | 1.9 | 3.7 | 0.6 | 0.6 |
| 18:2 n-6 (% en) | 6.7 | 6.7 | 8.0 | 1.4 | 1.4 |
| Body weight (g) | | | | | |
| Initial | 25.3 ± 1.7 | 25.4 ± 2.0 | 25.5 ± 1.0 | 25.5 ± 1.7 | 25.0 ± 1.2 |
| Final | 35.6 ± 5.5$^a$ | 34.5 ± 3.4 | 35.7 ± 5.8$^b$ | 29.9 ± 2.3$^{a,b}$ | 32.2 ± 1.3 |
| Wt gain/day | 0.082 ± 0.051$^a$ | 0.072 ± 0.051 | 0.081 ± 0.046$^b$ | 0.035 ± 0.021$^{a,b}$ | 0.057 ± 0.015 |
| Organ weights (% BW) | | | | | |
| Liver | 4.13 ± 0.40$^a$ | 3.82 ± 0.22$^{b,c}$ | 3.78 ± 0.33$^{d,e}$ | 4.54 ± 0.25$^{a,b,d}$ | 4.31 ± 0.23$^{c,e}$ |
| Perirenal adipose | 1.49 ± 1.22 | 1.85 ± 0.44$^a$ | 1.78 ± 1.33$^b$ | 0.97 ± 0.29 | 0.50 ± 0.22$^{a,b}$ |
| Kidney | 1.22 ± 0.22 | 1.32 ± 0.08 | 1.20 ± 0.26 | 1.18 ± 0.07 | 1.18 ± 0.09 |
| Cecum | 0.86 ± 0.34$^a$ | 0.72 ± 0.09 | 0.62 ± 0.18$^{a,b}$ | 0.78 ± 0.12 | 0.91 ± 0.08$^b$ |
| Spleen | 0.39 ± 0.19 | 0.30 ± 0.10 | 0.36 ± 0.16 | 0.26 ± 0.05 | 0.30 ± 0.07 |
| Blood Glucose (mg/dL) | 138 ± 21 | 160 ± 10 | 160 ± 39 | 147 ± 7 | 149 ± 20 |
| Plasma | | | | | |
| TOTAL CHOLESTEROL (mg/dL) | 758 ± 397 | 991 ± 240 | 763 ± 241 | 938 ± 125 | 924 ± 84 |
| TRIGLYCERIDES (mg/dL) | 154 ± 76 | 163 ± 33 | 163 ± 76 | 137 ± 25 | 120 ± 21 |

Values are means ± SD (Male n = 5-6 and Female n = 4-5)
*First four groups of mice were fed same amounts of kcal/day.
**Mice fed ad libitum
$^{a,b,c...}$Means in a row with a common superscript are significantly different (p < 0.05) using one-way ANOVA and Fisher's PLSD test

TABLE 30B

Body and organ weights and plasma lipids in FEMALE ApoE−/− mice fed diets varying in CHO/Fat/Protein for 18 wk.

|  | High-fat/<br>reg pro* | High-fat/<br>high-pro* | V.high-fat/<br>reg pro* | High-CHO/<br>reg pro* | High-CHO/<br>reg pro** |
|---|---|---|---|---|---|
| (CHO:Fat:Protein % en ratio) | (25:60:15) | (10:60:30) | (10:70:20) | (70:10:20) | (70:10:20) |
| Fat:Protein ratio (% en) | 3.7 | 1.9 | 3.7 | 0.6 | 0.6 |
| 18:2n-6 (% en) | 6.7 | 6.7 | 8.0 | 1.4 | 1.4 |
| Body weight (g) | | | | | |
| Initial | 21.4 ± 1.4 | 20.2 ± 1.3 | 21.1 ± 0.5 | 22.1 ± 1.0 | 20.8 ± 0.8 |
| Final | 29.0 ± 3.7$^{a,b,c}$ | 25.7 ± 1.6$^a$ | 26.1 ± 2.8$^d$ | 22.9 ± 1.6$^{b,d}$ | 24.4 ± 0.9$^c$ |
| Wt gain | 0.060 ± 0.026$^{a,b}$ | 0.044 ± 0.016$^c$ | 0.039 ± 0.023$^d$ | 0.006 ± 0.011$^{a,c,d}$ | 0.028 ± 0.005$^b$ |
| Organ weights (% BW) | | | | | |
| Liver | 4.21 ± 0.20$^a$ | 4.06 ± 0.39$^{b,c}$ | 4.06 ± 0.20$^{d,e}$ | 4.64 ± 0.51$^{b,d}$ | 5.16 ± 0.59$^{a,c,e}$ |
| Perirenal adipose | 2.44 ± 0.90$^{a,b}$ | 1.89 ± 0.51$^{c,d}$ | 2.12 ± 0.24$^{e,f}$ | 0.76 ± 0.20$^{a,c,e}$ | 0.84 ± 0.35$^{b,d,f}$ |
| Kidney | 1.12 ± 0.06$^a$ | 1.27 ± 0.10$^{a,b,c}$ | 1.16 ± 0.08$^b$ | 1.21 ± 0.06 | 1.12 ± 0.06$^c$ |
| Cecum | 0.82 ± 0.14$^{a,b}$ | 0.88 ± 0.06$^{c,d}$ | 0.68 ± 0.06$^{a,c,e,f}$ | 1.02 ± 0.08$^{b,d,e,g}$ | 0.94 ± 0.06$^{f,g}$ |
| Spleen | 0.46 ± 0.08 | 0.46 ± 0.17 | 0.45 ± 0.09 | 0.49 ± 0.15 | 0.41 ± 0.04 |
| Blood Glucose (mg/dL) | 156 ± 12$^{a,b,c}$ | 119 ± 14$^{a,d}$ | 143 ± 19$^{e,f}$ | 113 ± 12$^{b,e}$ | 111 ± 11$^{c,f}$ |
| Plasma | | | | | |
| TOTAL CHOLESTEROL (mg/dL) | 679 ± 142$^a$ | 817 ± 134$^b$ | 603 ± 94$^{b,c,d}$ | 874 ± 135$^{a,c}$ | 816 ± 205$^d$ |
| TRIGLYCERIDES (mg/dL) | 125 ± 14$^{a,b}$ | 114 ± 10$^c$ | 121 ± 20$^{d,e}$ | 86 ± 13$^{a,c,d}$ | 95 ± 12$^{b,e}$ |

Values are means ± SD (Male n = 5-6 and Female n = 4-5)
*First four groups of mice were fed same amounts of kcal/day.
**Mice fed ad libitum
$^{a,b,c...}$Means in a row with a common superscript are significantly different (p < 0.05) using one-way ANOVA and Fisher's PLSD test

TABLE 31

ApoE mouse study diets high in fat or CARBOHYDRATE with varying levels of protein

| | gram per 1.0 kilo | | | |
|---|---|---|---|---|
| INGREDIENT | #62<br>High-fat/<br>reg pro<br>White | #63<br>High-fat/<br>high pro<br>Green | #64<br>V. high-fat/<br>reg pro<br>Red | #65<br>High-CHO/<br>reg pro<br>Blue |
| Casein | 106 | 213 | 142 | 95 |
| Lactalbumin | 106 | 212 | 141 | 95 |
| Dextrose | 115 | 47 | 52 | 222 |
| Cornstarch | 246 | 101 | 111 | 482 |
| Fat: | | | | |
| Butter | 92 | 92 | 124 | 13 |
| Tallow | 169 | 169 | 229 | 24 |
| Lard | 55 | 55 | 74 | 8 |
| Soybean | 52 | 52 | 70 | 7 |
| Mineral mix (Ausman - Hayes) | 58 | 58 | 61 | 42 |
| Vitamin mix (Hayes - Cathcart) | 15 | 15 | 17 | 11 |
| Choline chloride | 4 | 4 | 4 | 3 |
| Cholesterol (added) | 0.57 | 0.57 | 0.5 | 0.7 |

*No water or starch gel is added. Diet will be prepared in dry form.

Figure 32:
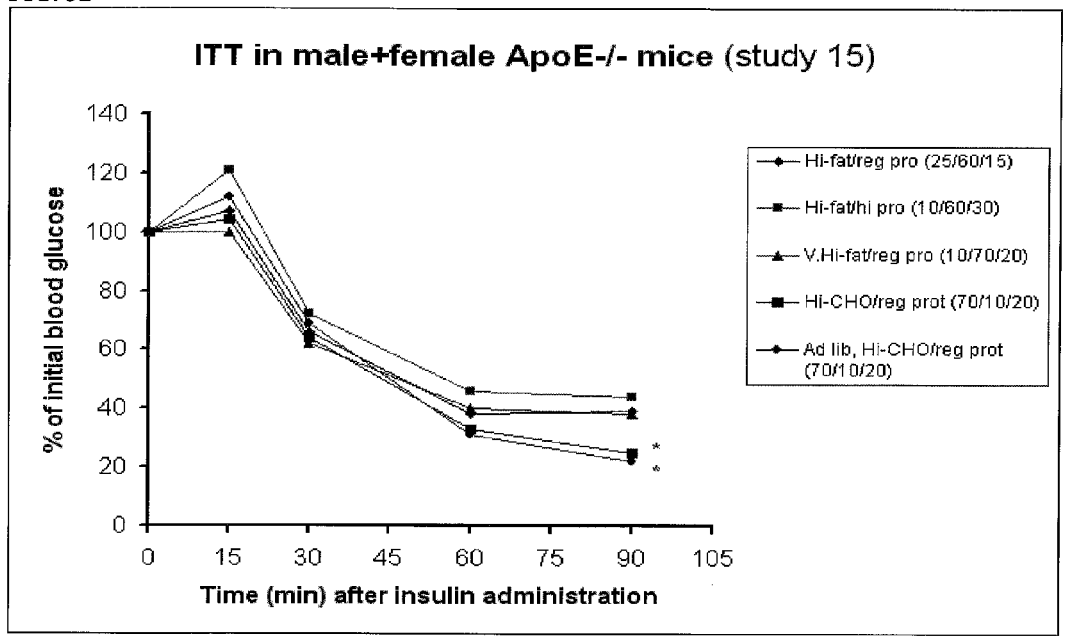
FIG. 32 graphically illustrates ITT in male+female ApoE−/− mice.
Figure 33:
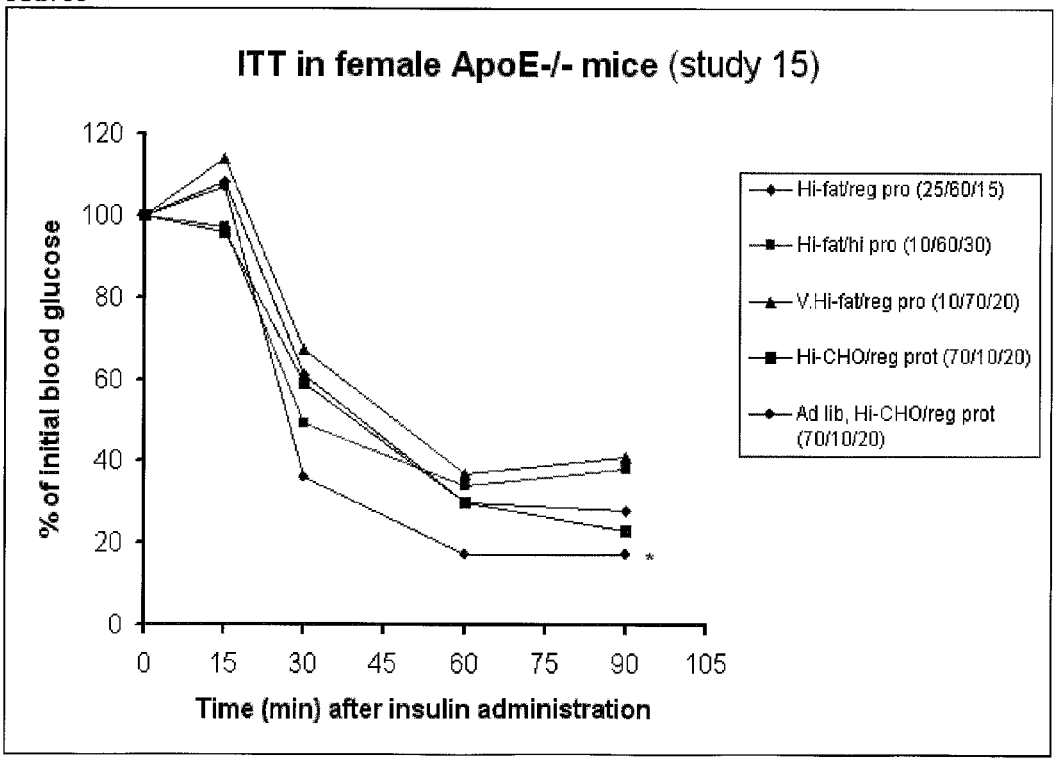
FIG. 33 graphically illustrates ITT in female ApoE−/− mice.
Figure 34:
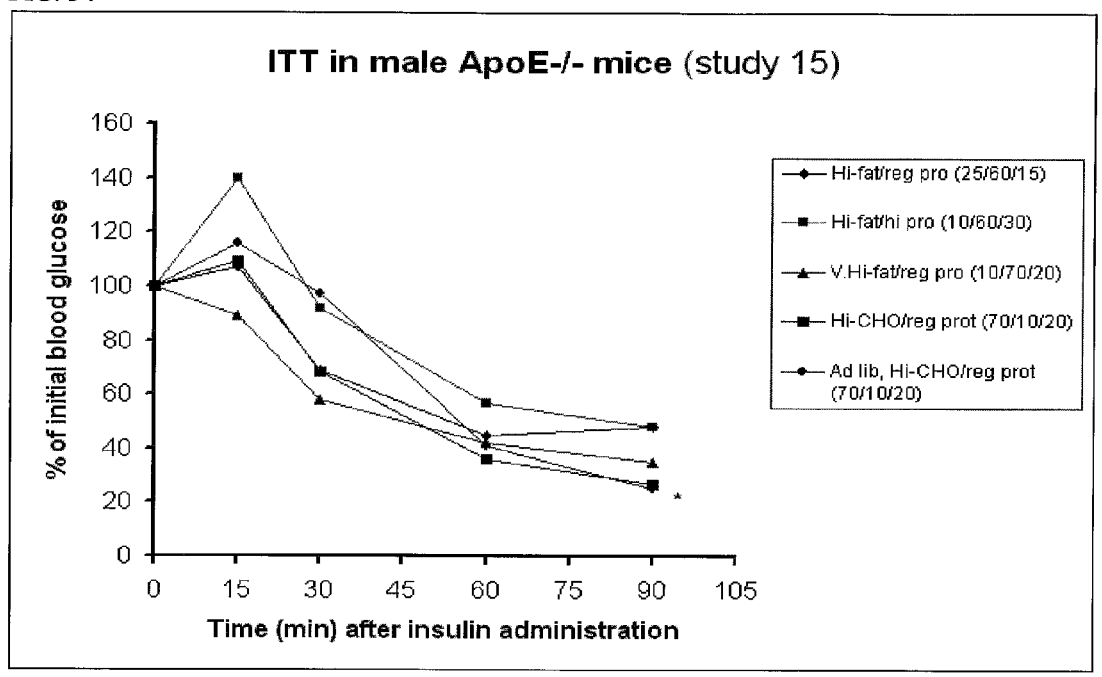
FIG. 34 graphically illustrates ITT in male ApoE−/− mice.

Fasting plasma lipids, cholesterol, oral glucose tolerance test and insulin tolerance test were conducted after 16 weeks of diet intervention. Lipid, cholesterol, and blood glucose data are shown in FIGS. 30A-B for male and female mice, respectively. Insulin tolerance test data are shown in FIGS. 32-34.

High-fat definitely increased weight gain, as in C57BL mice (especially in females) relative to the high-carbohydrate intake. High-protein did not correct weight gain in males, but it did in females. Also females were much less affected by high-fat than males, in terms of weight gain.

Very high fat had a negative effect on the cecum, reducing its size, even as it would seem to do in human large bowel function.

Blood glucose was more affected in females, whereas low-protein or very high-fat (increased fat:protein ratio) raised glucose. A high-fat diet was worse than a high-carbohydrate diet, with respect to glucose, i.e., diet carbohydrate load favored the glucose metabolic system, even as it did in the C57BL mouse.

Plasma total cholesterol tended to be higher in the high-carbohydrate diet, especially in females, even though triglycerides were lower in both sexes with high-carbohydrate. Female total cholesterol ran about 100 mg/dl lower than males on the same diet.

ITT was best with high-carbohydrate, especially in females, whereas the high-fat, high-protein and high-fat, regular protein were especially bad in males, which had the worst adipose response to fat. In essence, a high fat:protein ratio has a detrimental effect on ITT.

High fat diets are definitely a problem, even in the apoE (−/−) mouse, which tends to mimic the C57BL (Study 12). Obesity is greater with added fat, while glucose metabolism is better with higher carbohydrate. Fatness was better demonstrated in the female apoE mouse. Blood total cholesterol is consistently highest with high-carbohydrate in these studies (driven by the EC in liver, as precursor to blood pool), but that may also depend somewhat on the type of fat fed, a point that has not been explored yet (but which is underway in apoE mice).

High fat diets increased weight gain, as compared to high carbohydrate diets. The low protein diet and high fat diet increased blood glucose levels and the high fat diet had higher glucose levels than the high carbohydrate diet. The insulin tolerance was best with high carbohydrate diet, whereas the high fat/high protein and high fat/regular protein increased adipose weight. In essence, a high fat:protein ratio has a detrimental effect on insulin tolerance.

Plasma total cholesterol tended to be higher in the high carbohydrate diet, especially in females, even though triglycerides were lower in both sexes with the high carbohydrate diet. Obesity is greater with added fat, while glucose metabolism is better with higher carbohydrate diets. Blood total cholesterol is consistently highest with a high carbohydrate diet in these studies.

Study 17

C57BL/6J (obese mouse model) mice were randomized to one of 3 diets: 1) low carbohydrate (20% CHO, 40% protein, 40% fat); 2) balanced diet (33% CHO, 33% protein, 33% fat); and 3) high carbohydrate (60% CHO, 20% protein, 20% fat). Details of each diet are shown in Tables 32-33.

TABLE 32 diet compositions: Diets Substituting a 1:1 Pro:Fat Ratio for CARBOHYDRATE fed to male C57BL/6J mice

|  | Diet # | | |
| --- | --- | --- | --- |
|  | 80 Low CHO | 81 Balanced | 82 High-CHO |
| CHO:Fat:Protein % en | 20:40:40 | 33:33:33 | 60:20:20 |
| g/kg | | | |
| Casein | 240 | 192 | 108 |
| Lactalbumin | 240 | 192 | 108 |
| Dextrose | 78 | 123 | 204 |
| Cornstarch | 162 | 260 | 425 |
| Fat | | | |
| SFA:MUFA:PUFA (% en) | 13.3:13.3:13.3 | 11:11:11 | 6.7:6.7:6.7 |
| Butter fat | 29 | 23 | 14 |
| Tallow | 75 | 60 | 33 |
| Soybean | 110 | 87 | 49 |
| Fat/protein % en ratio | 0.67 | 0.45 | 0.67 |
| kcal/g diet (dry wt.) | 3.988 | 3.988 | 3.988 |
| Mineral mix (Ausman - Hayes) | 50 | 48 | 45 |
| Vitamin mix (Hayes - Cathcart) | 13 | 12 | 11 |
| Choline chloride | 3 | 3 | 3 |
| Cholesterol | 0.73 | 0.73 | 0.71 |
| Cholesterol (from fat)** | (0.15) | (0.12) | (0.07) |

*same amount of cholesterol per kcal of diet
**cholesterol provided from butter and tallow

TABLE 33

Caloric and cholesterol intakes in male C57BL/6J mice fed diets of increasing carbohydrate content

|  | Diet # | | |
| --- | --- | --- | --- |
|  | 80 Low CHO | 81 Balanced | 82 High-CHO |
| CHO:Fat:Protein % en | 20:40:40 | 33:33:33 | 60:20:20 |
| Caloric intake (kcal/mouse/day) | 12.6 ± 2.7 | 14.3 ± 1.7 | 14.9 ± 1.8 |
| Cholesterol intake (mg/mouse/day) | 2.3 | 2.6 | 2.7 |

Fasting plasma lipids, cholesterol, oral glucose tolerance test and insulin tolerance test were conducted after 16 weeks of diet intervention. Body and organ weight data are shown in Table 34. Cholesterol, triglyceride, and glucose data are shown in Tables 35-39.

Insulin tolerance was improved with a protein:fat ratio of 1:1. As the carbohydrate content decreased, the blood glucose control increased. However, the low carbohydrate diet (protein 40%) increased kidney weight, suggesting a decrease in kidney function. Therefore, the protein:fat ratio of 1:1 was best with the carbohydrate content balanced with the protein and fat in a 1:1:1 ratio.

The high carbohydrate diet increased liver triglycerides and total cholesterol levels compared to the low carbohydrate and balanced diet. No difference was noticed in the muscle triglycerides levels (See Table 36).

TABLE 34

Body and Organ Weights (expressed as % of body weight) for male C57BL/6J mice fed diets with increasing carbohydrate content and a constant 1:1 ratio of Protein:Fat

|  | Diet # | | |
| --- | --- | --- | --- |
|  | 80 Low CHO | 81 Balanced | 82 High-CHO |
| CHO:Fat:Protein % en | 20:40:40 | 33:33:33 | 60:20:20 |
| Body Wt | | | |
| Initial | 39.2 ± 4.5 | 38.9 ± 3.2 | 39 ± 2.9 |
| Final | 35.4 ± 2.1$^{a,b}$ | 39.9 ± 3.5$^a$ | 42 ± 3.7$^b$ |
| Wt Gain | (−)3.76 ± 3.4$^{a,b}$ | 1.13 ± 3.9$^a$ | 3 ± 2.3$^b$ |
| Organ Wts (% body wt) | | | |
| Liver | 3.19 ± 0.25$^b$ | 3.28 ± 0.36$^a$ | 3.96 ± 0.64$^{a,b}$ |
| Peri-renal adipose | 2.25 ± 0.65$^{a,b}$ | 3.05 ± 0.55$^a$ | 2.81 ± 0.71$^b$ |
| Epidemal Adipose | 5.72 ± 1.44$^a$ | 6.6 ± 0.94 | 6.84 ± 0.83$^a$ |
| Total Adipose | 7.97 ± 1.86$^{a,b}$ | 9.65 ± 1.30$^a$ | 9.65 ± 1.15$^b$ |
| Kidney | 1.29 ± 0.21$^a$ | 1.15 ± 0.17 | 1.01 ± 0.18$^a$ |
| Cecum | 0.69 ± 0.09$^a$ | 0.63 ± 0.11 | 0.58 ± 0.09$^a$ |
| Muscle | 0.45 ± 0.07$^a$ | 0.42 ± 0.07 | 0.38 ± 0.09$^a$ |
| Pancrease | 0.6 ± 0.26 | 0.56 ± 0.18 | 0.53 ± 0.14 |
| Heart | 0.39 ± 0.09 | 0.41 ± 0.06 | 0.38 ± 0.03 |
| Spleen | 0.21 ± 0.04 | 0.21 ± 0.02 | 0.23 ± 0.02 |

Values are Mean ± SD (n = 12 for diets 80 and 82, n = 13 for diet 81)
$^{a,b}$Means in a row with different superscripts differ (p < 0.05) by one-way ANOVA and Fisher's PLSD test

TABLE 35

Fasting plasma TOTAL CHOLESTEROL and TRIGLYCERIDES - 10 wks and 14 wks after diet intervention in male C57BL/6J mice fed diets with increasing carbohydrate content and a constant 1:1 ratio of Protein:Fat

|  | Diet # | | |
| --- | --- | --- | --- |
|  | 80 Low CHO | 81 Balanced | 82 High-CHO |
| CHO:Fat:Protein % en | 20:40:40 | 33:33:33 | 60:20:20 |
| Plasma TC | | | |
| initial | 178.1 ± 40.7 | 182.1 ± 20.3 | 179.4 ± 27.8 |
| 10 wks | 145.9 ± 24.3$^{a,b}$ | 170.8 ± 19.9$^a$ | 209.4 ± 48.6$^b$ |
| terminal | 121.8 ± 21.7$^{a,b}$ | 154.2 ± 16.3$^{a,c}$ | 181.6 ± 38.7$^{b,c}$ |
| % change from initial (using terminal values) | (−)30.3 ± 9.5$^{a,b}$ | (−)14.9 ± 8.3$^{a,c}$ | 1.4 ± 16.1$^{b,c}$ |
| Plasma TRIGLYCERIDES | | | |
| Initial | 125.2 ± 56.8 | 112.8 ± 33.4 | 133.1 ± 27.7 |
| 10 wks | 62.4 ± 24.7$^a$ | 90.4 ± 30.9$^{a,b}$ | 88 ± 17.4$^b$ |
| terminal | 96.7 ± 23.3$^a$ | 118.2 ± 23.4$^{a,b}$ | 98 ± 19.5$^b$ |
| % change from initial | (−)14.8 ± 25.4$^a$ | 11.5 ± 30.4$^{a,b}$ | (−)25.5 ± 13.8$^b$ |
| Plasma Glucose terminal | 205.5 ± 37.3$^{a,b}$ | 250.8 ± 56.7$^a$ | 252.6 ± 42.1$^b$ |

Values are Mean ± SD (n = 12 for diets 80 and 82, n = 13 for diet 81)

$^{a,b,c}$Means in a row with different superscripts differ (p < 0.05) by one-way ANOVA and Fisher's PLSD test

TABLE 36

Muscle Triglyceride Content for male C57BL/6J mice fed diets with increasing carbohydrate content and a constant 1:1 ratio of Protein:Fat

|  | Diet # | | |
| --- | --- | --- | --- |
|  | 80 Low CHO | 81 Balanced | 82 High-CHO |
| CHO:Fat:Protein % en | 20:40:40 | 33:33:33 | 60:20:20 |
| Muscle Triglyceride | 17.8 | 19.7 | 19.4 |
| (mg TRIGLYCERIDES/g liver) | ±5.6 | ±5.3 | ±6.7 |

Values are Mean ± SD (n = 12 for diets 80 and 82, n = 13 for diet 81)

TABLE 37

Liver Free Cholesterol, Cholesterol Ester and TRIGLYCERIDES Content for male C57BL/6J mice fed diets with increasing carbohydrate content and a constant 1:1 ratio of Protein:Fat

|  | Diet # | | |
| --- | --- | --- | --- |
|  | 80 | 81 | 82 |
| CHO:Fat:Protein % en | Low CHO | Balanced | High-CHO |
| liver lipids (mg/g liver) | 20:40:40 | 33:33:33 | 60:20:20 |
| FC | 2.5 ± 0.3$^a$ | 2.6 ± 0.3 | 2.7 ± 0.3$^a$ |
| EC | 0.8 ± 0.6$^a$ | 1.7 ± 0.7$^a$ | 6.0 ± 2.8$^{a,b}$ |
| TC | 3.3 ± 0.7$^a$ | 4.2 ± 0.7$^a$ | 8.8 ± 2.9$^{a,b}$ |
| liver TRIGLYCERIDES (mg/g liver) | 23.0 ± 7.5$^a$ | 42.2 ± 14.9$^b$ | 96.5 ± 35.1$^{a,b}$ |

Values are Mean ± SD (n = 12 for diets 80 and 82, n = 13 for diet 81)

$^{a,b,c}$Means in a row with different superscripts differ (p < 0.05) by one-way ANOVA and Fisher's PLSD test

TABLE 38

Terminal Plasma Chemistries - Measures of Muscle and Hepatic Injury for male C57BL/6J mice fed diets with increasing carbohydrate content and a constant 1:1 ratio of Protein:Fat (terminal plasma samples were pooled from all mice from each group for analysis)

|  | Diet # | | |
| --- | --- | --- | --- |
|  | 80 Low CHO | 81 Balanced | 82 High-CHO |
| CHO:Fat:Protein % en | 20:40:40 | 33:33:33 | 60:20:20 |
| Plasma Chem (IU/L) | | | |
| ALT (SGPT) | 24** | 43 | 19** |
| AST (SGOT) | 102* | 106* | 64 |
| CK | 492* | 455* | 209* |

*Means value is above normal clinical values for male C57BL/6J mice
**Means value is below normal clinical values for male C57BL/6J mice

TABLE 39

Terminal Plasma Chemistries - Measures of Renal Function for male C57BL/6J mice fed diets with increasing carbohydrate content and a constant 1:1 ratio of Protein:Fat

|  | Diet # | | |
| --- | --- | --- | --- |
|  | 80 Low CHO | 81 Balanced | 82 High-CHO |
| CHO:Fat:Protein % en | 20:40:40 | 33:33:33 | 60:20:20 |
| BUN (mg/dL) | 24 | 24 | 30 |
| Creatinine (mg/dL) | 0.3 | 0.3 | 0.2** |
| B/C Ratio | 80 | 80 | 150* |
| Sodium (mEq/L) | 168* | 168* | 162* |
| Potassium (mEq/L) | 6.9 | 6.7 | 6.5 |
| Na/K Ratio | 24 | 25 | 25 |
| TCO2 (mEq/L) | 21 | 20 | 21 |
| Phosphorus (mg/dL) | 6.6 | 7.6 | 6.7 |

*Means value is above normal clinical values for male C57BL/6J mice
**Means value is below normal clinical values for male C57BL/6J mice Correlation Between Diabetes and Risk Factors for Cardiovascular Disease Diabetes and cardiovascular disease (CVD) and/or coronary heart disease (CHD) share a number of risk factors. For example, individuals with high blood pressure (i.e., >140/90 mmHg), a known CVD risk factor, are at a greater risk for developing Type 2 diabetes than are individuals having normal blood pressure. Similarly, individuals with high density lipoprotein cholesterol (HDLC) levels of 35 mg/dL or less or triglyceride (TG) levels of 250 mg/dL or more, both known risk factors for CVD, are also at an increased risk for developing Type 2 diabetes.

In addition, diabetes itself may be considered a risk factor for CVD, as it has been shown that persons with Type 2 diabetes have a high incidence of death at time of acute myocardial infarction and have a relatively poor prognosis for long-term survival after myocardial infarction. The data above suggest, therefore, that it is advisable to treat an individual with diabetes as though he or she was at increased risk for CVD, even if the individual does not have other CVD risk factors.

Supplemented Intensive Insulin Therapy

Tight glycemic control and the use of supplementing specific nutrients has benefits above what can be derived from the use of either alone. The results of the studies above provide valuable information not only for the prevention and/or treatment of diabetes and its comorbidities, but for other indications where glycemic control may be beneficial. For example, recovery from physical trauma (e.g., surgery, burns, etc.), cancer, obesity, and chronic disease (e.g., chronic respiratory disease, ulcers, etc.) has been shown to be improved by "tight" glycemic control. Typically, such glycemic control includes the administration of a low glycemic carbohydrate source. Often, glycemic control includes intensive insulin therapy.

Surprisingly, it has been found that the supplementation of intensive insulin therapy promotes glutamine synthesis, but when used in combination with one or more branched chain amino acids (BCAA) and/or glutamine/glutamate it promotes protein synthesis, potentially aiding recovery from any number of conditions, including physical trauma, cancer, obesity, and chronic disease. Preferably, the nutritional supplementation further includes a slowly digested and/or metabolized sugar. Suitable sugars include, for example, isomalt, isomaltulose, trehelose, D-tagatose, tapioca dextrin, and sucromalt.

Supplementations such as those above have been shown to improve insulin sensitivity and reduce blood and/or plasma glucose concentrations, allowing a better metabolic response, including improved nitrogen balance and endogenous protein synthesis. Experimentally, intensive insulin therapy including amino acid supplementation was shown to: increase plasma concentrations of leucine (129 v. 112 μmol/L) and glutamine (381 v. 248 μmol/L); reduce the circulating concentration of glucose (109 v. 173 mg/dL); improve protein net balance (−3 v. −11 nmol Phe/min/100 mL leg volume) and protein synthesis (42 v. 21 nmol Phe/min/100 mL leg volume); decrease leucine oxidation (15 v. 32 nmol/min/100 mL leg volume); and increase de novo glutamine synthesis (94 v. 41 nmol/min/100 mL leg volume).

Muscle glutamine is reportedly depressed in post-surgical patients and in those with chronic disease. As such, increasing glutamine content in the patient would be expected to improve their condition. More broadly, because glycemic control is a beneficial goal in patients recovering from physical trauma or undergoing surgery, the administration of an enteral or sip-fed nutritional composition comprising a low glycemic carbohydrate source, BCAAs, and glutamine and/or glutamate has the potential to improve the recovery of such patients through increased protein synthesis.

Supplementation of Nutritional Formula with 1:1:1 Carbohydrate:Protein:Fat Ratio As described above, a nutritional formula having a 1:1:1 carbohydrate:protein:fat ratio is beneficial in treating or managing diabetes and/or its comorbidities (e.g., cardiovascular disease, renal disease, etc.). The higher protein content aids in early insulin release. In addition, both the higher protein content and the lower carbohydrate content help in the management of blood glucose levels.

However, a nutritional formula having a 1:1 protein:fat ratio may be further supplemented with one or more ingredients useful in improving glycemic control, treating diabetes, its comorbidities, or symptoms thereof. Such ingredients include Touchi Extract, partially hydrolyzed guar gum, inulin, fructooligosaccharides, galactooligosaccharides, isomaltulose, slowly digestible carbohydrates, lipoic acid, fenugreek, 4-hydroxyisoleucine, green tea leaves and extracts, cinnamon, banaba extract, syzygium cumini seeds, arginine, fish oil, chlorogenic acid, mangosteen, palm fruit juice, chromium, and vanadium. It is believed that the use of two or more of such ingredients, with or without a nutritional formula having a 1:1 protein:fat ratio, will yield additive or synergistic results in delaying the appearance of glucose in the blood, lowering post-prandial plasma insulin levels, lowering glucose resistance, and/or increasing glucose sensitivity. Physiological and other characteristics of such ingredients are described below. Further It is believed that the use of two or more of such ingredients, with or without a nutritional formula having a 1:1 protein:fat ratio, will yield additive or synergistic results in treating or preventing cardiovascular disease or incident. Physiological and other characteristics of such ingredients are described below.

Touchi Extract

Touchi Extract (TE) is a water-extract powder of fermented soybeans. TE is derived from soybeans that have been fermented with Aspergillus Oryzae. TE has been shown to inhibit α-glucosidase activity leading to lower blood glucose levels and HbA1c values in individuals with Type 2 diabetes, similar to Acarbose and Voglibose. TE inhibits α-glucosidase exclusively and does not inhibit other digestive enzymes like amylase, pepsin, trypsin, chymotrypsin or lipase. Due to its ability to inhibit carbohydrate absorption, it is proposed that TE will act to increase the plasma concentration of glucagon-like peptide-1 (GLP-1) and glucagon-like peptide-2 (GLP-2).

GLP-1 is a hormone that is secreted from the endocrine L cells located in the distal small intestine and colon. GLP-1 acts to stimulate glucose-dependent insulin secretion, and beta cell proliferation and neogenesis. GLP-1 is secreted in response to nutritional, hormonal and neural stimulation, with the primary stimulus being enteral nutrition. TE is a natural α-glucosidase inhibitor that inhibits the breakdown of carbohydrates, prolonging the time carbohydrates are present in the intestine. Therefore, a greater amount of carbohydrates may reach the distal small intestine and interact with the L cells to stimulate GLP-1 secretion. The increased plasma concentration of GLP-1 will improve glycemic control in addition to the effect from TE in delaying the appearance of glucose in the blood.

GLP-2 is a hormone that is secreted from the endocrine L cells located in the distal small intestine and colon. GLP-2 acts to enhance intestinal structure and function by improving crypt-villus architecture and increasing enzyme and transporter activities. GLP-2 is secreted in response to nutritional, hormonal and neural stimulation, with the primary stimulus being enteral nutrition. TE is a natural α-glucosidase inhibitor that inhibits the breakdown of carbohydrates, prolonging the time carbohydrates are present in the intestine. Therefore, a greater amount of carbohydrates may reach the distal small intestine and interact with the L cells to stimulate GLP-2 secretion. The increased plasma concentration of GLP-2 will improve intestinal structure and function and reduce intestinal inflammation.

Benefiber

Benefiber (partially hydrolyzed guar gum) is a unique functional fiber that is extracted from guar gum. The original high viscosity of guar gum is nearly eliminated after hydrolysis, making it an ideal addition to liquid foods and nutritional formulas. The chain length of Benefiber can be as high as 600 galactomannon units linked together, but the majority of Benefiber has an average chain length between 80 and 200. Many of the beneficial effects of Benefiber are likely due to its ability to be completely fermented in the colon and produce significantly more butyrate than other soluble fibers. Butyrate may act on the L cell to increase the expression of proglucagon, the gene that codes for GLP-1 and GLP-2, thus providing additional GLP-1 and GLP-2 to be secreted when stimulated by enteral nutrients. The combination of TE with Benefiber will have an additive effect on increasing the plasma concentration of GLP-1 and GLP-2.

The incorporation of TE along with Benefiber in a nutritional formulation will increase GLP-1 and GLP-2 plasma concentrations and improve glycemic control and intestinal structure and function and reduce intestinal inflammation. Furthermore, this effect could enhance the potential actions of pharmacological agents that inhibit dipeptidyl peptidase-IV, the protease that degrades GLP-1 and GLP-2. The additive effect of TE and Benefiber to increase the plasma concentration of GLP-1 and GLP-2 along with the inhibition of dipeptidyl peptidase-IV would further improve glycemic control and intestinal structure and function.

In addition, a number of studies have shown that Benefiber is beneficial in maintaining bowel function, helping in the management of both diarrhea and constipation, especially in patients receiving enteral nutrition and other populations sensitive to intestinal intolerance.

The use of Benefiber would have additional beneficial effects as it is completely fermented and produces substantial amounts of butyrate. Benefiber should be included in the formula in a range of 1 to 10 g per serving (based on 240 ml per serving).

The total amount of TE provided per serving (based on 240 ml per serving) should be between 0.1 to 10 g. This would allow for a range that includes the minimum effective dose to the dose where the beneficial effect reaches a plateau.

Foods that are low in glycemic index can lead to decreased insulin-like growth factor-1 (IGF-1) that can lead to a decreased incidence and progression of cancer. TE decreases the available carbohydrate so it decreases the insulin response and decreases the glycemic response. Therefore, TE may be able to decrease the incidence and progression of cancer as it decreases the glycemic response following the consumption of foods containing carbohydrates.

Soluble Fiber Blends—Inulin and Benefiber

Inulin consists of medium-length chains of β-D fructans linked by β-2-1 linkages. It is a natural food ingredients commonly found in dietary foods including chicory, artichokes, asparagus and onion, as well as extracted from chicory roots. Inulin is readily water-soluble and exhibit sweetness that decreases with increasing chain length. Inulin can be prepared from hot water extraction of chicory roots and has a degree of polymerization of up to 60 with an average chain length of 12 to 25. Inulin is a highly fermentable fiber with a strong prebiotic activity. Numerous in vitro and human studies have indicated that inulin has specific bifidogenic effects. Like Benefiber, some studies have shown that inulin can reduce the risk of diarrhea.

The combination of inulin and Benefiber may have a greater effect on gut health than either one alone. Each fiber has a distinct fermentation rate and specific intestinal regions of activity. The prebiotic potential of inulin is stronger than Benefiber. However, Benefiber produces more butyrate. When a blend of inulin and Benefiber is consumed, the fermentation time in the intestinal tract would be lengthened, producing a greater variety of short-chain fatty acids (SCFA; acetate, propionate and butyrate) and a blend of the two fibers may enhanced the growth of beneficial bacterial strains, bifidobacteria and lactobacilli, better than or equivalent to either fiber alone.

Soluble Fiber Blends—FOS and GOS

Fructooligosaccharides are short- and medium-length chains of β-D fructans linked by β-2-1 linkages. Inulin and oligofructose are classified as fructooligosaccharides. They are natural food ingredients commonly found in dietary foods including chicory, artichokes, asparagus and onion, as well as synthesized from sucrose or extracted from chicory roots.

Inulin and oligofructose are readily water-soluble and exhibit sweetness that decreases with increasing chain length. Inulin can be prepared from hot water extraction of chicory roots, and oligofructose is obtained by partial enzymatic hydrolysis of inulin. Thus, inulin and oligofructose differ from each other by their chain length or degree of polymerization. Oligofructose, commonly referred to as FOS, has a degree of polymerization of less than 9 with an average chain length of 3 to 5, and inulin has a degree of polymerization of up to 60 with an average chain length of 12 to 25. FOS is a highly fermentable fiber with prebiotic activity, that stimulates the growth of bifidobacteria and lactobacilli. Like Benefiber, studies have shown that FOS can prevent or alleviate constipation and diarrhea.

Galactooligosaccharides (GOS) are non-digestible carbohydrates that are produced from lactose by an enzymatic reaction. They serve as substrates for endogenous colonic bacteria and are highly fermentable in the colon. GOS stimulate the growth of gut bifidobacteria and lactobacilli, increase SCFA concentrations and decrease colonic pH; therefore, they are considered strong prebiotics and are beneficial for the gastrointestinal environment.

The combination of FOS and GOS is reported to have a greater prebiotic effect on gut health than if either one was used alone due to their synergistic effect on promoting the growth of beneficial bacteria. A blend of FOS and GOS significantly increases the growth of bifidobacteria and lactobacilli more than either one alone. In addition, the SCFA production and substrate assimilation is also enhanced by the blend.

Numerous studies have examined the effect of a FOS and GOS blend on enhancing intestinal bacteria and improving stool characteristics in infants. Results indicate that the blend promotes beneficial intestinal bacteria in a synergistic way so that a maximum number of different species, especially bifidobacteria and lactobacilli, can grow. In addition, it has been reported that the blend of FOS and GOS also increases the production of SCFA and stool frequency, and significantly softens the consistency of stools.

In addition, butyrate may act on the L cell to increase the expression of proglucagon, the gene that codes for GLP-1 and GLP-2, thus providing additional GLP-1 and GLP-2 to be secreted when stimulated by enteral nutrients.

Lowering Postprandial Glycemia (Blood Sugar)

The addition of viscous dietary fiber and isolated viscous fibers to a carbohydrate-containing meal has been found to result in significant improvements in blood glucose and insulin responses in numerous controlled clinical trials. Large, rapid increases in blood glucose levels are potent signals to the beta-cells of the pancreas to increase insulin secretion. Over time, recurrent elevations in blood glucose and excessive insulin secretion are thought to increase the risk of developing type 2 diabetes mellitus (DM) as well as cardiovascular disease (see Disease Prevention below).

When the carbohydrate content of two meals is equal, the presence of fiber, particularly viscous fiber, generally results in smaller but more sustained increases in blood glucose and significantly lower insulin levels.

Type 2 Diabetes Mellitus

Increasing intakes of refined carbohydrates and decreasing intakes of fiber in the US have paralleled the increasing prevalence of type 2 diabetes mellitus (DM) to near epidemic proportions. Numerous prospective cohort studies have found that that diets rich in fiber, particularly cereal fiber from whole grains, are associated with significant reductions in the risk of developing type 2 DM. Although no intervention trials have evaluated the effect of increasing dietary fiber intake alone on type 2 DM prevention, two important intervention trials found that a combination of lifestyle modifications that included increasing fiber intake decreased the risk of developing type 2 DM in adults with impaired glucose tolerance. Although multiple factors, including obesity, inactivity and genetic factors, increase the risk of developing type 2 DM, the results of observational studies and intervention trials indicate that fiber-rich diets improve glucose tolerance and decrease the risk of type 2 DM, particularly in high-risk individuals.

Isomaltulose

Isomaltulose is a naturally occurring disaccharide that has similar physical characteristics to sucrose, thus it is a potential alternative to sucrose. The most important distinction between isomaltulose and sucrose is the fact that isomaltulose is hydrolyzed by intestinal enzymes at a slower rate than sucrose. This leads to a slower rise in blood glucose, fructose, and insulin levels in both healthy and diabetic subjects. One study reported that in healthy subjects blood glucose gradually increased to its peak of 110.9±4.9 mg/dl at 60 min after administration of 50 g of isomaltulose, while 50 g of sucrose caused a glucose peak of 143.3±8.8 mg/dl at 30 min and a rapid decrease to the fasting level. A similar response was also noted in diabetic subjects. The plasma glucose level gradually increased to its peak level (195±14 mg/dl) at 120 min after isomaltulose ingestion. In contrast, after sucrose ingestion, a peak level of 237±12 mg/dl was reached within 60 min. In addition, the change in insulin concentration was significantly smaller with isomaltulose (41.1±7.4 pµU/ml) compared to sucrose ingestion (59.3±12.0 µU/ml).

Another study examined the short- and long-term effects of an isomaltulose-based formula on carbohydrate and lipid metabolism in rats. The short-term effects revealed that plasma glucose levels were lower in the rats receiving the isomaltulose-based formula compared to the dextrin-based standard formula at 15 and 30 min after administration. In addition, the area under the curve was smaller for the isomaltulose-based formula (162.0±14.2 mmol×min/L) compared to the dextrin-based standard formula (279.5±28.5 mmol× min/L). The insulinogenic index did not differ among the groups, indicating that isomaltulose-based formulas may not affect early phase insulin response. After two months of the isomaltulose-based formula administration, body weight did not differ, but serum triglycerides (0.54±0.04 vs. 1.31±0.12 mmol/L) and insulin (50.2±3.7 vs. 74.2±2.0 µmol/L) levels were decreased along with improved insulin sensitivity in peripheral tissues (0.94±0.03 vs. 0.76±0.03 mmol/kg/min). The weight of epididymal, mesenteric and retroperitoneal adipose tissue were lower in the group receiving the isomaltulose-based formula, but weights of the liver and pancreas were increased. The authors concluded that these results are primarily due to the low-glycemic index and improved glycemic control induced by isomaltulose.

Interestingly, a recent report indicates that isomaltulose can increase mental concentration in adults. The authors concluded that isomaltulose significantly increased mental concentration in adults in the same way as sucrose, but that the effect of isomaltulose tended to last longer. The minimum effect dose was estimated to be more than 5 g. Additional studies are being done to determine the mechanism for the isomaltulose effect.

Isomaltulose is slowly and completely digested in the small intestine, providing a slower blood glucose and insulin response. This characteristic of isomaltulose is potentially beneficial and may support its use in diabetic products.

Slowly Digestible Carbohydrate Sources

Nutritional formulations that include carbohydrates that are slowly digestible are important for helping individuals with diabetes manage blood glucose but they also increase the amount of carbohydrate that reaches the distal portion of the small intestine leading to increased contact of the L cell with carbohydrates and potentially an increase production of GLP-1 and GLP-2. Sucromalt and Trehalose have similar characteristics to isomaltulose and have the same potential to improve glucose management in individuals with diabetes. Sucromalt is derived from sucrose and maltose. Trehalose is composed of two glucose units and one glucose molecule is upside-down relative to the other. In addition, other carbohydrates that are slowly absorbed could be contained within the nutritional formulation.

In addition, butyrate may act on the L cell to increase the expression of proglucagon, the gene that codes for GLP-1 and GLP-2, thus providing additional GLP-1 and GLP-2 to be secreted when stimulated by enteral nutrients.

Lipoic Acid

Lipoic acid (LA) has been reported to improve the removal of glucose from the blood of diabetics and also to prevent tissue damage through antioxidant action. It has also been claimed that the use of LA reduces pain associated with polyneuropathy, a troubling condition in which diabetes is the most common cause of peripheral nerve damage.

LA may be a racemic mixture of R- and S-stereoisomers. The bioavailability of (R)-LA is reported to be greater than (S)-LA. In addition, animal research has shown the R-stereoisomer to be more effective than either S- or the racemic mixture of LA on improving insulin sensitivity. The overall bioavailability of 600 mg LA has been shown to be reduced with the ingestion of food, suggesting that for maximum efficacy of low dose-LA it should be administered while the stomach is empty.

Supplementing the diets of spontaneously hypertensive rats with LA (500 mg LA/kg diet) lowered both blood glucose and insulin levels, systolic blood pressure, and cytosolic $[Ca^2]i$. Streptozotocin-induced (STZ) diabetic rats diets were supplemented with LA (400 mg LA/kg) and after a period from 4 to 7 mo., blood glucose was significantly lower in LA rats versus non-treated control, but there was no difference between rats treated with LA or insulin. As a result, it was reported that prolonged supplementation of the diet of STZ-diabetic rats with LA was necessary for attenuation of hyperglycemia. Furthermore, supplementing LA into diets for STZ-induced diabetic rats resulted in a peripheral insulin-sensitizing effect as demonstrated by a 13% reduction in the area under the glucose curve following intravenous insulin tolerance testing. Supplementing diets with LA (30 mg LA/kg BW) for STZ-induced diabetic rats increased renal cortical glutathione content above other antioxidants. LA was reported to be an effective tool in the prevention of glomerular diabetic injury.

An uncontrolled study with 20 Type 2 diabetics showed that 1200 mg LA (oral) for 4-wks improved measures of glucose metabolism. Following LA treatment, lactate and pyruvate were reduced by 45% after oral glucose loading. Orally, LA acid is reported to be safe at up to 1800 mg/d given as 3 doses of 600 mg LA. In another pilot study with 20 Type 2 diabetics, oral administration of 600, 1200 and 1800 mg/d LA improved insulin-stimulated glucose disposal as compared to placebo control. Insulin sensitivity was reported to have improved 17% with LA treatment. There were no observed differences among the three concentrations of LA. This may indicate no additional benefits above 600 mg LA/d.

Diabetic patients given a tablet of LA (600 mg/d) for 3 mo. were reported to have less oxidative stress as measured by the ratio of plasma lipid peroxides/(Vit E/Cholesterol). No correlation between glycemic control and lipid peroxides or the ratio of lipid peroxides to (Vit E/cholesterol) was observed.

The evidence presented here suggests that lipoic acid supplementation may provide an additional benefit through improving measures of glucose metabolism and also improve blood glucose regulation.

4-Hydroxyisoleucine (Fenugreek Seed)

Previously, research with fenugreek (Trigonella foenumgraecum) seeds investigated the effect of its soluble fiber fraction (specifically galactomannan) on control of elevations in blood glucose associated with diabetes. However, the amino-acid (4-hydroxyisoleucine; aka ID-1101) is another bioactive component of fenugreek seeds that also appears to have a positive effect on glucose control in non-insulin dependent diabetics.

Fenugreek seeds have been reported to contain between 20 and 30% protein and approximately 50% as carbohydrate, in the form of dietary fiber. The amino acid extracted from fenugreek seeds (ID-1101) is of particular interest because it is solely produced by fenugreek plant and is a non-proteinogenic-branched-chain amino acid.

The action of ID-1101 is believed to work through two separate and essential dysfunctions of Type 2 diabetes. These mechanisms include (1) improvement of insulin response to glucose in pancreatic beta-cells and (2) enhanced insulin activation of insulin receptor substrate (IRS) and phosphoinositol (PI) 3-kinase in extrapancreatic tissues.

Several animal research trials have investigated the glycemic control effect of fenugreek and its extracts. In a recent study, obese, insulin-resistant Zucker fa/fa rats given 100 mg/kg ID-1101 for 3-weeks had reduced hyperinsulinemia compared with the progressive increase in control obese rats (P<0.05). The authors concluded that ID-1101 exerts insulin-sensitizing effects independently of its insulinotropic effects.

Fenugreek whole seed powder (5% in the diet) was administered to alloxan-induced diabetic Wistar rats for three weeks and returned elevated fasting blood glucose to control concentrations. The therapeutic role of fenugreek in Type 1 diabetes can be attributed to the change of glucose and lipid metabolizing enzyme activities to more normal values, thus stabilizing liver and kidney glucose homeostasis.

The effects of fenugreek on diabetes in a canine model was addressed using two subfractions: subfraction-A: testa and endosperm fraction; rich in fibers (79.6%) and subfraction-B: cotyledons and axes; rich in saponins (7.2%) and proteins (52.8%). Each subfraction was given to dogs mixed with two daily meals. Subfraction-a and insulin treatment decreased hyperglycemia, glycosuria, high plasma glucagon and somatostatin levels. Subfraction-A also decreased the hyperglycemic response to the oral glucose tolerance test. In contrast, Subfraction-B had no effect on hyperglycemia or pancreatic hormones in diabetic dogs. The antidiabetic properties of fenugreek seeds are believed to be in testa and endosperm and although this subfraction is rich in fibers (high viscosity; 115 cP), it is not possible to exclude the existence of one or more unknown active pharmacological compounds in this subfraction of the seed (Ribes et al. 1986).

Fenugreek administered orally at 2 and 8 g/kg dose to normal and alloxan induced diabetic rats produced a significant fall (P<0.05) in blood glucose both in the normal as well as diabetic rats and the hypoglycemic effect was dose related (Khosla et al. 1995).

The hypoglycemic effects of a decoction and an ethanol extract of Trigenolla foenum graceum seeds on the serum glucose levels of normal and alloxan diabetic mice were studied. A single 0.5 ml oral dose of 40-80% decoctions to normal as well as alloxanized mice was followed by hypoglycemia developed over a 6-h period. Reduction in blood glucose concentration was highly significant, was maximum at 6 h and was dose-dependent. The hypoglycemia caused by the ethanol extract (200-400 mg/kg) in alloxanized mice was also dose-dependent and 200 mg/kg was comparable in effect to 200 mg/kg tolbutamide.

Extract of fenugreek seeds was orally administered to sub-diabetic and mild diabetic rabbits (n=5) at 50 mg/kg BW for 15 d. Treatment significantly attenuated the glucose tolerance curve and improvement in the glucose induced insulin response, suggesting the hypoglycemic effect is mediated through stimulating insulin synthesis and/or secretion from beta cells. Prolonged administration at 50 mg/kg BW for 30 d to severely diabetic rabbits (n=5) significantly lowered fasting blood glucose, but could elevate the fasting serum insulin level to a much lower extent, which suggests an extra-pancreatic mode of action for the active principle. The effect may also be by increasing the sensitivity of tissues to available insulin. The hypoglycemic effect was observed to be slow but sustained, without any risk of developing severe hypoglycemia.

Because 4-hydroxyisoleucine and isoleucine may have the same mechanism of action, a very brief overview of oral administration of isoleucine on glucose uptake is presented. Oral isoleucine (0.3 g/kg BW) has been reported to decrease plasma glucose in 7-wk old rats, as compared to leucine and valine treatments. Branched chain amino acids have been shown to stimulate secretion of insulin. Leucine and isoleucine used together at a physiological concentration (0.25 mmol/l each) are reported to double insulin secretion from the pancreas. Stimulation of insulin release by branched chain amino acids (BCAA) was commensurate with the increase in $O_2$ consumption and coincided with an increase in the islet NADPH/NADP+ ratio, net uptake of $^{45}Ca$, and cyclic AMP concentration. Therefore, insulin release through BCAAs is causally linked to an increase in catabolic fluxes and secretagogues acting in the islet cells as fuel (glutamine) or an enzyme activator. Fenugreek, in summary, appears to exert modest, but significant, effects to improve glycemic control as determined by review of animal research data. Thus, Fenugreek and its components may provide benefits when incorporated into a nutritional regimen designed to address diabetic-related dysfunctions.

Catechins (EGCG)/Green Tea on Diabetes

Green tea is rich in polyphenolic compounds that may make up to 30% of dry tea weight and include the flavonols or "catechins." Comparison of the effects of various catechins tested on glucose transport from erythrocytes indicates that gallation of epigallocatechin (EGC) to epigallocatechin gallate (EGCG) increases its affinity for the glucose transporter by 2 to 4 orders of magnitude. Thus, EGCG is thought to have the greatest bioactive potential of the catechins. Although most experimental data focuses on the role of specific catechins (EGCG), the major effects observed in vivo are suggested to require the combined actions of several compounds found in tea and not just one.

Several mechanisms have been proposed as to how the tea catechins act on diabetes. Inhibition of glucose uptake from the intestine is one mechanism proposed to reduce blood glucose. Evidence supporting the inhibitory activity of catechins on glucose transport includes reduction in mucosal glucose uptake and portal plasma glucose concentration by green tea extract. In addition, tea extract also decreased $Na^+$—$K^+$ ATPase activity. Therefore, it is believed that glucose transport was inhibited and the reduction in $Na^+$ extrusion from enterocytes by eliminating the gradient necessary for $Na^+$-assisted glucose transport. 'Gallated' polyphenols (EGCG vs EGC) are thought to be the active form because both gallic acid and EGC alone have little inhibitory activity on glucose transport. Therefore, it is believed that the catechin component of the compound may increase access of the galloyl residue to the binding sites of glucose transporters to promote inhibition.

Another proposed mechanism is an insulin-like action of EGCG because it has been shown to increase insulin receptor tyrosine phosphorylation and receptor substrate-1 (IRS-1) and reduce PEPCK gene expression in a PI 3-kinase-dependent manner. EGCG also mimics insulin by increasing PI 3-kinase.

High doses of green tea catechins, enough to raise plasma EGCG to 1 mM, reduced the elevation of serum glucose concentrations in normal rats challenged with gavaging 2 g glucose/kg BW. In addition, catechins (20-50 µM) also reduced plasma glucose in alloxan-treated rats.

Feeding rats Teavigo™ (>90% crystalline EGCG) supplemented diets (1%) for 5 weeks resulted in a dose dependent decrease in both fed and fasted blood glucose concentration by −57 and −50%, respectively. An 11 day study using gavage with Teavigo (30 and 100 mg/kg/d) also resulted in a decrease in fasted blood glucose by −16% and −32%, respectively. Oral glucose tolerance improved by 7% and 19%). Plasma insulin increased and there was also a decrease in liver mRNA for gluconeogenic enzymes (PEPCK & G6Pase).

Green tea extract was observed to have an anti-hyperglycemic effect in fasting STZ-induced diabetic mice at 300 mg/kg, but not at 30 or 150 mg/kg. There was no change in blood insulin concentrations during the fall in blood glucose concentrations. The author speculates that the mechanism of green tea compounds on blood glucose concentration is to promote insulin action in peripheral tissues.

Supplementing the water with green tea (0.5 g lyophilized tea/100 ml) in fructose-fed rats exhibiting insulin resistance improved the insulin-stimulated glucose uptake and also increased the presence of GLUT4 on adipocytes. The author summarized that green tea ameliorated insulin resistance possibly through increased expression of GLUT4.

Alloxan-induced diabetic rats dosed with "Epicatechin" (30 mg/kg i.p.—2X/d) for 4-5 days decreased blood sugar concentrations to normal and histology showed regeneration of β-cells necrosed by alloxan. Immunoreactive insulin studies showed the cells to be functional.

Sheehan et al. (1983) also dosed alloxan-treated rats with 30 mg/kg epicatechin and reported that epicatechin may be useful in protecting against alloxan toxicity to β-cells, but was not useful in reversing existing diabetes. In agreement with Sheehan et al., Bone et al. (1985) also investigated claims that epicatechin reversed alloxan-induced diabetes in rats and found no indications that it could halt the onset or reverse established diabetes. Differences in results were thought to be related to the poor stability of epicatechin, but analysis showed it stable for at least 5 days in solution.

The pre-clinical findings suggest that the anti-diabetic effects of EGCG and the tea catechins are the result of inhibition of intestinal glucose transport ($Na^+$-Glucose transporter). An additional view is that high EGCG (>10 µM) prevents hyperglycemia by inhibiting gluconeogenesis (e.g. PEP-kinase). However, it is important to note that the concentrations of catechins used in these pre-clinical trials are likely higher than achievable in humans and difficult to obtain through oral supplementation alone.

Ten healthy volunteers ingested 1.5 mmole EGCG. EGCG had an elimination T1/2 of 3.9 h. At 24 h, EGCG had returned to base levels. Peak maximum for EGCG was 1.3 µmol. $l^{-1}$. Very limited interconversion (EGCG to EGC) occurred indicating that degallation is not required for uptake. EGCG was not detected in the urine. No statistically significant increase in plasma antioxidant activity was found with EGCG.

Cinnamon

Cinnamon is derived from the inner bark of a tropical evergreen tree. The two main varieties are *Cinnamomum cassia* and *Cinnamomum zeylanicum*. *C. cassia* is an aromatic bark, similar to *C. zeylanicum*, but differing in strength and quality. *C. cassia* bark is darker, thicker and coarser. The corky outer bark often accompanies this variety. *C. zeylanicum* is also known as Ceylon cinnamon or 'true cinnamon' which is a lighter color and possessing a sweeter, more delicate flavor than *C. cassia*.

Cinnamon has been shown to contain methylhydroxychalcone polymer (MHCP). This polymer inhibits protein tyrosine phosphatase-1B, which dephosphorylates a phosphopeptide that encompasses the autophosphorylation domain of the insulin receptor β-subunit on Tyr-1150 or Tyr-1151. Therefore, MHCP mimics the actions of insulin by allowing phosphorylation of the insulin receptor and reduces blood glucose levels. Cinnamon may be beneficial for individuals with insulin resistance, as cinnamon may stimulate the necessary cascade to increase glucose uptake.

Banaba Extract

*Lagerstremia speciosa* L., also known as Banaba, is a plant grown in tropical countries including the Philippines, India, Malaysia, China, and Australia. Leaves of this tropical plant have been used as a folk medicine for the treatment of diabetes and kidney disease. The leaves contain a large amount of corosolic acid, which as been shown to possess anti-diabetic properties and significant amounts of tannins.

The effect on blood glucose level due to decoction of banaba leaves was investigated as early as 1940 by Garcia. Later, the hypoglycemic effect of extract of *Lagerstremia speciosa* L. was evaluated by Kakuda et al. in 1996, in a diabetic mouse model (Type 2). The animals were fed for 5 weeks with a diet containing extracts from *Lagerstremia speciosa* L. Results showed that the elevation of plasma glucose level in diabetic mice was suppressed by the addition of HWE (hot water extract) or HPME (methanol eluent fraction) to the control diet, accompanied with a decrease water intake.

Moreover, the serum insulin level measured at 5th week of feeding period was decreased in the HWE diet group.

In another study, banaba extract (BE) has been used to examine its antiobesity effect. When 5 week old female KK-Ay mice were fed a test diet containing 5% of a hot-water extract from banaba leaves instead of cellulose for 12 wk, their blood glucose levels were not suppressed but they showed a significant decrease, to 65% of the control level in total hepatic lipid contents. This decrease was due to a reduction in the accumulation of triglyceride.

In 2003, Judy et al., performed a randomized clinical trial involving Type 2 diabetics patients (non-insulin-dependent diabetes mellitus, NIDDM). Subjects received a daily oral dose of Glucosol™ (extract from the leaves of Lagerstroemia speciosa standardized to 1% corosolic acid) in a soft gel or in a hard gelatine capsule form for 2 weeks. A statistically significant reduction in blood glucose level was observed in Type 2 diabetic patients receiving 48 mg per day of Glucosol supplied in soft or hard gel form. Nevertheless, the soft gel form was more effective in reducing blood glucose as it showed a 30% decrease in blood glucose vs 20% with the hard gel form.

In a recent in vitro study, the effects of BE on glucose transport and adipocyte differentiation in 3T3-L1 cells were studied. They showed that both hot-water and methanol extracts but not the extract eluted with distilled water, stimulated glucose uptake in 3T3-L1 cells, suggesting that the effective component(s) in BE is water soluble and heat stable (tested during extract preparation which need to be boiled and heat evaporated). The greatest glucose uptake was observed within 0.1 to 0.25 g/L of BE (240 nmol/L of insulin induced the greatest uptake of glucose, which is 2.7 times more than the maximum uptake observed with BE). Similar to Insulin, BE need at maximum 15 minutes to induce maximum glucose uptake. In this study they checked whether an additive or synergic effect existed between BE and Insulin but glucose uptake was not different from that of insulin alone indicating no additive or synergic effect.

Insulin has the propriety to induce differentiation of preadipocytes into adipocytes. This effect was checked in the presence of BE. Results showed that in contrast to insulin, 1-100 mg of BE induced a time and dose-dependent inhibition of IBMX- or DEX-(cocktails containing insulin that induce differentiation of preadipocyte into adipocytes) preadipocytes. Moreover, Liu et al. investigated the inhibition of the differentiation pathway, and observed that BE greatly inhibits mRNA expression of PPARγ2 in a dose-dependent manner and decrease production of GLUT4 (PPARγ2 and GLUT4 are markers of differentiation).

This group of researchers continued the investigation on the identity of the component in BE responsible for the glucose transport stimulation and inhibition of adipocyte differentiation in 3T3-L1 cells. They reported that the 2 activities of interest of BE reside in the tannin fraction of BE.

They performed further experiments with tannic acid (TA), a mixture of several structurally related gallotannin compounds purchased from Sigma and observed that TA stimulates glucose transport with a profile similar to that of insulin suggesting a potentially similar pathway. Using inhibitor of the insulin-pathway, they showed that TA-induced glucose transport was blocked when insulin receptor was inhibited. Finally, they demonstrated that TA inhibits adipocytes differentiation affecting genes involved in the adipogenesis process, such as PPARγ, and differentiation process such as c-fos, c-jun and c-myc.

Tannins are polyphenolic compounds found in foods such as vegetables, fruits and beverage. They were reported to possess multiple biological activities including anticancer, antioxidant, and antimicrobial activities. Generally, tannins induce a negative response when consumed. These effects can be instantaneous like astrigency or a bitter or unpleasant taste or can have a delayed response related to antinutritional/toxic effects.

TA is a mixture of tannin compounds and the most effective compound (s) involved in glucose transport stimulation and inhibition of adipocyte differentiation is not yet identified.

Madeglucyl™

Madeglucyl™ is an extract from the seeds of *Syzygium cumini* synonyms *Eugenia jambolana* and *Syzygium jambolanum*, and commonly called jamun, java plum, black plum and Indian black berry. The jamun tree is a large evergreen tree that is native to India and thrives in tropical climates. The seeds, leaves and fruit of the *Syzygium cumini* plant have been used in traditional medicine for its hypoglycemic properties.

The majority of research conducted regarding Syzygium cumini has evaluated the hypoglycemic, hypolipidemic, and antioxidant effects of its leaves, fruit, seeds, and kernels. Only the studies conducted on the seeds and kernels of *Syzygium cumini* have reported positive effects. Interestingly, all of these studies were done using plants grown in India, whereas the studies reporting no effect used the fruit or leaves of the plant and were conducted using plants grown in Brazil.

Sridhar and colleagues studied the effect of *Syzygium cumini* seed powder (250, 500 and 1000 mg/kg) on improving glycemic control in streptozotocin diabetic rats for 15 days. They reported a decrease in fasting blood glucose (−13, −30 and −46 mg/dl) and a decrease in the peak level in the glucose tolerance test (−20, −36 and −46 mg/dl) compared to diabetic controls. Extracts of *Syzygium cumini* seeds have also shown beneficial results on glycemic control and lipid profiles. An aqueous extract of *Syzygium cumini* seed (2.5 and 5.0 g/kg) was fed to alloxan diabetic rats for six weeks and resulted in a significant reduction in blood glucose (−108 and 118 mg/dl) and decreased free radical formation. However, the 7.5 g/kg dose had no significant effect.

Prince and colleagues reported that an alcohol extract (100 mg/kg) decreased fasting blood glucose (−180 mg/dl) levels to the same effect as insulin (−183.1 mg/dl) in alloxan diabetic rats after six weeks. Cholesterol and free fatty acids levels were also similar to normal rats and diabetic rats treated with insulin compared to diabetic rats. Acute results with an alcohol extract of *Syzygium cumini* seed on blood glucose in sub-diabetic, mild diabetic and severe alloxan diabetic rabbits has also been reported. Within 90 minutes of consuming an alcohol extract of *Syzygium cumini* seed (50, 100 and 200 mg/kg), glucose levels were decreased in the mild diabetic rabbits (−20, −29 and −28 mg/dl) and severe diabetic rabbits (−50.4, −74.2 and −77.9 mg/dl). After 15 days of consuming an alcohol extract of *Syzygium cumini* seed (100 mg/kg), glucose levels in mild diabetic (−64 mg/dl) and severe diabetic (−84 mg/dl) rabbits were decreased significantly. Similar results were also reported with total cholesterol, HDL, LDL, VLDL and triglycerides. The effect of *Syzygium cumini* seed extracts have also been shown to reduce tissue damage in diabetic rat brains. It has been reported that following six weeks of an aqueous extract (5 g/kg) lipid and thiobarbituric acid reactive substances (TBARS) were decreased and catalase and superoxide dismutase were increased in the brains of alloxan diabetic rats. However, administration of an alcohol extract brought all of these parameters to near normal levels. It was concluded that an alcohol extract of *Syzygium cumini* seeds is better than aqueous extracts. Based on these data, alcohol extracts of *Syzygium cumini* seeds appear to have both antidiabetic, antihyperlipidemic and antioxidant effects.

The majority of research reviewed examined the effect of Syzygium cumini kernels as an antidiabetic, antioxidant and antihyperlipidemic agent. Grover and colleagues reported that an aqueous extract of Syzygium cumini kernels (200 mg/kg) reduced glucose concentrations (−94.7 mg/dl), prevented polyuria and maintained normal urinary albumin levels in streptozotocin diabetic rats after 40 days. The effect of aqueous, aqueous lyophilized and alcohol extracts of *Syzygium cumini* kernels were examined by Grover and colleagues. They found the 200 mg/kg dose of each extract had similar results on decreasing glucose levels after 3 weeks in alloxan diabetic rats. Further examination of the effects of the aqueous lyophilized extract (four month) on moderate and severe diabetes in rats revealed that plasma glucose levels were partially normalized in moderate diabetes (−194 mg/dl) and only slightly decreased in severe diabetes (−78 mg/dl). Thus, the effect of *Syzygium cumini* kernels may be dependent on the severity of the disease. Vikrant and colleagues examined the effect of both aqueous and alcohol extracts of Syzygium cumini kernels (100, 200 and 400 mg/d) on fructose fed rats and reported that only the aqueous extract at 400 mg/d prevented hyperglycemia and hyperinsulinemia induced by a diet high in fructose (66.46 vs 75.46 mg/dl). In contrast, four separate studies by Ravi and colleagues report the beneficial effects of alcohol extracts of *Syzygium cumini* kernels as an antioxidant, antihyperlipidemic and antidiabetic agent and also reported that the effects mimicked glibenclamide, an oral diabetic agent. In 2004, they published two studies that reported that alcohol extracts of *Syzygium cumini* kernels (100 mg/kg) decreased blood glucose, increased insulin levels, normalized body weight, improved markers of oxidative stress and normalized liver, kidney and pancreatic physiology in streptozotocin induced diabetic rats after 30 days. They have also reported that extracts of *Syzygium cumini* kernels (100 mg/kg) normalized total cholesterol, phosphoplipids, triglycerides and free fatty acids to control levels in streptozotocin induced diabetic rats after 30 days.

To determine the effect of different parts of *Syzygium cumini* seed, Ravi and colleagues evaluated the hypoglycemic activity of *Syzygium cumini* alcohol extracts of whole seeds, kernel and seed coat on streptozotocin induced diabetic rats. They reported that following 30 days of 100 mg/kg of each preparation, the whole seeds had a moderate effect on glucose levels, the kernel normalized glucose levels to that of glibenclamide and the seed coat had no effect on glucose levels. They also found that only the kernel and glibenclamide treatments normalized cholesterol and liver glycogen levels to control levels. Based on these data, *Syzygium cumini* kernels seem to have a positive effect on glucose and lipid levels, and oxidative stress. However, there is no conclusive evidence to as to whether aqueous or alcohol extracts are more beneficial.

It has been reported that aqueous extracts of *Syzygium cumini* contain ellagic acid and alkaloid jambosine and alcohol extracts contain gallic acid, ellagic acid, corilagin and quercetin. The active component in *Syzygium cumini* may be ellagic acid as it is found in both extracts and numerous studies have reported the benefits of both aqueous and alcoholic extracts. However, no studies have been conducted to determine the actual active component in *Syzygium cumini*.

No studies have investigated the mechanism of action for *Syzygium cumini*. However, Ravi, Prince and Grover have suggested that the hypoglycemic action may be due to stimulation of surviving β-cells to release more insulin. This hypothesis is supported by the fact that the hypoglycemic effects are more pronounced with mild to moderate diabetic models compared to severe diabetic models and insulin levels are reported to be increased. In these models, diabetes was induced by alloxan and streptozotocin, that specifically target the destruction of β-cells. Additionally, experiments conducted by Ravi and colleagues included a group of animals that received glibenclamide, and consistently the animals in the *Syzygium cumini* groups had similar results to the animals receiving glibenclamide. Glibenclamide is a sulfonylurea and its mechanism of action is to stimulate insulin secretion from β-cells. Thus, *Syzygium cumini*'s mechanism of action could be to stimulate insulin secretion. Specific mechanistic studies are needed to confirm this hypothesis.

Arginine

It has been hypothesized that specific amino acids may be able to improve glucose control by stimulating insulin secretion. Preliminary research done using mouse models of insulin resistance support this hypothesis. An amino acid blend composed of arginine (1.75 g), phenylalanine (0.40 g) and leucine (1.20 g) improved postprandial glucose response following chronic amino acid feedings. These observations have been confirmed acutely in humans with either arginine alone (2 g) or arginine (4.7 g) and leucine (3.3 g). Both preparations improved glycemic responses compared to a standard formula.

In addition, van Loon and colleagues reported that a wheat protein hydrolysate/amino acid (arginine, phenylalanine and leucine) mixture on insulin response in eight healthy men. Following an overnight fast, subjects consumed carbohydrate alone or carbohydrate with the protein hydrolysate/amino acids mixture. Both treatments resulted in an increase in plasma glucose and insulin. However, the insulin response was significantly greater when the amino acid mixture was consumed with carbohydrate compared to carbohydrates consumed alone. This provides additional evidence to support the hypothesis that specific amino acids are involved with glycemic control by increasing the plasma concentration of insulin.

Research has specifically examined the effect of arginine on increasing insulin sensitivity and its ability to improve glycemic control. This was specifically examined in six people with diabetes who consumed an arginine supplementation (9 g/d) for one month. Compared to placebo, arginine significantly increased forearm blood flow and glucose disposal, as well as decreased systolic blood pressure and endogenous glucose production. In addition, arginine improved insulin sensitivity. Siani and colleagues examined the effect of arginine as from an oral supplement (10 g/d) and an arginine-rich diet (10 g/d). They reported that both supplemental arginine and arginine from the diet decreased systolic and diastolic blood pressure in 6 healthy subjects compared to a control diet (~4 g arginine/d). Blood glucose was significantly decreased by the arginine supplement and slightly decreased by the arginine-rich diet.

In contrast, a study by Gannon and colleagues in nine healthy men showed no significant effect of oral arginine (1 mmol/kg lean body mass, ~10 g average) on insulin concentrations in the 2 hours following ingestion of 25 g of glucose. However, researcher did note an attenuation in the increase in plasma glucose. Thus, the ability of arginine to improve insulin sensitivity and glycemic control may be more efficacious in people with diabetes, as it stimulates increased insulin secretion, which is known to be impaired in people with diabetes.

In addition to its ability to improve insulin sensitivity and glycemic control, arginine is reported to reduce oxidative stress and tissue damage, and improve vascular function. In a crossover study by Lubec and colleagues, lipid peroxidation was significantly reduced by daily supplementation of arginine (1 g/d), as assessed by urinary levels of malondialdehyde in 30 patients with diabetes. The patients were randomly assigned to receive either arginine followed by placebo or vice versa for three months. Interestingly, the malondialdehyde was significantly reduced when patients received arginine treatment and urinary excretion of malondialdehyde was significantly increased when the group receiving arginine was switched to the placebo, indicating a protective effect of arginine as it is able to reduce oxidative stress.

In addition, arginine may be able to reduce oxidative damage to the kidney. The ability of arginine to reduce oxidative stress and kidney tissue damage was investigated in a mouse model of diabetes. Following administration of arginine, lipid peroxidation and glycoxidation, measures of oxidative stress, were significantly decreased. In addition, kidney collagen accumulation, kidney weight and albuminuria were also significantly decreased by arginine. These findings have important implications for nephropathy associated with diabetes, as kidney tissue damage is thought to be related, in part, to increased glomerular collagen accumulation.

Long-term arginine supplementation may also ameliorate endothelial dysfunction, which is among the comorbidities of diabetes. In a group of healthy individuals, arginine supplementation (9 g/d) for 6 months significantly increased small-vessel coronary blood flow in response to acetylcholine compared with a placebo group. Similarly, arginine supplementation for four months (21 g/d) significantly increased endothelium-dependent dilation in hypercholesterolemic subjects with endothelial dysfunction. However, arginine had no effect on lipoprotein levels. Dietary supplementation of arginine (12 g/d for 3 weeks) has been reported to be associated with a small reduction in diastolic blood pressure and moderate reduction in plasma homocysteine in men with hypercholesterolemia. Epidemiological studies have shown that too much homocysteine, an amino acid in the blood, is related to a higher risk of coronary heart disease, stroke and peripheral vascular disease. Thus, arginine may have a significant role helping to manage the long-term complications associated with diabetes.

Arginine regulates many metabolic and physiologic body functions that are critical for efficient wound repair. It is conditionally-essential, meaning that it is required when the body is under stress or in an injured state. Arginine reduces the risk of infectious complications of a wound by stimulating lymphocyte immune responses. It is a precursor to proline, which is converted to hydroxyproline and then to collagen, which is important with wound healing. In addition, arginine is a key element in the synthesis of polyamines that are critical for cell proliferation that is necessary for wound repair. Finally, arginine has been reported to promote increased blood supply to the wound, thereby improving the circulatory system.

Two studies have shown beneficial effects on wound healing. Barbul and colleagues randomized 36 healthy, non-smoking volunteers to a daily supplement of 30 g of arginine hydrochloride (24.8 g of free arginine), 30 g of arginine aspartate (17 g of free arginine), or placebo. Artificial wounds were created and healing monitored over a two week period by measuring the amount of hydroxyproline, an index of new collagen synthesis and deposition. Arginine supplementation significantly enhanced the amount of collagen deposited in a standard wound as assessed by the amount of hydroxyproline present. Additionally, the immune response of volunteers that received arginine was increased.

In a similar study, Kirk and colleagues randomly assigned 30 people greater than 65 years of age to receive a supplement of 30 g of arginine aspartate (17 g of free arginine) and 15 people greater than 65 years of age to receive a placebo. They reported that arginine supplementation significantly enhanced the amount of collagen deposited in a standard wound as assessed by the amount of hydroxyproline present. In addition, the immune response was greater in the arginine supplemented group.

The benefit of arginine and wound healing has also been studied in animal models. Arginine supplemented rats showed improved wound healing compared to arginine deficient rats as judged by the breaking strengths of their incisions, as well as by increased levels of hydroxyproline in sponge granulomas. In addition, arginine accelerates wound healing both diabetic and normal rats. Witte and colleagues performed a study in 36 rats comparing the rate of wound healing in control and diabetic rats with and without an arginine supplement. They found wound breaking strength after 10 days was improved in rats who received the arginine supplement compared to those that did not. This difference was significant for diabetic rats when compared to the controls. Similarly, Shi and colleagues performed a study in 56 rats comparing the rate of wound healing in control and diabetic rats with and without an arginine supplement. They found wound breaking strength after 10 days was significantly improved in both the control and diabetic rats that received the arginine supplement.

Nearly 12% of people in the United States with a diagnosis of diabetes have a history of diabetic foot ulcers, which increases their risk factor for further foot ulcers and lower extremity amputation. In addition, in Europe, approximately 660,000 people with diabetes have a foot ulcer and it is estimated that 10% of these individuals will eventually undergo lower extremity amputation. Thus, the provision of arginine in diabetic formulas is important to prevent and treat diabetes associated wounds.

Polyunsaturated Fatty Acid Ratio

While not constituting an additional ingredient, several researchers have hypothesized that a low ratio of omega-6:omega-3 fatty acids may improve conditions associated with diabetes, including, dyslipidemia, inflammation, and insulin resistance. While omega-3 fatty acids are precursors for metabolites associated with antithrombotic effects, omega-6 fatty acids are substrates for production of eicosanoids that increase thrombosis, aggregation, blood viscosity, and inflammation. Therefore, dietary consumption of greater amounts of omega-6 fatty acids, relative to omega-3 fatty acids, may shift metabolism to favor a pro-inflammatory, proatherogenic physiological environment. These physiological observations suggest that maintaining the proper eicosanoid balance is essential for minimizing negative effects and maximizing potential health benefits of polyunsaturated fatty acids.

Fish Oil: Eicosapentaenoic Acid and Docosahexaenoic Acid

Cardiovascular disease, largely associated with abnormal lipoprotein metabolism, is among the major complications of diabetes. Fish oil has shown beneficial effects on some lipoprotein fractions, such as serum triglycerides. In addition, epidemiological studies suggest that moderate consumption of omega-3 fatty acids from marine fish may reduce cardiovascular disease mortality and reduce the risk of developing glucose intolerance in elderly individuals. Therefore, the American Diabetes Association states that two or more servings per week of omega-3 containing fish should be recommended for individuals with diabetes. Similarly, the American Heart Association recommends that individuals with coronary heart disease consume approximately 1 g eicosapentaenoic acid+docosahexaenoic acid (EPA+DHA) daily, preferably from fatty fish, and if under a physicians care as a supplement. For individuals with hypertriglyceridemia, the American Medical Association suggests daily supplementation of 2 to 4 g per day EPA+DHA, under physicians care.

A meta-analysis demonstrated a significant effect of fish oil (dose range: 3 to 18 g/d) on triglycerides concentrations in individuals with diabetes (decrease of ~0.56 mmol/L). However, the net effect on LDL cholesterol was a significant increase of ~0.21 mmol/L, with effects most notable in studies containing subjects with hypertriglyceridemia. Similar results were presented in an earlier meta-analysis that reported a mean decrease in serum triglycerides of ~0.60 mmol/L, an increase in LDL cholesterol of ~0.18 mmol/L, and no adverse effects on hemoglobin A1c. This analysis found effects of fish oil supplementation on plasma triglycerides concentrations were most pronounced in individuals with diabetes.

Fish oil supplementation has been consistently observed to decrease plasma triglycerides in most studies conducted in individuals with diabetes or hypertriglyceridemia. Fish oil appears to decrease triglycerides concentrations by decreasing hepatic triglyceride production. These data indicate that fish oil supplementation may be a means of correcting the increased hepatic triglycerides synthesis characteristic of insulin resistance. Moreover, animal studies have shown that fish oil may decrease liver and skeletal muscle triglyceride.

While several studies have reported increased LDL cholesterol with fish oil supplementation, others have not reported significant changes in concentrations, or effects varied by dose. Fish oil-induced increases in LDL cholesterol concentrations are likely due to increased conversion of liver-derived VLDL to LDL cholesterol particles. The clinical significance of the observed increases in LDL cholesterol is uncertain, and large variability exists in the literature regarding effects of fish oil on LDL cholesterol concentrations which may be due in part to wide variability in dose administered, duration of supplementation, study design, and subject number.

The cardio-protective effects of fish oil in individuals with diabetes may be mediated, in part, by enhanced arterial compliance and platelet function, and reduced oxidative stress (Mori TA 2000) and inflammation. Results of a large, randomized placebo-controlled trial showed that fish oil consumption (~1.08 g EPA/d) reduced cardiovascular disease events in the absence of changes in lipoproteins. This observation, coupled with the reduction in conjugated diene formation in the fish oil group, lead researchers to hypothesize that cardioprotection was due to a reduction in oxidative stress.

Intervention trials reporting the effects of fish oil on glycemic control have made varying conclusions, with some showing improved, unaffected, or decreased glycemic control as measured by fasting glucose, hemoglobin A1c, and/or glucose disappearance rates. The research of Hendra and colleagues suggests that duration of supplementation may influence outcomes. After three weeks of 10 g per day fish oil supplementation, researchers observed significantly increased fasting blood glucose in 40 patients with diabetes, but by the end of the six week intervention, difference from baseline was no longer statistically significant. The level of supplementation had an effect in the study by Schectman and colleagues who reported that fasting blood glucose and glycated hemoglobin increased significantly during one month of 7.5 g per day fish oil supplementation but not during 4 g per day supplementation. Overall, three fairly large meta-analyses summarize this data well, finding no significant effects of fish oil on glycemic control.

Similar to the effects of fish oil on glycemic control, effects on insulin sensitivity have been mixed. Animal studies suggest that insulin sensitivity may be enhanced by fish oil-containing diets. In individuals with diabetes, ex vivo insulin sensitivity improved with 3 g fish oil per day in one study, but sensitivity was compromised in another study (10 g/d) as assessed by insulin-stimulated glucose disappearance. Other studies have found neither favorable nor unfavorable effects on insulin sensitivity in individuals with diabetes.

Other Ingredients

Other ingredients suitable for inclusion in a nutritional formula having a 1:1:1 carbohydrate:fat:protein ratio such as those described above include chlorogenic acid (inhibits sodium-dependent glucose transport), mangosteen (an antioxidant and antiinflammatory related to IKK inhibition), palm oil mill waste (phenolics that increase antioxidant activity and decrease atherosclerosis lesions), chromium (increases insulin sensitivity and improves glycemic control), vanadium (exhibits insulin-like activity, stimulates glucose uptake, and inhibits protein tyrosine phosphatase and gluconeogenesis), and compounds capable of increasing insulin-dependent glucose metabolism in adipocytes (e.g., witch hazel, allspice, bay leaves, nutmeg, cloves, mushrooms, and saccharomyces cerevisiae).

It should be appreciated that the present invention is not limited to the specific embodiments described above, but includes variations, modifications and equivalent embodiments defined by the following claims.

What is claimed is:

1. A nutritional formulation comprising:
 a protein source;
 a fat source comprising greater than about 2% of the total calories of the composition in the form of linoleic acid (18:2); and
 a carbohydrate source,
 wherein the protein source and the fat source are in a ratio of about 1:1, each of the protein source and the fat source comprising between about 15% and about 45% of the total calories of the composition, and wherein the protein source, fat source, and carbohydrate source are not in a ratio of 30:30:40.

2. The nutritional formulation of claim 1, wherein the protein source and the fat source each comprise about 25% of the total calories of the composition.

3. The nutritional formulation of claim 1, wherein the protein source and the fat source each comprise about 30% of the total calories of the composition.

4. The nutritional formulation of claim 1, wherein the protein source and the fat source each comprise about 35% of the total calories of the composition.

5. The nutritional formulation of claim 1, wherein the protein source and the fat source each comprise about 20% to about 40% of the total calories of the composition 6. The nutritional formulation of claim 1, wherein the protein source and the fat source each comprise about 25% to about 35% of the total calories of the composition.

7. The nutritional formulation of claim 1, wherein the protein source and the fat source each comprise about 30% to about 35% of the total calories of the composition.

8. The nutritional formulation of claim 1, wherein the fat source is comprised of about 2% to about 10% of the total calories of the composition in the form of linoleic acid (18:2).

9. The nutritional formulation of claim 1, wherein the fat source is comprised of about 4% to about 7% of the total calories of the composition in the form of linoleic acid (18:2).

10. The nutritional formulation of claim 1, wherein the fat source is comprised of about 5% to about 6% of the total calories of the composition in the form of linoleic acid (18:2).

11. The nutritional formulation of claim 1, wherein the fat source is comprised of about 4% of the total calories of the composition in the form of linoleic acid (18:2).

12. The nutritional formulation of claim 1, wherein the fat source is comprised of about 5% of the total calories of the composition in the form of linoleic acid (18:2).

13. The nutritional formulation of claim 1, wherein the fat source is comprised of about 6% of the total calories of the composition in the form of linoleic acid (18:2).

14. The nutritional formulation of claim 1, wherein the fat source is comprised of about 7% of the total calories of the composition in the form of linoleic acid (18:2).

15. The nutritional formulation of claim 1, wherein the fat source is comprised of about 8% of the total calories of the composition in the form of linoleic acid (18:2).

16. The nutritional formulation of claim 1, further comprising at least one of the following: touchi extract, partially hydrolyzed guar gum, inulin, a fructooligosaccharide, a galactooligosaccharide, isomaltulose, sucromalt, trehalose, lipoic acid, 4-hydroxyisoleucine catechin, cinnamon, banaba extract, madeglucyl, arginine, a branched chain amino acid, glutamine, glutamate, fish oil, chlorogenic acid, mangosteen, palm oil mill waste, chromium, vanadium, witch hazel, allspice, bay leaves, nutmeg, cloves, mushrooms, saccharomyces cerevisiae, and a combination thereof.

17. A dietary regime for increasing insulin sensitivity comprising:
a protein source;
a fat source comprising greater than about 2% of the total calories of the composition in the form of linoleic acid (18:2); and
a carbohydrate source,
wherein the protein source and the fat source are in a ratio of about 1:1, wherein each of the protein source and the fat source comprises between about 15% and about 45% of the total calories of the dietary regime, and wherein the protein source, fat source, and carbohydrate source are not in a ratio of 30:30:40.

18. The dietary regime of claim 17, wherein the protein source and the fat source each comprise about 25% of the total calories of the dietary regime.

19. The dietary regime of claim 17, wherein the protein source and the fat source each comprise about 30% of the total calories of the dietary regime.

20. The dietary regime of claim 17, wherein the protein source and the fat source each comprise about 35% of the total calories of the dietary regime.

21. The dietary regime of claim 17, wherein the protein source and the fat source each comprise about 20% to about 40% of the total calories of the dietary regime.

22. The dietary regime of claim 17, wherein the protein source and the fat source each comprise about 25% to about 35% of the total calories of the dietary regime.

23. The dietary regime of claim 17, wherein the protein source and the fat source each comprise about 30% to about 35% of the total calories of the dietary regime.

24. The dietary regime of claim 17, wherein the fat source is comprised of between about 2% and about 10% of the total calories of the dietary regime in the form of linoleic acid (18:2).

25. The dietary regime of claim 17, wherein the fat source is comprised of between about 4% and about 7% of the total calories of the dietary regime in the form of linoleic acid (18:2).

26. The dietary regime of claim 17, wherein the fat source is comprised of between about 5% and about 6% of the total calories of the dietary regime in the form of linoleic acid (18:2).

27. The dietary regime of claim 17, wherein the fat source is comprised of about 4% of the total calories of the dietary regime in the form of linoleic acid (18:2).

28. The dietary regime of claim 17, wherein the fat source is comprised of about 5% of the total calories of the dietary regime in the form of linoleic acid (18:2).

29. The dietary regime of claim 17, wherein the fat source is comprised of about 6% of the total calories of the dietary regime in the form of linoleic acid (18:2).

30. The dietary regime of claim 17, wherein the fat source is comprised of about 7% of the total calories of the dietary regime in the form of linoleic acid (18:2).

31. The dietary regime of claim 17, wherein the fat source is comprised of about 8% of the total calories of the dietary regime in the form of linoleic acid (18:2).

32. The dietary regime of claim 17, further comprising at least one of the following: touchi extract, partially hydrolyzed guar gum, inulin, a fructooligosaccharide, a galactooligosaccharide, isomaltulose, sucromalt, trehalose, lipoic acid, 4-hydroxyisoleucine, catechin, cinnamon, banaba extract, madeglucyl, arginine, a branched chain amino acid, glutamine, glutamate, fish oil, chlorogenic acid, mangosteen, palm oil mill waste, chromium, vanadium, witch hazel, allspice, bay leaves, nutmeg, cloves, mushrooms, saccharomyces cerevisiae, and a combination thereof.

* * * * *